US009982042B2

(12) United States Patent
Stagg et al.

(10) Patent No.: US 9,982,042 B2
(45) Date of Patent: *May 29, 2018

(54) THERAPEUTIC COMBINATION AND METHODS OF TREATMENT WITH A DLL4 ANTAGONIST AND AN ANTI-HYPERTENSIVE AGENT

(71) Applicant: OncoMed Pharmaceuticals, Inc., Redwood City, CA (US)

(72) Inventors: Robert Joseph Stagg, Moraga, CA (US); Steven Eugene Benner, Seattle, WA (US)

(73) Assignee: OncoMed Pharmaceuticals, Inc., Redwood City, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/336,272

(22) Filed: Oct. 27, 2016

(65) Prior Publication Data

US 2017/0166632 A1   Jun. 15, 2017

Related U.S. Application Data

(62) Division of application No. 14/498,602, filed on Sep. 26, 2014, now Pat. No. 9,511,139, which is a division of application No. 13/501,944, filed as application No. PCT/US2010/053064 on Oct. 18, 2010, now Pat. No. 8,883,145.

(60) Provisional application No. 61/252,473, filed on Oct. 16, 2009.

(51) Int. Cl.

| | |
|---|---|
| A61K 39/395 | (2006.01) |
| A61P 9/12 | (2006.01) |
| A61K 31/138 | (2006.01) |
| A61K 31/5377 | (2006.01) |
| A61K 31/166 | (2006.01) |
| A61K 31/401 | (2006.01) |
| A61K 31/4184 | (2006.01) |
| A61K 31/4418 | (2006.01) |
| A61K 31/519 | (2006.01) |
| A61K 31/55 | (2006.01) |
| C07K 16/18 | (2006.01) |
| A61K 45/06 | (2006.01) |
| C07K 16/22 | (2006.01) |
| C07K 16/24 | (2006.01) |
| A61K 39/00 | (2006.01) |

(52) U.S. Cl.
CPC ............ *C07K 16/18* (2013.01); *A61K 31/138* (2013.01); *A61K 31/166* (2013.01); *A61K 31/401* (2013.01); *A61K 31/4184* (2013.01); *A61K 31/4418* (2013.01); *A61K 31/519* (2013.01); *A61K 31/5377* (2013.01); *A61K 31/55* (2013.01); *A61K 39/3955* (2013.01); *A61K 45/06* (2013.01); *A61K 39/39558* (2013.01); *A61K 2039/505* (2013.01); *C07K 16/22* (2013.01); *C07K 16/24* (2013.01); *C07K 2317/31* (2013.01); *C07K 2317/56* (2013.01); *C07K 2317/565* (2013.01); *C07K 2317/76* (2013.01); *Y10S 530/80* (2013.01); *Y10S 530/86* (2013.01)

(58) Field of Classification Search
CPC .............. A61K 2300/00; A61K 39/395; A61K 2039/505; A61K 39/39558; A61K 39/3955; C07K 16/22; C07K 2317/565; C07K 2317/56; C07K 2317/76; C07K 2317/24; C07K 16/18; C07K 16/24
See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen |
| 4,544,545 A | 10/1985 | Ryan et al. |
| 4,816,567 A | 3/1989 | Cabilly et al. |
| 5,013,556 A | 5/1991 | Woodle et al. |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,661,016 A | 8/1997 | Lonberg et al. |
| 5,693,761 A | 12/1997 | Queen et al. |
| 5,693,762 A | 12/1997 | Queen et al. |
| 5,730,977 A | 3/1998 | Ooka et al. |
| 5,731,168 A | 3/1998 | Carter et al. |

(Continued)

FOREIGN PATENT DOCUMENTS

| | | |
|---|---|---|
| CA | 2789446 A1 | 8/2011 |
| EP | 0662827 A1 | 7/1995 |

(Continued)

OTHER PUBLICATIONS

Al-Hajj, M., et al., "Prospective Identification of Tumorigenic Breast Cancer Cells," Proceedings of the National Academy of Sciences 100(7):3983-3988, The National Academy of Sciences, United States (2003).
Allenspach, E.J., et al., "Notch Signaling in Cancer," Cancer Biology Therapy 1(5):466-476, Informa UK Limited, United Kingdom (2002).
Amado, R.G., et al., "Wild-Type KRAS is Required for Panitumumab Efficacy in Patients with Metastatic Colorectal Cancer,"Journal of Clinical Oncology 26(10):1626-1634, American Society of Clinical Oncology, United States (2008).
Artavanis-Tsakonas, S., et al., "Notch Signaling: Cell Fate Control and Signal Integration in Development," Science 284(5415):770-776, American Association for the Advancement of Science, United States (1999).

(Continued)

*Primary Examiner* — Bridget E Bunner
(74) *Attorney, Agent, or Firm* — Sterne, Kessler, Goldstein & Fox P.L.L.C.

(57) ABSTRACT

Methods for treating cancer comprising administering a DLL4 antagonist and one or more anti-hypertensive agents are described. Also described are pharmaceutical compositions comprising a DLL4 antagonist and one or more anti-hypertensive agents, and kits comprising the same.

51 Claims, 10 Drawing Sheets

(56) References Cited

U.S. PATENT DOCUMENTS

| | | |
|---|---|---|
| 5,750,373 A | 5/1998 | Garrard et al. |
| 5,840,299 A | 11/1998 | Bendig et al. |
| 6,004,528 A | 12/1999 | Bergstein |
| 6,024,955 A | 2/2000 | Asano et al. |
| 6,121,045 A | 9/2000 | McCarthy et al. |
| 6,262,025 B1 | 7/2001 | Ish-Horowicz et al. |
| 6,342,219 B1 | 1/2002 | Thorpe et al. |
| 6,524,583 B1 | 2/2003 | Thorpe et al. |
| 6,582,959 B2 | 6/2003 | Kim |
| 6,664,098 B1 | 12/2003 | Sakano |
| 6,676,941 B2 | 1/2004 | Thorpe et al. |
| 6,689,744 B2 | 2/2004 | Gao et al. |
| 6,887,468 B1 | 5/2005 | Thorpe et al. |
| 6,984,522 B2 | 1/2006 | Clarke et al. |
| 7,022,499 B2 | 4/2006 | Sakano |
| 7,056,509 B2 | 6/2006 | Thorpe et al. |
| 7,060,269 B1 | 6/2006 | Baca et al. |
| 7,118,890 B2 | 10/2006 | Ish-Horowicz et al. |
| 7,183,076 B2 | 2/2007 | Arathoon et al. |
| 7,227,004 B2 | 6/2007 | Kim |
| 7,354,581 B2 | 4/2008 | Cedarbaum et al. |
| 7,449,182 B2 | 11/2008 | Cedarbaum et al. |
| 7,482,005 B2 | 1/2009 | Kim et al. |
| 7,488,806 B2 | 2/2009 | Papadopoulos et al. |
| 7,531,172 B2 | 5/2009 | Stahl et al. |
| 7,534,868 B1 | 5/2009 | Papadopoulos et al. |
| 7,750,124 B2 | 7/2010 | Gurney et al. |
| 7,754,206 B2 | 7/2010 | Clarke et al. |
| 7,758,859 B2 | 7/2010 | Fuh et al. |
| 7,803,377 B2 | 9/2010 | Yan et al. |
| 7,897,725 B2 | 3/2011 | McCarthy et al. |
| 7,906,116 B2 | 3/2011 | Gill et al. |
| 7,910,098 B2 | 3/2011 | Fuh et al. |
| 7,919,593 B2 | 4/2011 | Papadopoulos et al. |
| 7,951,917 B1 | 5/2011 | Arathoon et al. |
| 8,048,418 B2 | 11/2011 | Noguera-Troise et al. |
| 8,133,857 B2 | 3/2012 | Aikawa |
| 8,192,738 B2 | 6/2012 | Bedian et al. |
| 8,216,571 B2 | 7/2012 | Ramachandra et al. |
| 8,404,233 B2 | 3/2013 | Sunamura et al. |
| 8,518,887 B2 | 8/2013 | Noguera-Troise et al. |
| 8,557,965 B2 | 10/2013 | Saunders et al. |
| 8,685,401 B2 | 4/2014 | Harris et al. |
| 8,765,125 B2 | 7/2014 | Skokos |
| 8,840,886 B2 | 9/2014 | Noguera-Troise et al. |
| 8,858,941 B2 | 10/2014 | Gurney et al. |
| 8,883,145 B2 | 11/2014 | Stagg et al. |
| 8,889,131 B2 | 11/2014 | Aikawa et al. |
| 8,889,133 B2 | 11/2014 | Skokos |
| 9,029,508 B2 | 5/2015 | Ghayur et al. |
| 9,115,195 B2 | 8/2015 | Chen et al. |
| 9,132,190 B2 | 9/2015 | Benatuil et al. |
| 9,228,020 B2 | 1/2016 | Gurney et al. |
| 9,309,311 B2 | 4/2016 | Gurney et al. |
| 9,376,488 B2 | 6/2016 | Gurney et al. |
| 9,376,497 B2 | 6/2016 | Gurney et al. |
| 9,403,904 B2 | 8/2016 | Smider et al. |
| 9,469,689 B2 | 10/2016 | Chen et al. |
| 9,511,139 B2 | 12/2016 | Stagg et al. |
| 9,599,620 B2 | 3/2017 | Benner et al. |
| 2002/0028488 A1 | 3/2002 | Singh et al. |
| 2002/0032315 A1 | 3/2002 | Baca et al. |
| 2002/0119153 A1 | 8/2002 | Thorpe et al. |
| 2003/0175877 A1 | 9/2003 | Baker et al. |
| 2003/0180784 A1 | 9/2003 | McCarthy et al. |
| 2004/0123343 A1 | 6/2004 | La Rosa et al. |
| 2004/0133357 A1 | 7/2004 | Zhong et al. |
| 2004/0265307 A1 | 12/2004 | Singh et al. |
| 2004/0265309 A1 | 12/2004 | Kandel et al. |
| 2005/0026831 A1 | 2/2005 | Bodmer et al. |
| 2005/0054036 A1 | 3/2005 | Bates et al. |
| 2005/0059093 A1 | 3/2005 | Bodmer et al. |
| 2005/0079184 A1 | 4/2005 | Hsing-Chang et al. |
| 2005/0089518 A1 | 4/2005 | Clarke et al. |
| 2005/0112121 A1 | 5/2005 | Artavanis-Tsakonas et al. |
| 2005/0137130 A1 | 6/2005 | Bodmer et al. |
| 2005/0261477 A1 | 11/2005 | Champion et al. |
| 2005/0276808 A1 | 12/2005 | Cedarbaum |
| 2005/0281822 A1 | 12/2005 | Cedarbaum et al. |
| 2006/0084588 A1 | 4/2006 | Briend et al. |
| 2006/0122373 A1 | 6/2006 | McCarthy et al. |
| 2006/0134080 A1 | 6/2006 | Lyden et al. |
| 2006/0134121 A1 | 6/2006 | Thurston et al. |
| 2006/0280747 A1 | 12/2006 | Fuh et al. |
| 2007/0004909 A1 | 1/2007 | Johnson et al. |
| 2007/0020267 A1 | 1/2007 | Fuh et al. |
| 2007/0036797 A1 | 2/2007 | Kim et al. |
| 2007/0082846 A1 | 4/2007 | Ish-Horowicz et al. |
| 2007/0098712 A1 | 5/2007 | Arathoon et al. |
| 2007/0141065 A1 | 6/2007 | Fuh et al. |
| 2007/0154391 A1 | 7/2007 | Kim et al. |
| 2007/0178552 A1 | 8/2007 | Arathoon et al. |
| 2007/0190573 A1 | 8/2007 | Hess et al. |
| 2007/0190647 A1 | 8/2007 | Clarke et al. |
| 2007/0196374 A1 | 8/2007 | Baca et al. |
| 2007/0202102 A1 | 8/2007 | Bizzini et al. |
| 2007/0212354 A1 | 9/2007 | Yung et al. |
| 2007/0213266 A1 | 9/2007 | Gill et al. |
| 2007/0231325 A1 | 10/2007 | Clarke et al. |
| 2007/0287170 A1 | 12/2007 | Davis et al. |
| 2008/0014196 A1 | 1/2008 | Yan |
| 2008/0063635 A1 | 3/2008 | Takahashi et al. |
| 2008/0069820 A1 | 3/2008 | Fuh et al. |
| 2008/0107648 A1 | 5/2008 | Noguera et al. |
| 2008/0175847 A1 | 7/2008 | Yan et al. |
| 2008/0181893 A1 | 7/2008 | Lobov et al. |
| 2008/0181899 A1 | 7/2008 | Papadopoulos et al. |
| 2008/0220495 A1 | 9/2008 | McCarthy et al. |
| 2009/0004205 A1 | 1/2009 | Clarke et al. |
| 2009/0023591 A1 | 1/2009 | Spanuth |
| 2009/0035308 A1 | 2/2009 | Gill et al. |
| 2009/0217401 A1 | 8/2009 | Korman et al. |
| 2009/0221549 A1 | 9/2009 | Gerber et al. |
| 2009/0246199 A1 | 10/2009 | Noguera-Troise et al. |
| 2009/0286956 A1 | 11/2009 | McCarthy |
| 2010/0015133 A1 | 1/2010 | Igawa et al. |
| 2010/0076178 A1 | 3/2010 | Ghayur et al. |
| 2010/0086544 A1 | 4/2010 | Mass et al. |
| 2010/0119526 A1 | 5/2010 | Hellstroem |
| 2010/0129356 A1 | 5/2010 | Yan |
| 2010/0150940 A1 | 6/2010 | Adam et al. |
| 2010/0215779 A1 | 8/2010 | Currie et al. |
| 2010/0221250 A1 | 9/2010 | Kim et al. |
| 2010/0260668 A1 | 10/2010 | Ghayur et al. |
| 2010/0266589 A1 | 10/2010 | Hedrick et al. |
| 2010/0272733 A1 | 10/2010 | Bates et al. |
| 2010/0286374 A1 | 11/2010 | Kannan et al. |
| 2010/0316637 A1 | 12/2010 | Gurney et al. |
| 2011/0052575 A1 | 3/2011 | Baca et al. |
| 2011/0052576 A1 | 3/2011 | Ferrara et al. |
| 2011/0076279 A1 | 3/2011 | Ramachandra et al. |
| 2011/0081342 A1 | 4/2011 | Baca et al. |
| 2011/0091372 A1 | 4/2011 | Ghayur et al. |
| 2011/0113865 A1 | 5/2011 | Hess et al. |
| 2011/0117079 A1 | 5/2011 | Benatuil et al. |
| 2011/0123532 A1 | 5/2011 | Gurney et al. |
| 2011/0165162 A1 | 7/2011 | Hoey et al. |
| 2011/0172398 A1 | 7/2011 | Borges et al. |
| 2011/0217237 A1 | 9/2011 | Chen et al. |
| 2011/0306044 A1 | 12/2011 | McCarthy et al. |
| 2012/0116057 A1 | 5/2012 | Kannan et al. |
| 2012/0245151 A1 | 9/2012 | Gavai et al. |
| 2012/0288496 A1 | 11/2012 | Gurney et al. |
| 2013/0131076 A1 | 5/2013 | Fernandez et al. |
| 2013/0164295 A1 | 6/2013 | Gurney et al. |
| 2013/0253172 A1 | 9/2013 | Gurney et al. |
| 2013/0309250 A1 | 11/2013 | Cogswell et al. |
| 2013/0323248 A1 | 12/2013 | Gros et al. |
| 2013/0323260 A1 | 12/2013 | Walsh et al. |
| 2013/0323265 A1 | 12/2013 | Stagg et al. |
| 2014/0017244 A1 | 1/2014 | Duerr et al. |
| 2014/0093499 A1 | 4/2014 | Gschwind et al. |
| 2014/0134169 A1 | 5/2014 | Kuhnert et al. |
| 2014/0206853 A1 | 7/2014 | Foltz et al. |

(56) References Cited

U.S. PATENT DOCUMENTS

| | | |
|---|---|---|
| 2014/0220001 A1 | 8/2014 | Benner et al. |
| 2014/0227252 A1 | 8/2014 | Benner et al. |
| 2014/0348835 A1 | 11/2014 | Gu et al. |
| 2015/0005475 A1 | 1/2015 | Kucia et al. |
| 2015/0098949 A1 | 4/2015 | Gurney et al. |
| 2015/0118232 A1 | 4/2015 | Stagg et al. |
| 2015/0183856 A1 | 7/2015 | Kim et al. |
| 2016/0068596 A1 | 3/2016 | De Sauvage et al. |
| 2016/0362499 A1 | 12/2016 | Gurney et al. |

FOREIGN PATENT DOCUMENTS

| | | |
|---|---|---|
| EP | 0861894 A1 | 9/1998 |
| EP | 1004669 A1 | 5/2000 |
| EP | 0662827 B1 | 4/2002 |
| EP | 1179541 B1 | 6/2004 |
| EP | 0979281 B1 | 7/2005 |
| EP | 1615036 A1 | 1/2006 |
| EP | 0972041 B1 | 10/2006 |
| EP | 1810979 A1 | 7/2007 |
| EP | 1870459 A1 | 12/2007 |
| GB | 2449354 A | 11/2008 |
| JP | 2011505135 A | 2/2011 |
| WO | WO-9219734 A1 | 11/1992 |
| WO | WO-9407474 A1 | 4/1994 |
| WO | WO-9701571 A1 | 1/1997 |
| WO | WO-9845331 A2 | 10/1998 |
| WO | WO-9845434 A1 | 10/1998 |
| WO | WO-9851799 A1 | 11/1998 |
| WO | WO-9857621 A1 | 12/1998 |
| WO | WO-0006726 A2 | 2/2000 |
| WO | WO-0075319 A1 | 12/2000 |
| WO | WO-0140466 A2 | 6/2001 |
| WO | WO-0212447 A2 | 2/2002 |
| WO | WO-03041735 A2 | 5/2003 |
| WO | WO-03050502 A2 | 6/2003 |
| WO | WO-2004110490 A2 | 12/2004 |
| WO | WO-2006027693 A2 | 3/2006 |
| WO | WO-2006028936 A2 | 3/2006 |
| WO | WO-2006033386 A1 | 3/2006 |
| WO | WO-2006052128 A1 | 5/2006 |
| WO | WO-2006106905 A1 | 10/2006 |
| WO | WO-2007028110 A2 | 3/2007 |
| WO | WO-2007070671 A2 | 6/2007 |
| WO | WO-2007143689 A2 | 12/2007 |
| WO | WO-2007145840 A2 | 12/2007 |
| WO | WO-2007147901 A1 | 12/2007 |
| WO | WO-2008042236 A2 | 4/2008 |
| WO | WO-2008060705 A2 | 5/2008 |
| WO | WO-2008070042 A2 | 6/2008 |
| WO | WO-2008076379 A2 | 6/2008 |
| WO | WO-2008079326 A2 | 7/2008 |
| WO | WO-2008091222 A1 | 7/2008 |
| WO | WO-2008139202 A1 | 11/2008 |
| WO | WO-2009073160 A1 | 6/2009 |
| WO | WO-2009075565 A1 | 6/2009 |
| WO | WO-2009080251 A1 | 7/2009 |
| WO | WO-2009085209 A2 | 7/2009 |
| WO | WO-2009089004 A1 | 7/2009 |
| WO | WO-2009134776 A2 | 11/2009 |
| WO | WO-2010010153 A1 | 1/2010 |
| WO | WO-2010054010 A1 | 5/2010 |
| WO | WO-2010124009 A2 | 10/2010 |
| WO | WO-2010129304 A2 | 11/2010 |
| WO | WO-2011039370 A1 | 4/2011 |
| WO | WO-2011047383 A1 | 4/2011 |
| WO | WO-2011047442 A1 | 4/2011 |
| WO | WO-2011068840 A1 | 6/2011 |
| WO | WO-2011100566 A1 | 8/2011 |
| WO | WO-2011109298 A2 | 9/2011 |
| WO | WO-2012068098 A1 | 5/2012 |
| WO | WO-2013044215 A1 | 3/2013 |
| WO | WO-2014049100 A1 | 4/2014 |
| WO | WO-2015130751 A1 | 9/2015 |

OTHER PUBLICATIONS

Axelson, H., "Notch Signaling and Cancer: Emerging Complexity," Seminars in Cancer Biology 14(5):317-319, Academic Press, England (2004).

Barbas, C.F. 3rd., et al., "In vitro evolution of a neutralizing human antibody to human immunodeficiency virus type 1 to enhance affinity and broaden strain cross-reactivity," Proceedings of the National Academy of Sciences 91(9):3809-3813, National Academy of Sciences, United States (1994).

Beachy, P.A., et al., "Tissue Repair and Stem Cell Renewal in Carcinogenesis," Nature 432(7015):324-331, Nature Publishing Group, England (2004).

Bellavia, D., et al., "Constitutive Activation of NF-κB and T-cell Leukemia/lymphoma in Notch3 Transgenic Mice," The EMBO Journal 19(13):3337-3348, European Molecular Biology Organization, Germany (2000).

Benvenuti, S., et al., "Oncogenic activation of the RAS/RAF signaling pathway impairs the response of metastatic colorectal cancers to anti-epidermal growth factor receptor antibody therapies," Cancer Research 67(6):2643-2648, American Association for Cancer Research, United States (2007).

Besseyrias, V., et al., "Hierarchy of Notch-Delta interactions promoting T cell lineage commitment and maturation," The Journal of Experimental Medicine 204(2)331-343, The Rockefeller University Press, United States (2007).

Beviglia, L., et al., "Anti-DLL4 reduces tumor growth and tumorigenicity in B-RAF V600E melanomas including those with acquired resistance to B-RAF inhibitors," AACR 103rd Annual Meeting, Mar. 31-Apr. 4, 2012, Abstract LB-196, 1 page (2012).

Beviglia, L., et al., "Anti-DLL4 Treatment Inhibits Melanoma Tumor Growth, Recurrence, Metastases and Reduces Frequency of Cancer Stem Cells in a Clinically Relevant Tumor Model in NOD/SCID Mice," Cancer Research 71(8 Suppl):Abstract 2834, AACR 102nd Annual Meeting 2011, Apr. 2-6, 2011.

Beviglia, L., et al., "In vivo evaluation of anti-tumor activity by an anti-VEGF and anti-DLL4 bispecific antibody in a humanized model of skin graft," AACR 104th Annual Meeting 2013, Abstract 4330, Apr. 6-10, 1 page (2013).

Bloom, J.W., et al, "Intrachain disulfide bond in the core hinge region of human IgG4," Protein Science 6(2):407-415, John Wiley & Sons, Inc., United States (1997).

Boerner, P., et al., "Production of Antigen-specific Human Monoclonal Antibodies from in Vitro-primed Human Splenocytes," Journal of Immunology 147(1):86-95, The American Association of Immunologists, United States (1991).

Bonnet, D. and Dick, J.E., "Human acute myeloid leukemia is organized as a hierarchy that originates from a primitive hematopoietic cell," Nature Medicine 3(7):730-737, Nature Publishing Company, United States (1997).

Bray, S.J., "Notch signalling: a simple pathway becomes complex," Nature Reviews Molecular Cell Biology 7(9):678-689, Nature Publishing Group, United States (2006).

Brennan, K. and Brown, A.M., "Is there a Role for Notch Signalling in Human Breast Cancer?," Breast Cancer Research 5(2):69-75, BioMed Central Ltd., United Kingdom (2003).

Brennan, M., et al., "Preparation of Bispecific Antibodies by Chemical Recombination of Monoclonal Immunoglobulin G1 Fragments," Science 229(4708):81-83, American Association for the Advancement of Science, United States (1985).

Brorson, K., et al., "Mutational Analysis of Avidity and Fine Specificity of Anti-Levan Antibodies," Journal of Immunology 163(12):6694-6701, American Association of Immunologists, United States (1999).

Brummell, D.A., et al., "Probing the Combining Site of an Anti-Carbohydrate Antibody by Saturation-Mutagenesis: Role of the Heavy-Chain CDR3 Residues," Biochemistry 32(4):1180-1187, American Chemical Society, United States (1993).

Burgess, W.H., et al., "Possible Dissociation of the Heparin-binding and Mitogenic Activities of Heparin-binding (Acidic Fibroblast) Growth Factor-1 from Its Receptor-binding Activities by Site-

(56) References Cited

OTHER PUBLICATIONS directed Mutagenesis of a Single Lysine Residue," The Journal of Cell Biology 111(5Pt1):2129-2138, The Rockefeller University Press, United States (1990).
Burks, E.A., et al., "In vitro Scanning Saturation Mutagenesis of an Antibody Binding Pocket," Proceedings of the National Academy of Sciences USA 94(2):412-417, National Academy of Sciences, United States (1997).
Callahan, R. and Raafat, A., "Notch Signaling in Mammary Gland Tumorigenesis," Journal of Mammary Gland Biology and Neoplasia 6(1):23-36, Kluwer Academic/Plenum Publishers, United States (2001).
Carter, P., "Improving the efficacy of antibody-based cancer therapies," Nature Reviews Cancer 1(2):118-129, Nature Publishing Group, United States (2001).
Chartier, C., et al., "The Hippo Signaling Pathway Mediates BMP Inhibition of Cancer Stem Cells," 2015 AACR Annual meeting, Apr. 18-22, Abstract 2322, 1 page (2015).
Chau, I. and Cunningham, D., "Treatment in advanced colorectal cancer: what, when and how?," British Journal of Cancer 100(11):1704-1719, Nature Publishing Group, United States (2009).
Chen, C., et al., "Generation and Analysis of Random Point Mutations in an Antibody CDR2 Sequence: Many Mutated Antibodies Lose their Ability to Bind Antigen," The Journal of Experimental Medicine 176(3):855-866, Rockefeller University Press, United States (1992).
Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, England (1999).
Chi, A.S., et al., "Angiogenesis as a Therapeutic Target in Malignant Gliomas," Oncologist 14(6):621-636, AlphaMed Press, United States (2009).
Chothia, C. and Lesk, A.M., "Canonical Structures for the Hypervariable Regions of Immunoglobulins," Journal of Molecular Biology 196(4):901-917, Elsevier Science, United States (1987).
Chothia, C., et al., "Domain association in immunoglobulin molecules. The packing of variable domains," Journal of Molecular Biology 186(3):651-663, Elsevier Science, England (1985).
Chowdhury, P.S. and Pastan, I., "Improving Antibody Affinity by Mimicking Somatic Hypermutation in vitro," Nature Biotechnology 17(6):568-572, Nature Publishing Group, United States (1999).
Clarke, M.F., et al., "Cancer stem cells—perspectives on current status and future directions: AACR Workshop on cancer stem cells," Cancer Research 66(19):9339-9344, American Association for Cancer Research, United States (2006).
Claxton, S. and Fruttiger, M., "Periodic Delta-like 4 expression in developing retinal arteries," Gene Expression Pattern 5:123-127, Elsevier B.V., Netherlands (2004).
Cole, S.P.C., et al., "The EBV-Hybridoma Technique and Its Application to Human Lung Cancer," Monoclonal Antibodies and Cancer Therapy, 77-96, Proceedings of the Roche-UCLA Symposium, United States (1985).
Colman, P.M., "Effects of Amino Acid Sequence Changes on Antibody-antigen Interactions," Research in Immunology 145(1):33-36, Elsevier, France (1994).
Cubillo, A., et al., "A Ph1b Study of Demcizumab (DEM, anti-DLL4) with Gemcitabine (GEM) in Patients with 1st Line Locally Advanced or Metastatic Pancreatic Cancer," AACR-NCI-EORTC International Conference on Molecular Targets and Cancer Therapeutics, Oct. 19-23, 2013, Poster (2013), 8 pages.
Cubillo, A., et al., "A Phase lb study of demcizumab (DEM, anti-DLL4) with gemcitabine (GEM) in patients with first line locally advanced or metastatic pancreatic cancer," Proceedings of the AACR-NCI-EORTC International Conference on Molecular Targets and Cancer Therapeutics, Oct. 19-23, 2013, Abstract B78, 2 pages (2013).

Dalerba, P., et al., "Phenotypic characterization of human colorectal cancer stem cells," Proceedings of the National Academy of Sciences 104(24):10158-10163, National Academy of Sciences, United States (2007).
Dando, J.S., et al., "Notch/Delta4 interaction in human embryonic liver CD34+ CD38– cells: positive influence on BFU-E production and LTC-IC potential maintenance," Stem Cells 23(4):550-560, John Wiley & Sons, Inc., United States (2005).
Deisenhofer, J., "Crystallographic refinement and atomic models of a human Fc fragment and its complex with fragment B of protein A from *Staphylococcus aureus* at 2.9- and 2.8-A resolution," Biochemistry 20(9)2361-2370, American Chemical Society, United States (1981).
Deonarain, M.P., et al., "Antibodies Targeting Cancer Stem Cells: A New Paradigm in Immunotherapy?," mAbs 1(1):12-25,Taylor & Francis, United States (2009).
Dixit, R., "Cardiovascular Safety of Biologics: Challenges and Opportunities," Mediaimmune, Safety Pharmacology Society, Annular Meeting Speakers Presentations (Oct. 3, 2012).
Dontu, G., et al., "Role of Notch Signaling in Cell-Fate Determination of Human Mammary Stem/progenitor Cells," Breast Cancer Research 6(6):R605-R615, BioMed Central, England (2004).
Dorsch, M., et al., "Ectopic expression of Delta4 impairs hematopoietic development and leads to lymphoproliferative disease," Blood 100(6):2046-2055, American Society of Hematology, United States (2002).
Dreher, M.L., et al., "Colony assays for antibody fragments expressed in bacteria," Journal of Immunological Methods 139(2)197-205, Elsevier Science, United States (1991).
Duarte, A., et al., "Dosage-sensitive requirement for mouse Dll4 in artery development," Genes & Development 18(20)2474-2478, Cold Spring Harbor Laboratory Press, United States (2004).
Dupont, J. "Anti-Angiogenic Agents and Cardiovascular Effects: Implications for Clinical Development in Cancer," presentation given in Barcelona, Spain on Nov. 4, 2011, 16 pages.
Dupont, J., et al., "A Phase 1b Study of Anti-DLL4 (Delta-Like Ligand 4) Antibody Demcizumab (DEM) with Pemetrexed (PEM) and Carboplatin (CARBO) in Patients with 1st-Line Non-Squamous NSCLC," 2015 European Lung Cancer Conference (ELCC), Geneva, Switzerland, Apr. 15-18, Abstract 114, 2 pages (2015).
Ellisen, L.W., et al., "TAN-1, The Human Homolog of the *Drosophila*NotchGene, Is Broken by Chromosomal Translocations in T Lymphoblastic Neoplasms," Cell 66(4):649-661, Elsevier Science, United States (1991).
Engin,F., et al., "Dimorphic effects of Notch signaling in bone homeostasis," Nature Medicine 14(3):299-305, Nature Publishing Group, United States (2008).
English language translation of Oishi, H., et al., "Novel therapeutic strategy for pancreatic cancer targeting Notch signaling pathway," Proceedings of the Japanese Cancer Association 65:311-312, Japan (2006).
English language translation of "Tumor-angiogenesis suppression therapy targeting the Notch signaling pathway," Suizo (Pancreas) 21(3):249, Japan (2006).
Eppstein, D.A., et al., "Biological activity of liposome-encapsulated murine interferon gamma is mediated by a cell membrane receptor," Proceedings of the National Academy of Sciences 82(11):3688-3692, National Academy of Sciences, United States (1985).
European Search Report for EP Application No. EP10824244.7, Munich, Germany, dated Feb. 18, 2013, 6 pages.
Farnie, G. and Clarke, R.B., "Mammary stem cells and breast cancer—role of Notch signalling," Stem Cell Reviews and Reports 3(2):169-175, Humana Press, United States (2007).
Farnie, G., et al., "Novel cell culture technique for primary ductal carcinoma in situ: role of Notch and epidermal growth factor receptor signaling pathways," Journal of the National Cancer Institute 99(8):616-627, Oxford University Press, United Kingdom (2007).
Fischer, M., et al., "Anti-DLL4 Inhibits Growth and Reduces Tumor-Initiating Cell Frequency in Colorectal Tumors with Oncogenic KRAS Mutations," Cancer Research 71(5):1520-1525, American Association for Cancer Research, United States (2011).

(56) References Cited

OTHER PUBLICATIONS

Fleming, R.J., et al., "The Notch receptor and its ligands," Trends in Cell Biology 7(11):437-441, Elsevier Science Ltd., The Netherlands (1997).

Fre, S., et al., "Notch Signals Control the Fate of Immature Progenitor Cells in the Intestine," Nature 435(7044):964-968, Nature Publishing Group, United States (2005).

Fung, E., et al., "Delta-like 4 induces notch signaling in macrophages: implications for inflammation," Circulation 115(23):2948-2956, American Heart Association, Inc., United States (2007).

Gagnon, M,L., et al., "Identification of a natural soluble neuropilin-1 that binds vascular endothelial growth factor: In vivo expression and antitumor activity," Proceedings of the National Academy of Sciences 97(6):2573-2578, National Academy of Sciences, United States (2000).

Gale, N.W., et al., "Haploinsufficiency of Delta-like 4 Ligand Results in Embryonic Lethality due to Major Defects in arterial and Vascular Development," Proceedings of the National Academy of Sciences 101(45):15949-15954, National Academy of Sciences, United States (2004).

Gallahan, D., et al., "A new common integration region (int-3) for mouse mammary tumor virus on mouse chromosome 17," Journal of Virology 61(1):218-220, American Society for Microbiology, United States (1987).

Gallahan, D., et al., "Expression of a TruncatedInt3Gene in Developing Secretory Mammary Epithelium Specifically Retards Lobular Differentiation Resulting in Tumorigenesis," Cancer Research 56(8):1775-1785, American Association for Cancer Research, United States (1996).

Garber, K., "Notch emerges as new cancer drug target," Journal of the National Cancer Institute 99(17):1284-1285, Oxford University Press, United States (2007).

Gracian, A.C., et al., "A phase 1b study of the anticancer stem cell agent demcizumab (DEM) and gemcitabine (GEM) with or without paclitaxel protein bound particles (nab-paclitaxel) in patients with pancreatic cancer," 2014 Gastrointestinal Cancers Symposium, Abstract 279, 2 pages (2014).

Gray-Schopfer, V.C., et al., "The Role of B-RAF in Melanoma," Cancer Metastasis Reviews 24(1):165-183, Springer Science + Business Media, Inc., Netherlands (2005).

Gridley, T., "Notch Signaling During Vascular Development," Proceedings of the National Academy of Sciences 98(10):5377-5378, National Academy of Sciences, United States (2001).

Gridley, T. "Notch signaling in vascular development and physiology," Development 134(15):2709-2718, (2007).

Gronberg, B.H., et al., "Phase III Study by the Norwegian Lung Cancer Study Group: Pemetrexed Plus Carboplatin Compared with Gemcitabine Plus Carboplatin as First-line Chemotherapy in Advanced Non-small-cell Lung Cancer," Journal of Clinical Oncology 27(19):3217-3224, American Society of Clinical Oncology, United States (2009).

Gruber, M., et al., "Efficient Tumor Cell Lysis Mediated by a Bispecific Single Chain Antibody Expressed in*Escherichia coli*," The Journal of Immunology 152(11):5368-5374, The American Association of Immunologists, Inc., United States (1994).

Gurney, A. and Hoey, T., "Anti-DLL4, a Cancer Therapeutic with Multiple Mechanisms of Action," Vascular Cell 3, 4 pages, BioMed Central, United States (2011).

Hainaud, P., et al., "The role of the vascular endothelial growth factor-Delta-like 4 ligand/Notch4-ephrin B2 cascade in tumor vessel remodeling and endothelial cell functions," Cancer Research 66(17):8501-8510, American Association for Cancer Research, United States (2006).

Hallahan, A.R., et al., "The SmoA1 Mouse Model Reveals that Notch Signaling is Critical for the Growth and Survival of Sonic Hedgehog-Induced Medulloblastomas," Cancer Research 64(21):7794-7800, American Association for Cancer Research, United States (2004).

Han, W., et al., "A soluble form of human Delta-like-1 inhibits differentiation of hematopoietic progenitor cells," Blood 95(5):1616-1625, The American Society of Hematology, United States (2000).

Harlow, E. and Lane, D., eds., "Immunoassays, in Antibodies: A Laboratory Manual," 14:553-612, Cold Spring Harbor Laboratory, United States (1988).

Harper, J.A., et al., "Notch Signaling in Development and Disease," Clinical Genetics 64(6):461-472, Blackwell Publishing, United States (2003).

Harrington, L.S., et al., "Regulation of multiple angiogenic pathways by Dll4 and Notch in human umbilical vein endothelial cells," Microvascular Research 75(2):144-154, Elsevier Science, United States (2008).

Harris, W.J., "Production of Humanized Monoclonal Antibodies for in vivo Imaging and Therapy," Biochemical Society Transactions 23(4)1035-1038, Portland Press on the Behalf of the Biochemical Society, England (1995).

Hawkins, R.E., et al., "Selection of phage antibodies by binding affinity. Mimicking affinity maturation," Journal of Molecular Biology 226(3):889-896, Elsevier Science, United States (1992).

Hellström, M., et al., "Dll4 signalling through Notch1 regulates formation of tip cells during angiogenesis," Nature 445(7129):776-780, Nature Publishing Group, United States (2007).

Henning, K., et al., "mNotch1 signaling and erythropoietin cooperate in erythroid differentiation of multipotent progenitor cells and upregulate beta-globin," Experimental Hematology 35(9):1321-1332, Elsevier Science, United States (2007).

Hermentin, P. and Seiler, F.R., "Investigations with Monoclonal Antibody Drug (Anthracycline) Conjugates," Behring Institute Research Communications 82:197-215, Behringwerke Ag, Germany (1988).

Hicks, C., et al., "A Secreted Delta1-Fc Fusion Protein Functions Both as an Activator and Inhibitor of Notch1 Signaling," Journal of Neuroscience Research 68(6):655-657, Wiley Interscience, United States (2002).

Hidalgo, M., et al., "A Phase 1b Study of the Anti-Cancer Stem Cell Agent Demcizumab (DEM, anti-DLL4) and Gemcitabine (GEM) with or without Nab-Paclitaxvel in Patients with Pancreatic Cancer," European Society for Medical Oncology 2014 Congress, Sep. 17 and Sep. 28, Poster 616PD, 1 page (2014).

Hidalgo, M., et al., "A Phase 1b Study of the Anti-Cancer Stem Cell Agent Demcizumab (DEM, Anti-DLL4) and Gemcitabine (GEM) with or without Paclitaxel Protein Bound Particles (Nab-Paclitaxel) in pts with Pancreatic Cancer," 2015 ASCO Annual Meeting, Abstract 4118, 3 pages (2015).

Hidalgo, M., et al., "Pre-Clinical and Clinical Activity of Anti-DLL4 (Demcizumab) in Combination with Gemcitabine Plus nab-Paclitaxel in Pancreatic Cancer," 26th EORTC-NCI-AACR Symposium on Molecular Targets and Cancer Therapeutics Preclinical Models Poster Session, Abstract 166, 2 pages (Nov. 2014).

Hoey, T., et al., "DLL4 blockade inhibits tumor growth and reduces tumor-initiating cell frequency," Cell Stem Cell 5(2):168-177, Elsevier Science, United States (2009).

Hofmann, J.J. and Iruela-Arispe, M.L., "Notch signaling in blood vessels: who is talking to whom about what?," Circulation Research 100(11):1556-1568, American Heart Association, Inc., United States (2007).

Holash, J., et al., "Inhibitors of growth factor receptors, signaling pathways and angiogenesis as therapeutic molecular agents," Cancer Metastasis Rev 25:243-252, Dordrecht, Netherlands (2006).

Holash, J., et al., "VEGF-Trap: A VEGF Blocker with Potent Antitumor Effects," Proceedings of the National Academy of Sciences USA 99(17):11393-11398, National Academy of Sciences, United States (2002).

Holm, P., et al., "Functional Mapping and Single Chain Construction of the Anti-Cytokeratin 8 Monoclonal Antibody TS1," Molecular Immunology 44(6):1075-1084, Pergamon Press, England (2007).

Hoogenboom, H.R. and Winter, G., "By-Passing Immunisation. Human Antibodies from Synthetic Repertoires of Germline VH Gene Segments Rearranged in vitro," Journal of Molecular Biology 227(2):381-388, Elsevier, England (1992).

(56) References Cited

OTHER PUBLICATIONS

Hope, K.J., et al., "Acute myeloid leukemia originates from a hierarchy of leukemic stem cell classes that differ in selfrenewal capacity," Nature Immunology 5(7):738-743, Nature Publishing Group,United States (2004).
Hopfer. O.,et al., "The Notch Pathway in Ovarian Carcinomas and Adenomas," British Journal of Cancer 93(6):709-718, Nature Publishing Group on behalf of Cancer Research UK, England (2005).
Humphreys, D.P., et al., "Formation of dimeric Fabs in *Escherichia coli*: effect of hinge size and isotype, presence of interchain disulphide bond, Fab' expression levels, tail piece sequences and growth conditions," Journal of Immunological Methods 209(2):193-202, Elsevier Science, Netherlands (1997).
Hurle, M.R. and Gross, M., "Protein engineering techniques for antibody humanization," Current Opinion in Biotechnology 5(4):428-433, (1994).
Hurwitz, H.I., et al., "Phase I Trial of Pazopanib in Patients with Advanced Cancer," Clinical Cancer Research 15(12):4220-4227, American Association for Cancer Research, United States (2009).
Hwang, K.J., et al., "Hepatic uptake and degradation of unilamellar sphingomyelin/cholesterol liposomes: a kinetic study," Proceedings of the National Academy of Sciences 77(7):4030-4034, National Academy of Sciences, United States (1980).
International Preliminary Report on Patentability and Written Opinion for International Application No. PCT/US2010/53064, International Searching Authority, dated Feb. 14, 2011, 7 pages.
International Preliminary Report on Patentability for International Application No. PCT/US2013/065015, The International Bureau of WIPO, Switzerland, dated Apr. 22, 2014, 17 pages.
International Search Report for International Application No. PCT/US16/53316, ISA/US, Alexandria, Virginia, dated Feb. 21, 2017, 7 pages.
International Search Report for International Application No. PCT/US2010/53064, dated Feb. 14, 2011, 3 Pages.
International Search Report for International Application No. PCT/US2015/024251, ISA/US, Alexandria, Virginia, United States, dated Jul. 16, 2015, 4 pages.
International Search Report for International Patent Application No. PCT/US11/60773, International Searching Authority, Alexandria, Virginia, United States, dated Mar. 26, 2012, 3 pages.
International Search Report for International Patent Application No. PCT/US2007/020889, United States Patent and Trademark Office, United States, dated Apr. 9, 2008, 5 pages.
International Search Report with the Written Opinion of the International Searching Authority for International application No. PCT/US10/32625, United States Patent and Trademark Office, United States, dated Dec. 17, 2010, 11 pages.
International Search Report with the Written Opinion of the International Searching Authority for International application No. PCT/US12/56886, United States Patent and Trademark Office, United States, dated Feb. 28, 2013, 8 pages.
International Search Report with the Written Opinion of the International Searching Authority for International application No. PCT/US15/58327, United States Patent and Trademark Office, United States, dated May 19, 2016, 12 pages.
International Search Report with Written Opinion for International Application No. PCT/US2010/58511, International Searching Authority, United States, dated Mar. 3, 2011, 9 pages.
Ishiko, E., et al., "Notch signals inhibit the development of erythroid/megakaryocytic cells by suppressing GATA-1 activity through the induction of HES1," The Journal of Biological Chemistry 280(6):4929-4939, American Society for Biochemistry and Molecular Biology, United States (2005).
Iso, T., et al., "Notch Signaling in Vascular Development," Arteriosclerosis, Thrombosis, and Vascular Biology 23(4):543-553, American Heart Association, Inc., United States (2003).
Izzedine, H., et al., "Management of Hypertension in Angiogenesis Inhibitor-Treated Patients," Annals of Oncology 20(5):807-815, Oxford University Press, England (2009).

Jackson, J.R., et al., "In vitro antibody maturation. Improvement of a high affinity, neutralizing antibody against IL-1 beta," The Journal of Immunology 154(7):3310-3319, The American Association of Immunologists, Inc., United States (1995).
Janda, C.Y., "Structural Basis of Wnt Recognition by Frizzled," Science 337(6090):59-64, American Association for the Advancement of Science, United States (2012).
Janeway, Jr., et al., "Immunobiology, The Immune System in Health and Disease," Edition 4:579-581, Current Biology Publications (1999).
Jang, Y.J., et al., "The Structural Basis for DNA Binding by an Anti-DNA Autoantibody," Molecular Immunology 35(18):1207-1217, Pergamon Press, England (1998).
Jarriault, S., et al., "Signalling Downstream of Activated Mammalian Notch," Nature 377(6547):355-358, Nature Publishing Group, United States (1995).
Jeffries, S. and Capobianco, A.J., "Neoplastic transformation by Notch requires nuclear localization," Molecular and Cellular Biology 20(11):3928-3941, American Society for Microbiology, United States (2000).
Jhappan, C., et al., "Expression of an Activated Notch-Related int-3 Transgene Interferes with Cell Differentiation and Induces Neoplastic Transformation in Mammary and Salivary Glands," Genes & Development 6(3):345-355, Cold Spring Harbor Laboratory Press, United States (1992).
Jimeno, A., et al., "Phase 1 study of REGN421 (R)/SAR153192, a fully-human delta-like ligand 4 (DII4) monoclonal antibody (mAb), in patients with advanced solid tumors," ASCO University 2013 ASCO Annual Meeting accessed at http://meetinglibrary.asco.org/content/113836-132, 2 pages.
Jones, P.T., et al., "Replacing the Complementarity-Determining Regions in a Human Antibody with those from a Mouse," Nature 321(6069):522-525, Nature Publishing Group, England (1986).
Kim, E.S., et al., "Potent VEGF blockade causes regression of coopted vessels in a model of neuroblastoma," Proceedings of the National Academy of Sciences 99(17):11399-11404, National Academy of Sciences, United States (2002).
Kingsman, A.J., et al., "Replication in *Saccharomyces cerevisiae* of Plasmid pBR313 Carrying DNA from the Yeast Trpl Region," Gene 7(2):141-152, Elsevier/North-Holland Biomedical Press, Netherlands (1979).
Kobayashi, H., et al., "Tryptophan H33 Plays an Important Role in Pyrimidine (6-4) Pyrimidone Photoproduct Binding by a High-Affinity Antibody," Protein Engineering Design and Selection 12(10):879-884, Oxford University Press, United States (1999).
Kopper, L. and Hajdu, M., "Tumor Stem Cells," Pathology and Oncology Research 10(2):69-73, Aranyl Lajos Foundation, Hungary (2004).
Kostelny, S.A., et al., "Formation of a Bispecific Antibody by the Use of Leucine Zippers," The Journal of Immunology 148(5):1547-1553, American Association of Immunologists, United States (1992).
Krebs, L.T., et al., "Haploinsufficient Lethality and Formation of Arteriovenous Malformations in Notch Pathway Mutants" Genes & Development 18(20):2469-2473, Cold Spring Harbor Laboratory Press, United States (2004).
Krebs, L.T., et al., "Notch Signaling is Essential for Vascular Morphogenesis in Mice," Genes & Development 14(11):1343-1352, Cold Spring Harbor Laboratory Press, United States (2000).
Kuo, C.J., et al., "Comparative evaluation of the antitumor activity of antiangiogenic proteins delivered by gene transfer," Proceedings of the National Academy of Sciences 98(8):4605-4610, National Academy of Sciences, United States (2001).
Lapidot, T., et al., "A Cell Initiating Human Acute Myeloid Leukaemia After Transplantation Into SCID Mice," Nature 367(6464):645-648, Nature Publishing Group, United States (1994).
Lauret, E., et al., "Membrane-Bound Delta-4 Notch Ligand Reduces the Proliferative Activity of Primitive Human Hematopoietic CD34+CD38low Cells while Maintaining their LTC-IC Potential," Leukemia 18(4):788-797, Nature Publishing Group, United States (2006).

(56) References Cited

OTHER PUBLICATIONS

Lazar, E., et al., "Transforming Growth Factor α: Mutation of Aspartic Acid 47 and Leucine 48 Results in Different Biological Activities," Molecular and Cellular Biology 8(3):1247-1252, American Society for Microbiology, United States (1988).

Lee, H.S., et al., "Generation and characterization of a novel single-gene-encoded single-chain immunoglobulin molecule with antigen binding activity and effector functions," Molecular Immunology 36(1):61-71, Elsevier Science Ltd., Netherlands (1999).

Leethanakul, C., et al., "Distinct Pattern of Expression of Differentiation and Growth-Related Genes in Squamous Cell Carcinomas of the Head and Neck Revealed by the Use of Laser Capture Microdissection and cDNA Arrays," Oncogene 19(28):3220-3224, Nature Publishing Group, United States (2000).

Lenihan, D.J., "How is cardiac toxicity defined and what impact does this have on cancer outcome or drug development," PowerPoint Presentation from the DIA Meeting, 42 slides (2011).

Leong, K.G. and Karsan, A., "Recent Insights into the Role of Notch Signaling in Tumorigenesis," Blood 107(6):2223-2233, The American Society of Hematology, United States (2006).

Li, J.L. and Harris A.L., "Notch Signaling from Tumor Cells: A New Mechanism of Angiogenesis," Cancer Cell 8(1):pp. 1-3, Cell Press, United States (2005).

Li, X., et al., "Notch3 Signaling is Required for the Development of Pulmonary Arterial Hypertension," Nature Medicine 15(11):1289-1297, Nature Publishing Company, United States (2009).

Lievre, A., et al., "KRAS Mutation Status Is Predictive of Response to Cetuximab Therapy in Colorectal Cancer," Cancer Research 66(8):3992-3995, American Association for Cancer Research, United States (2006).

Limbourg, A., et al., "Notch ligand Delta-like 1 is essential for postnatal arteriogenesis," Circulation Research 100(3):363-371, American Heart Association, Inc., United States (2007).

Liu, S., et al., "Mammary stem cells, self-renewal pathways, and carcinogenesis," Breast Cancer Research 7(3):86-95, BioMed Central, England (2005).

Liu, Z.J., et al., "Inhibition of endothelial cell proliferation by Notch 1 signaling is mediated by repressing MAPK and P14K/Akt pathways and requires MAML1," Federation of American Societies for Experimental Biology 20:E201-E210, American Society for Experimental Biology, United States (2006).

Liu, Z.J., et al., "Regulation of Notch1 and Dll4 by vascular endothelial growth factor in arterial endothelial cells: implications for modulating arteriogenesis and angiogenesis," Molecular and Cellular Biology 23(1):14-25, American Society for Microbiology, United States (2003).

Lobov, I.B., et al., "Delta-like ligand 4 (Dll4) is induced by VEGF as a negative regulator of angiogenic sprouting," Proceedings of the National Academy of Sciences 104(9)3219-3224, National Academy of Sciences, United States (2007).

Lu, K.V., and Bergers, G., "Mechanisms of evasive resistance to anti-VEGF therapy in glioblastoma," CNS Oncology 2(1):49-65, Future Medicine, Inc., United States (2013).

Luca, V.C., et al., "Structural basis for Notch1 engagement of Delta-like 4," Science, 347(6224):847-853, American Association for the Advancement of Science, United States (2015).

MacCallum, R.M., et al., "Antibody-Antigen Interactions: Contact Analysis and Binding Site Topography," Journal of Molecular Biology 262(5):732-745, Elsevier, England (1996).

Maeda, H., et al., "Construction of Reshaped Human Antibodies with HIV-Neutralizing Activity," Human Antibodies and Hybridomas 2(3):124-134, Butterworth-Heinemann, United Kingdom (1991).

Mailhos, C., et al., "Delta4, an Endothelial Specific Notch Ligand Expressed at Sites of Physiological and Tumor Angiogenesis," Differentiation 69:135-144, Elsevier, England (2001).

Marks, J.D., et al., "By-Passing Immunization: Building High Affinity Human Antibodies by Chain Shuffling," Biotechnology 10(7):779-783, Nature Publishing Company, United States (1992).

Marks, J.D., et al., "By-passing immunization. Human Antibodies from V-Gene Libraries Displayed on Phage," Journal of Molecular Biology 222(3):581-597, Academic Press Limited, United States (1991).

Mazella, J., et al., "Expression of Delta-like protein 4 in the human endometrium," Endocrinology 149(1)15-19, Association for the Study of Internal Secretions, United States (2008).

McAuliffe, S.M., et al., "Targeting Notch, a Key Pathway for Ovarian Cancer Stem Cells, Sensitizes Tumors to Platinum Therapy," Proceedings of the National Academy of Sciences USA 109(43):E2939-E2948, National Academy of Sciences, United States (2012) with Supporting Information.

McKeage, M., et al., "A Phase 1b Study of Demcizumab plus Pemetrexed and Carboplatin in Patients with 1st line Non-Squamous Non-Small Cell Lung Cancer (NSCLC)," 24th EORTC-NCI-AACR Symposium on Molecular Targets and Cancer Therapeutics, Nov. 6-9, 2012, Poster (2012), 9 pages.

McKeage, M., et al., "A Phase 1b study of demcizumab (DEM, anti-DLL4) plus pemetrexed and carboplatin in patients with first line stage IIIb/IV non-squamous non-small cell lung cancer," Proceedings of the AACR-NCI-EORTC International Conference on Molecular Targets and Cancer Therapeutics, Oct. 19-23, 2013, Abstract A71, 2 pages (2013).

McKeage, M., et al., "Phase 1b Study of Demcizumab plus Pemetrexed and Carboplatin in Patients with 1st line Non-Small Cell Lung Cancer (NSCLC)," AACR-NCI-EORTC International Conference on Molecular Targets and Cancer Therapeutics, Oct. 19-23, 2013, Poster (2013), 8 pages.

McKeage, M.J., et al., "A phase 1b study of the anticancer stem cell agent demcizumab (DEM), pemetrexed (PEM), and carboplatin (CARBO) in pts with first-line nonsquamous NSCLC," 2014 ASCO Annual Meeting, Abstract 2544, 2 pages (2014).

McKeage, M.J., et al., "A Phase 1b Study of the Anti-Cancer Stem Cell Agent Demcizumab (DEM), Pemetrexed (PEM) and Carboplatin (CARBO) inPatients with 1st Line Non-Squamous Non-Small Cell Lung Cancer (NSCLC)," 2015 ASCO Annual Meeting, Abstract 8045, 2 pages (2015).

Merchant, A.M., et al., "An Efficient Route to Human Bispecific IgG," Nature Biotechnology 16(7):677-681, Nature Publishing Group, United States (1998).

Miele, L. and Osborne, B., "Arbiter of Differentiation and Death: Notch Signaling Meets Apoptosis," Journal of Cellular Physiology 181(3):393-409, Wiley-Liss, Inc., United States (1999).

Miele, L., "Notch Signaling," Clinical Cancer Research 12:1074-1077, The American Association for Cancer Research, United States (2006).

Milano, J., et al., "Modulation of Notch Processing by D-Secretase Inhibitors Causes Intestinal Goblet Cell Metaplasia and Induction of Genes Known to Specify Gut Secretory Lineage Differentiation," Toxicological Sciences 82(1):341-358, Oxford University Press, United States (2004).

Milstein, C. and Cuello, A.C., "Hybrid Hybridomas and Their Use in Immunohistochemistry," Nature 305 (5934):537-540, Nature Publishing Group, England (1983).

Morimoto, K., and Inouye K., "Single-step purification of F(ab')2 mu fragments of mouse monoclonal antibodies (immunoglobulins G1) by hydrophobic interaction high-performance liquid chromatography using TSKgel Phenyl-5PW," Journal of Biochemical and Biophysical Methods 24(1-2):107-117, Elsevier/North-Holland Biomedical Press, Netherlands (1993).

Morrison, S.J., et al., "Hematopoietic Stem Cells: Challenges to Expectations," Current Opinion in Immunology 9(2):216-221, Elsevier Science, United States (1997).

Morrison, S.J.,et al., "Regulatory Mechanisms in Stem Cell Biology," Cell 88(3):287-298, Elsevier Science, United States (1997).

Morrison, S.J.,et al., "The Biology of Hematopoietic Stem Cells," Annual Review of Cell and Developmental Biology 11:35-71, Annual Reviews, United States (1995).

Morrison, S.J.,et al., "Transient Notch activation initiates an irreversible switch from neurogenesis to gliogenesis by neural crest stem cells," Cell 101(5):499-510, Elsevier Science, United States (2000).

(56) References Cited

OTHER PUBLICATIONS

Morrison, S.L., et al., "Chimeric Human Antibody Molecules: Mouse Antigen-Binding Domains with Human Constant Region Domains," Proceedings of the National Academy of Sciences USA 81(21):6851-6855, National Academy of Sciences, United States (1984).

Nam, Y., et al., "Notch Signaling as a Therapeutic Target," Current Opinion in Chemical Biology 6(4):501-509, Elsevier Science, United States (2002).

NCT00744562, "A Phase 1 Dose Escalation Study of OMP-21M18 in Subjects With Solid Tumors," ClinicalTrials.gov archive, accessed at http://clinicaltrials.gov/archive/NCT00744562/2008_10_06, accessed on Feb. 2, 2012, 4 pages.

NCT01189929, "A Phase 1b Study of Gemcitabine Plus OMP-21M18 as 1st-line Treatment in Subjects With Locally Advanced or Metastatic Pancreatic Cancer" as updated on Aug. 26, 2010, ClinicalTrials.gov archive, accessed at https://clinicaltrials.gov/archives/NCT01189929/2010_08_26, accessed on Apr. 20, 2015, 5 pages.

NCT01189929, "A Phase 1b Study of Gemcitabine Plus OMP-21M18 as 1st-line Treatment in Subjects With Locally Advanced or Metastatic Pancreatic Cancer" as updated on Dec. 15, 2011, ClinicalTrials.gov archive, accessed at https://clinicaltrials.gov/archives/NCT01189929/2011_12_15, accessed on Apr. 20, 2015, 5 pages.

NCT01189968, "A Phase 1b Study of Carboplatin and Pemetrexed Plus OMP-21M18 as 1st-line Treatment in Subjects with Non-Squamous Non-Small Cell Lung Cancer" as updated on Aug. 26, 2010, ClinicalTrials.gov archive, accessed at https://clinicaltrials.gov/archive/NCT01189968/2010_08_26, accessed on Apr. 20, 2015, 5 pages.

NCT01189968, "A Phase 1b Study of Carboplatin and Pemetrexed Plus OMP-21M18 as 1st-line Treatment in Subjects with Non-Squamous Non-Small Cell Lung Cancer" as updated on Dec. 15, 2011, ClinicalTrials.gov archive, accessed at https://clinicaltrials.gov/archive/NCT01189968/2011_12_15, accessed on Apr. 20, 2015, 5 pages.

NCT01189968, "A Phase Ib Study of Carboplatin and Permetrexed Plus OMP-21M18 as 1st-line Treatment in Subject With Non-Squamous Non-Small Cell Lung Cancer," ClinicalTrials.gov archive, accessed at http://clinicaltrials.gov/archive/NCT01189968/2010_10_28, accessed on Feb. 7, 2012, 4 pages.

Nickoloff, B.J., et al., "Notch Signaling as a Therapeutic Target in Cancer: a New Approach to the Development of Cell Fate Modifying Agents," Oncogene 22(42):6598-6608, Nature Publishing Group, England (2003).

Nimmagadda, S., et al., "Expression pattern of Dll4 during chick embryogenesis," Histochem Cell Biol 128(2):147-152, Springer-Verlag, Germany (2007).

Noguera, I., et al., "Delta-like ligand 4 (Dll4) is critical for tumor growth and angiogenesis," Proceedings of the Annual Meeting of American Association for Cancer Research 47:1342, American Association for Cancer Research, United States (2006).

Noguera, I., et al., "Expression of Delta-like 4 (Dll4) ligand in mouse tumor models," Proceedings of the Annual Meeting of the American Association for Cancer Research 46(Suppl5):1104, American Association for CancerResearch, United States (2005).

Noguera-Troise, I., et al., "Blockade of Dll4 inhibits tumour growth by promoting non-productive angiogenesis," Nature 444(7122):1032-1037, Nature Publishing Group, United States (2006).

Nohaile, M.J., et al., "Altering dimerization specificity by changes in surface electrostatics," Proceedings of the National Academy of Sciences 98(6):3109-3114, National Academy of Sciences, United States (2001).

Novotný, J. and Haber, E., "Structural invariants of antigen binding: comparison of immunoglobulin VL-VH and VL-VL domain dimers," Proceedings of the National Academy of Sciences 82(14):4592-4596, National Academy of Sciences, United States (1985).

Office Action dated Apr. 20, 2016, in U.S. Appl. No. 14/498,602, Stagg, R.J., et al., filed Sep. 26, 2014.

Office Action dated Dec. 16, 2015, in U.S. Appl. No. 14/498,602, Stagg, R.J., et al., filed Sep. 26, 2014.

Oie, E., et al., "Activation of Notch signaling in cardiomyocytes during post-infarction remodeling," Scandinavian Cardiovascular Journal 44(6):359-366, Informa Healthcare, England (2010).

Oishi, H., et al., "Novel therapeutic strategy for pancreatic cancer targeting Notch signaling pathway," Proceedings of the Japanese Cancer Association 65:311-312, (2006).

OncoMed Pharmaceuticals, Press Release, "Clinical Cancer Research Publishes OncoMed Data Demonstrating Anti-Cancer Activity for Anti-DLL4 (Demcizumab) in Pancreatic Cancer," Sep. 6, 2012, 2 pages.

OncoMed Pharmaceuticals Press Release, "OncoMed and Lilly Enter Clinical Supply Agreement to Evaluate the Combination of Demcizumab and Alimta(R) (pemetrexed for injection) in Lung Cancer," Apr. 2, 2015, 4 pages.

OncoMed Pharmaceuticals, Press Release, "OncoMed Announces Abstracts Accepted at the 2014 ASCO Annual Meeting," Apr. 23, 2014, 2 pages.

OncoMed Pharmaceuticals Press Release, "OncoMed Announces Abstracts Accepted for Presentation at the 2015 ASCO Annual Meeting," Apr. 21, 2015, 2 pages.

OncoMed Pharmaceuticals, Press Release, "OncoMed Anti-Cancer Stem Cell Antibody OMP-21M18 Demonstrates Potent Activity in Preclinical Studies Against Human Colon Cancer Tumors Regardless of KRAS Mutation Status," Mar. 1, 2011, 3 pages.

OncoMed Pharmaceuticals, Press Release, "OncoMed's Demcizumab Phase 1b Clinical Trials Show Encouraging Safety and Anti-Tumor Activity at ESMO," Sep. 28, 2014, 3 pages.

OncoMed Pharmaceuticals Press Release, "OncoMed Doses First Patient in Phase 1 Clinical Trial of Novel Anti-DLL4/VEGF Bispecific Antibody," Jan. 5, 2015, 2 pages.

OncoMed Pharmaceuticals Press Release, "OncoMed Highlights Immuno-Oncology Discoveries During 2015 Research & Development Day," Apr. 29, 2015, 3 pages.

OncoMed Pharmaceuticals Press Release, "OncoMed Initiates Dosing in Phase 2 Clinical Trial of Demcizumab for the Treatment of Non-Small Cell Lung Cancer," Feb. 4, 2015, 3 pages.

OncoMed Pharmaceuticals Press Release, "OncoMed Initiates Dosing in Randomized Phase 2 Clinical Trial of Demcizumab in Pancreatic Cancer Patients," Apr. 22, 2015, 3 pages.

OncoMed Pharmaceuticals, Press Release, "OncoMed Pharmaceuticals Announces Presentations of Anti-Notch2/3 and Demcizumab Clinical Data at EORTC-NCI-AACR Meeting," Nov. 9, 2012, 3 pages.

OncoMed Pharmaceuticals, Press Release, "OncoMed Pharmaceuticals Initiates Phase 1b/2 Clinical Trial of Demcizuman (Anti-DLL4) in Combination with Paclitaxel in Ovarian Cancer," Sep. 19, 2013, 3 pages.

OncoMed Pharmaceuticals Press Release, "OncoMed Pharmaceuticals Presents Data From Clinical Trials of Four Novel Anti-Cancer Stem Cell (Anti-CSC) Therapeutics at the AACR-NCI-EORTC International Conference on Molecular Targets and Cancer Therapeutics in Boston, Oct. 19-23, 2013," Oct. 21, 2013, 4 pages.

OncoMed Pharmaceuticals, Press Release, "OncoMed Pharmaceuticals Presents Data From Demcizumab Phase 1b Clinical Study in Pancreatic Cancer at the 2014 Gastrointestinal Cancers Symposium," Jan. 17, 2014, 3 pages.

OncoMed Pharmaceuticals Press Release, "OncoMed Pharmaceuticals Recaps New Data Presented at AACR," Apr. 3, 2012, 2 pages.

OncoMed Pharmaceuticals Press Release, "OncoMed Pharmaceuticals to Present Data From Clinical Trials of Four Novel Anti-Cancer Stem Cell (Anti-CSC) Therapeutics in Five Posters at the AACR-NCI-EORTC International Conference on Molecular Targets and Cancer Therapeutics in Boston, Oct. 19-23, 2013," Oct. 14, 2013, 4 pages.

OncoMed Pharmaceuticals Press Release, "OncoMed Pharmaceuticals to Present Data from Two Clinical Programs in Advanced Pancreatic Cancer at the 2014 Gastrointestinal Cancers Symposium," Jan. 9, 2014, 2 pages.

(56) References Cited

OTHER PUBLICATIONS

OncoMed Pharmaceuticals Press Release, "OncoMed Pharmaceuticals to Review Key ASCO Data for Demcizumab and Tarextumab During Conference Call on Tuesday, Jun. 2, 2015," May 28, 2015, 2 pages.

OncoMed Pharmaceuticals, Press Release, "OncoMed Pharmaceuticals Updates Phase 1b Data for Demcizumab With Pemetrexed and Carboplatin in Patients With First-Line Stage IIIb/IV Non-Small Cell Lung Cancer at the AACR-NCO-EORTC International Conference on Molecular Targets and Cancer Therapeutics in Boston, Oct. 19-23, 2013," Oct. 20, 2013, 3 pages.

OncoMed Pharmaceuticals Press Release, "OncoMed Presents Data From Phase 1b Trial of Demcizumab in Pancreatic Cancer at the 2015 ASCO Annual Meeting," Jun. 1, 2015, 3 pages.

OncoMed Pharmaceuticals Press Release, "OncoMed Presents Data on Clinical and Preclinical Anti-Cancer Stem Cell Programs at American Association for Cancer Research Annual Meeting," Apr. 21, 2015, 3 pages.

OncoMed Pharmaceuticals, Press Release, "OncoMed Presents Data on Multiple Anti-Cancer Stem Cell Programs at American Association for Cancer Research Annual Meeting," Apr. 8, 2014, 4 pages.

OncoMed Pharmaceuticals Press Release, "OncoMed Presents Demcizumab Data From Phase 1b Clinical Trial in Non-Sman Cell Lung Cancer Patients at the European Lung Cancer Conference," Apr. 16, 2015, 3 pages.

OncoMed Pharmaceuticals Press Release, "OncoMed Presents New Clinical and Biomarker Data From Its Tarextumab and Demcizumab Clinical Trials at the EORTC-NCI-AACR Symposium," Nov. 21, 2014, 3 pages.

OncoMed Pharmaceuticals Press Release, "OncoMed Presents New Data in Six Anti-Cancer Stem Cell Programs at AACR," Apr. 9, 2013, 3 pages.

OncoMed Pharmaceuticals Press Release, "OncoMed Presents Updated Demcizumab Data in Non-Small Cell Lung Cancer at the 2015 ASCO Annual Meeting," Jun. 1, 2015, 3 pages.

OncoMed Pharmaceuticals Press Release, "OncoMed to Present Clinical and Preclinical Data at the 26th EORTC-NCI-AACR Symposium on Molecular Targets and Cancer Therapeutics Meeting," Oct. 30, 2014, 2 pages.

OncoMed Pharmaceuticals Press Release, "OncoMed to Present Clinical Data for Demcizumab at the European Lung Cancer Conference," Apr. 9, 2015, 2 pages.

OncoMed Pharmaceuticals Press Release, "OncoMed to Present Data From Three Clinical Studies at the 2014 ASCO Annual Meeting," May 14, 2014, 4 pages.

OncoMed Pharmaceuticals Press Release, "OncoMed to Present New and Emerging Data from Demcizumab (anti-DLL4, OMP-21M18) and Tarextumab (anti-Notch2/3, OMP-59R5) Clinical Studies at the European Society for Medical Oncology 2014 Congress," Sep. 17, 2014, 2 pages.

OncoMed Pharmaceuticals Press Release, "OncoMed to Present New Data in Six Anti-Cancer Stem Cell Programs at AACR," Apr. 2, 2013, 2 pages.

Parks, A.L., et al., "Structure-function analysis of delta trafficking, receptor binding and signaling in *Drosophila*," Genetics 174(4):1947-1961, Genetics Society of America, United States (2006).

Parr, C., et al., "The Possible Correlation of Notch-1 and Notch-2 with Clinical Outcome and Tumour Clinicopathological Parameters in Human Breast Cancer," International Journal of Molecular Medicine 14(5):779-786, Spandidos Publications, Greece (2004).

Patel, N.S., et al., "Up-regulation of delta-like 4 ligand in human tumor vasculature and the role of basal expression in endothelial cell function," Cancer Research 65(19):8690-8697, American Association for Cancer Research, United States (2005).

Paul, W.E., "Immunogenicity and Antigen Structure," in *Fundamental Immunology*, Third Edition, pp. 242, Raven Press, United States (1993).

Pear, W.S. and Aster, J.C., "T Cell Acute Lymphoblastic Leukemia/Lymphoma: a Human Cancer Commonly Associated with Aberrant NOTCH1 Signaling," Current Opinion in Hematology 11(6):426-433, Lippincott Williams & Wilkins, United States (2004).

Pear, W.S., et al., "Exclusive development of T cell neoplasms in mice transplanted with bone marrow expressing activated Notch alleles," The Journal of Experimental Medicine 183(5):2283-2291, the Rockefeller University Press, United States (1996).

Phng, L.K., et al., "Nrarp coordinates endothelial Notch and Wnt signaling to control vessel density in angiogenesis," Developmental Cell 16(1):70-82, Elsevier Science, United States (2009).

Pisano, C., et al., "Undersulfated, low-molecular-weight glycol-split heparin as an antiangiogenic VEGF antagonist," Glycobiology 15(2):1C-6C, Oxford University Press, England (2005).

Politi, K., et al., "Notch in Mammary Gland Development and Breast Cancer," Seminars in Cancer Biology 14(5):341-347, Academic Press, United States (2004).

Portolano, S., et al., "Lack of Promiscuity in Autoantigen-Specific H and L Chain Combinations as Revealed by Human H and L Chain 'Roulette'," The Journal of Immunology 150(3):880-887, The American Association of Immunologists, United States (1993).

Presta, L.G., et al., "Humanization of an antibody directed against IgE," The Journal of Immunology 151(5):2623-2632, The American Association of Immunologists, Inc., United States (1993).

Purow, B.W., et al., "Expression of Notch-1 and its Ligands, Delta-like-1 and Jagged-1, is Critical for Glioma Cell Survival and Proliferation," Cancer Research 65(6):2353-2363, American Association for Cancer Research, United States (2005).

Rae, F.K., et al., "Novel Association of a Diverse Range of Genes with Renal Cell Carcinoma as Identified by differential Display," International Journal of Cancer 88(5):726-732, John Wiley & Sons, Inc., United States (2000).

Rao, P.K., et al., "Isolation and characterization of the notch ligand delta4," Experimental Cell Research 260(2):379-386, Elsevier Science, United States (2000).

Rehman, A.O. and Wang, C-U, "Notch signaling in the regulation of tumor angiogenesis," Trends in Cell Biology 16(6):293-300, Elsevier Ltd., England (2006).

Response to Office Action dated Jan. 2, 2009, sent electronically on Jul. 2, 2009, in U.S. Appl. No. 11/607,780, Clarke, et al., filed Dec. 1, 2006.

Reya, T., et al., "Stem Cells, Cancer, and Cancer Stem Cells," Nature 414(6859):105-111, Nature Publishing Group, England (2001).

Ridgway, J., et al., "Inhibition of DII4 signalling inhibits tumour growth by deregulating angiogenesis," Nature 444(7122):1083-1087, Nature Publishing Group, United States (2006).

Riechmann, L., et al., "Reshaping Human Antibodies for Therapy," Nature 332(6162):323-327, Nature Publishing Group, United States (1988).

Robey, E., et al., "An Activated form of Notch Influences the Choice between CD4 and CD8 T Cell Lineages," Cell 87(3):483-492, Elsevier Science, United States (1996).

Rudikoff, S., et al., "Single Amino Acid Substitution Altering Antigen-Binding Specificity," Proceedings of the National Academy of Sciences USA 79(6):1979-1983, The National Academy of Sciences, United States (1982).

Sainson, R.C. and Harris, A.L., "Anti-DII4 therapy: can we block tumour growth by increasing angiogenesis?," 13(9):389-395, Elsevier Science, United States (2007).

Sal-Man, N. and Shai, Y., "Arginine mutations within a transmembrane domain of Tar, an *Escherichia coli* aspartate receptor, can drive homodimer dissociation and heterodimer association in vivo," Biochemical Journal 385(Pt1):29-36, Portland Press, United Kingdom (2005).

Scehnet, J.S., et al., "Inhibition of DII4-mediated signaling induces proliferation of immature vessels and results in poor tissue perfusion," Blood 109(11):4753-4760, American Society of Hematology, United Science (2007).

Schier, R., et al., "Identification of functional and structural amino-acid residues by parsimonious mutagenesis," Gene 169(2):147-155, Elsevier Science B.V., Netherlands (1996).

(56) References Cited

OTHER PUBLICATIONS

Schmidt, C., "Drug Makers Chase Cancer Stem Cells," Nature Biotechnology 26(4):366-367, Nature Publishing Group, United States (2008).

Shalaby, M.R., et al., "Development of Humanized Bispecific Antibodies Reactive with Cytotoxic Lymphocytes and Tumor Cells Overexpressing theHER2Protooncogene," The Journal of Experimental Medicine 175(1): 217-225, The Rockefeller University Press, United States (1992).

Shawber, C.J., et al., "Notch Signaling in Primary Endothelial Cells," Annals of the New York Academy of Sciences 995:162-170, New York Academy of Sciences, United States (2003).

Sheets, M.D., et al., "Efficient Construction of a Large Nonimmune Phage Antibody Library: The Production of High-affinity Human Single-chain Antibodies to Protein Antigens," Proceedings of the National Academy of Sciences 95(11):6157-6162, The National Academy of Sciences, Unites States (1998).

Shields, J.M., et al., "Lack of Extracellular Signal-Regulated Kinase Mitogen-Activated Protein Kinase Signaling Shows a New Type of Melanoma," Cancer Research 67(4):1502-1512, American Association for Cancer Research, United States (2007).

Shutter, J. R., et al., "Dll4, a Novel Notch Ligand Expressed in Arterial Endothelium," Genes & Development 14(11):1313-1318, Cold Spring Harbor Laboratory Press, United States (2000).

Sica, D.A., "Angiogenesis Inhibitors and Hypertension," US Cardiovascular Disease 79-80, Touch Briefings, United States (2007).

Siekmann, A.F. and Lawson, N.D., "Notch signalling limits angiogenic cell behaviour in developing zebrafish arteries," Nature 445(7129):781-784, Nature Publishing Group, United States (2007).

Siena, S., et al., "Biomarkers predicting clinical outcome of epidermal growth factor receptor-targeted therapy in metastatic colorectal cancer," Journal of the National Cancer Institute 101(19):1308-1324, Oxford University Press, England (2009).

Sims, M.J., et al., "A humanized CD18 antibody can block function without cell destruction," The Journal of Immunology 151(4):2296-2308, The American Association of Immunologists, United States (1993).

Skolnick, "From Genes to Protein Stucture and Function: Novel Applications of Computational Approaches in the Genomic Era," Trends in Biotechnology 18:34-39, Elsevier Science Publishers, London (2000).

Smith, D.C., et al., "A First-in-Human, Phase I Trial of the Anti-Dll4 Antibody (OMP-21M18) Targeting Cancer Stem Cells (CSCs) in Patients with Advanced Solid Tumors," http://www.oncomed.com/news/pr/studylposterfinalNov10.pdf, accessed Feb. 2, 2012, 1 page.

Smith, D.C., et al., "A Phase 1 Dose Escalation and Expansion Study of the Anticancer Stem Cell Agent Demcizumab (Anti-DLL4) in Patients with Previously Treated Solid Tumors," Clinical Cancer Research 20(24):6295-6303, American Association for Cancer Research, United States (2014).

Smith, D.C., et al., "A First-In-Human, Phase I Trial of the Anti-DLL4 Antibody (OMP-21M18) Targeting Cancer Stem Cells (CSC) in Patients with Advanced Solid Tumors," European Journal of Cancer Supplement 8(7):73, Abstract 222, 1 page (2010).

Smith, G.H., et al., "Constitutive Expression of a TruncatedINT3Gene in Mouse Mammary Epithelium Impairs Differentiation and Functional Development," Cell Growth & Differentiation 6(5):563-577, The American Association for Cancer Research, United States (1995).

Soriano J.V., et al., "Expression of an activated Notch4(int-3) oncoprotein disrupts morphogenesis and induces an invasive phenotype in mammary epithelial cellsin vitro," International Journal of Cancer 86(5):652-659, John Wiley & Sons, United States (2000).

Srivastava, M., et al., "Dual Targeting of Delta-Like Ligand 4 (DLL4) and Programmed Death 1 (PD1) Inhibits Tumor Growth and Generates Enhanced Long-Term Immunological Memory," 2015 AACR Annual Meeting, Apr. 19, Abstract 255, 1 page (2015).

Stinchcomb, D.T., et al., "Isolation and Characterisation of a Yeast Chromosomal Replicator," Nature 282(5734):39-43, Nature Publishing Group, England (1979).

Sugimoto, A. et al., "Delta-4 Notch Ligand Promotes Erythroid Differentiation of Human Umbilical Cord Blood CD34+ Cells," Experimental Hematology 34(4):424-432, Elsevier Science Inc, Netherlands (2006).

Sullivan, D.C. and Bicknell, R., "New molecular pathways in angiogenesis," British Journal of Cancer 89:228-231, Cancer Research UK, United Kingdom (2003).

Supplementary European Search Report issued in the corresponding European Patent Application No. 07838966, European Patent Office, Munich, Germany, dated Apr. 6, 2010.

Suresh, M.R., et al., "Bispecific Monoclonal Antibodies from Hybrid Hybridomas," Methods in Enzymology 121:210-228, Academic Press Inc., United States (1986).

Suzuki, T., et al., "Imbalanced Expression ofTAN-1and HumanNotch4in Endometrial Cancers," International Journal of Oncology 17(6):1131-1139, Spandidos Publications, Greece (2000).

Takeda, T. and Kohno, M., "Brain Natriuretic Peptide in Hypertension," Hypertension Research 18(4)259-286, Nature Publishing Group, England (1995).

Tannock, I.F. and Hill R.P., "Influence of Tumor Microenvironment," in *The Basic Science of Oncology*, pp. 357-358, McGraw-Hill, United States (1998).

Tavares, M.J., et al., "Inhibition of Vascular Endothelium by the Notch-Ligand Delta-4 Unveils a Novel Therapeutic Target," Abstract#1944, Poster Board Session: 115-11, Blood 102(11):3 pages, American Society of Hematology, United States (2003).

Tax, F.E., et al., "Sequence of C. elegans lag-2 Reveals a Cell-Signalling Domain Shared with Delta and Serrate of *Drosophila*," Nature 368(6467):150-154, The National Academy of Sciences, United States (1994).

Thelu, J., et al., "Notch Signalling is Linked to Epidermal Cell Differentiation Level in Basal Cell Carcinoma, Psoriasis and Wound Healing," BMC Dermatology 2(1):7, BioMed Central, England (2002).

Thurston, G., and Gale, N.W, "Vascular Endothelial Growth Factor and Other Signaling Pathways in Developmental and Pathologic Angiogenesis," International Journal of Hematology 80:7-20, The Japanese Society of Hematology, Japan (2004).

Thurston, G., et al., "The Delta paradox: DLL4 blockade leads to more tumour vessels but less tumour growth," Nature Reviews Cancer 7(5):327-331, Nature Publishing Group, United States (2007).

Ton, N.C. and Jayson, G.C., "Resistance to Anti-VEGF Agents," Current Pharmaceutical Design 10:51-64, Bentham Science Publishers Ltd., Netherlands (2004).

Traunecker, A., et al., "Bispecific single chain molecules (Janusins) target cytotoxic lymphocytes on HIV infected cells," The EMBO Journal 10(12):3655-3659, Oxford University Press, United Kingdom (1991).

Tutt, A., et al., "Trispecific F(ab')3 Derivatives that use Cooperative Signaling Via the TCR/CD3 Complex and CD2 to Activate and Redirect Resting Cytotoxic T Cells," The Journal of Immunology 147: 60-69, The American Association of Immunologists, United States (1991).

Unknown Author., "Tumor angiogenesis suppression therapy targeting the Notch signaling pathway," Suizo (Pancreas) 21(3):249, (2006).

Urlaub, G. and Chasin, L.A., "Isolation of Chinese Hamster Cell Mutants Deficient in Dihydrofolate Reductase Activity," Proceedings of the National Academy of Sciences, USA77(7):4216-4220, National Academy of Sciences, United States (1980).

Uyttendaele, H., et al., "Notch4 and Wnt-1 Proteins Function to Regulate Branching Morphogenesis of Mammary Epithelial Cells in an Opposing Fashion," Developmental Biology 196(2):204-217, Elsevier Inc., Netherlands (1998).

Van ES, J.H., and Clevers, H., "Notch and Wnt Inhibitors as Potential New Drugs for Intestinal Neoplastic Disease," Trends in Molecular Medicine 11(11):496-502, Elsevier Inc., Netherlands (2005).

(56) References Cited

OTHER PUBLICATIONS

Van Limpt, V., et al., "Sage Analysis of Neuroblastoma Reveals a High Expression of the Human Homologue of the*Drosophila* DeltaGene," Medical and Pediatric Oncology 35(6):554-558, Wiley-Liss, Inc., United States (2000).
Vaswani, S.K. and Hamilton, R.G., "Humanized antibodies as potential therapeutic drugs," Annals of Allergy, Asthma & Immunology 81(2):105-115, American College of Allergy, Asthma, & Immunology, United States (1998).
Vaughan, T.J., et al., "Human Antibodies with Sub-nanomolar Affinities Isolated from a Large non-Immunized Phage Display Library," Nature Biotechnology 14(3):309-314, Nature Publishing Co., United States (1996).
Verhoeyen, M., et al., "Reshaping Human Antibodies: Grafting an Antilysozyme Activity," Science 239(4847):1534-1536, American Association for the Advancement of Science, United States (1988).
Vincke, C., and Muyldermans, S., "Introduction to Heavy Chain Antibodies and Derived Nanobodies," Methods in Molecular Biology 911:15-26, Springer Science + Business Media, Germany (2012).
Wang, J.C., et al., "Primitive human hematopoietic cells are enriched in cord blood compared with adult bone marrow or mobilized peripheral blood as measured by the quantitative in vivo SCID-repopulating cell assay," Blood 89(11):3919-3924, American Society of Hematology, United States (1997).
Ward, E.S., "Antibody engineering using *Escherichia coli* as host," Advances in Pharmacology 24:1-20, Academic Press, United States (1993).
Weijzen, S., et al., "Activation of Notch-1 Signaling Maintains the Neoplastic Phenotype in Human Ras-Transformed Cells," Nature Medicine 8(9):979-986, Nature Publishing Group, United States (2002).
Weng, A.P., et al., "Activating Mutations of NOTCH1 in Human T Cell Acute Lymphoblastic Leukemia," Science 306(5694):269-271, American Association for the Advancement of Science, United States (2004).
Weng, A.P., et al., "Growth Suppression of Pre-T Acute Lymphoblastic Leukemia Cells by Inhibition of Notch Signaling," Molecular and Cellular Biology 23(2):655-664, American Society for Microbiology, United States (2003).
Williams, C.K., et al., "Up-regulation of the Notch ligand Delta-like 4 inhibits VEGF-induced endothelial cell function," Blood 107(3):931-939, American Society of Hematology, United States (2006).
Wilson, A. and Radtke, F., "Multiple Functions of Notch Signaling in Self-Renewing Organs and Cancer," FEBS Letters 580(12):2860-2868, Elsevier Science, United States (2006).
Wong, O.K., et al., "Voreloxin (formerly SNS-595) is a potent DNA intercalator and topoisomerase II poison that induces cell cycle dependent DNA damage and rapid apoptosis in cancer cell lines," 24th EORTC-NCI-AACR Symposium, Nov. 9, Poster 169, 1 page (2012).
Written Opinion for International Application No. PCT/US16/53316, ISA/US, Alexandria, Virginia, dated Feb. 21, 2017, 9 pages.
Written Opinion for International Application No. PCT/US2015/024251, ISA/US, Alexandria, Virginia, United States, dated Jul. 16, 2015, 7 pages.
Written Opinion of the International Searching Authority for International application No. PCT/US2007/020889, United States Patent and Trademark Office, United States, dated Apr. 9, 2008, 4 pages.
Written Opinion of the International Searching Authority for International Patent Application No. PCT/US11/60773, International Searching Authority, Alexandria, Virginia, United States, dated Mar. 26, 2012, 5 pages.
Wu, C., et al., "Simultaneous targeting of multiple disease mediators by a dual-variable-domain immunoglobulin," Nature Biotechnology 25(11):1290-1297, Nature Publishing Co., United States (2007).
Wu, H., et al., "Humanization of a Murine Monoclonal Antibody by Simultaneous Optimization of Framework and CDR Residues," Journal of Molecular Biology 294(1):151-162, Elsevier, England (1999).
Xu, A., et al., "Regions of *Drosophila* Notch that Contribute to Ligand Binding and the Modulatory Influence of Fringe," The Journal of Biological Chemistry 280(34):30158-30165, American Society for Biochemistry and Molecular Biology, United States (2005).
Yan, M., et al., "Chronic DLL4 blockade induces vascular neoplasms," Nature 463(7282):E6-E7, Macmillan Publishers Limited, England (2010).
Yan, Wei., "Design and Engineering of Fc Heterodimers for the Production of Bispecific Antibodies," Symposium Abstract, Keystone Symposia on Molecular and Cellular Biology, Accelerating Life Science Discovery, Mar. 27-Apr. 1, 2009, Whistler, British Columbia.
Yan, Wei, The Design and Engineering of Fc Heterodimers for the Production of Bispecific Antibodies and Other Heterodimer Fusion Proteins, Symposium Abstract, 20th Annual International Conference, Antibody Engineering, Antibody Engineering and Immunotherapeutics for the 21st Century, Dec. 6-10, 2009, San Diego, California.
Yan, Wei, "The Design and Engineering of Fc Heterodimers for the Production of Bispecific Antibodies," Symposium Abstract, Eleventh Annual Phage Display of Antibodies and Peptides, Approaches for 2nd Generation Biologics, Apr. 6-Apr. 7, 2009, Boston, Massachusetts.
Yan, X.Q., et al., "A novel Notch ligand, Dll4, induces T-cell leukemia/lymphoma when overexpressed in mice by retroviral-mediated gene transfer," Blood 98(13):3793-3799, American Society of Hematology, United States (2001).
Yelton, D.E., "Affinity maturation of the BR96 anti-carcinoma antibody by codon-based mutagenesis," The Journal of Immunology 155(4):1994-2004, The American Association of Immunologists, United States (1995).
Yen, W., et al., "Targeting Cancer Stem Cells and Vasculature by a Novel Anti-Delta-Like 4 Ligand (DLL4) Antibody for Treatment of Triple Negative Breast Cancer," Cancer Research 69(Suppl. )(24):788s-789s, Abstract 5071, American Association for Cancer Research, United Sates (2009).
Yen, W.C., at al., "Targeting Cancer Stem Cells and Vasculature by a Novel Anti-Dll4 Antibody Inhibits Pancreatic Tumor Growth and Delays Tumor Recurrence," Presented at the 100th Annual Meeting of the American Association for Cancer Research in Denver, Colorado on Apr. 18-22, 2009.
Yen, W-C., et al., "Anti-DLL4 (demcizumab) inhibits tumor growth and reduces cancer stem cell frequency in patient-derived ovarian cancer xenografts," AACR 104th Annual Meeting 2013, Abstract 3725, Apr. 6-10, 1 page (2013).
Yen, W.C., et al., "Anti-DLL4 has broad spectrum activity in pancreatic cancer dependent on targeting DLL4-Notch signaling in both tumor and vasculature cells," Clinical Cancer Research 18(19):5374-5386, American Association for Cancer Research, United States (2012).
Yen, W-C., et al., "Dual targeting of DLL4 and VEGF signaling by a novel bispecific antibody inhibits tumor growth and reduces cancer stem cell frequency," AACR Annual Meeting 2014, Apr. 5-9, 2014, Abstract 207, 1 page (2014).
Yen, W-C., et al., "Targeting cancer stem cells by an anti-DLL4 antibody inhibits epithelial-to-mesenchymal transition, delays tumor recurrence and overcomes drug resistance in breast and pancreatic cancer," AACR 103rd Annual Meeting 2012, Mar. 31-Apr. 4, Abstract 3357, 1 page (2013).
Yen, W-C., et al., "The combination of gemcitabine/nab-paclitaxel and anti-DLL4 (demcizumab) produces synergistic growth inhibition, delays tumor recurrence and reduces tumor initiating cells in pancreatic cancer," American Association for Cancer Research Annual Meeting 2014, Abstract 1898, 1 page (2014).
Yoneya, T., et al., "Molecular Cloning of Delta-4, A New Mouse and Human Notch Ligand," Journal of Biochemistry 129(1):27-34, Japanese Biochemical Society, Japan (2001).

(56) References Cited

OTHER PUBLICATIONS

Zagouras, P., et al., "Alterations in Notch Signaling in Neoplastic Lesions of the Human Cervix," Proceedings of the National Academy of Sciences 92(14):6414-6418, National Academy of Sciences, United States (1995).

Mochizuki, K., et al., "Delta-like Ligand 4 Identifies a Previously Uncharacterized Population of Inflammatory Dendritic Cells That Plays Important Roles in Eliciting Allogeneic T Cell Responses in Mice," in: The Journal of Immunology 190(7):3772-3782, American Association of Immunologists, Bethesda, MD (Apr. 2013).

Figure 1A
Subject 1: Blood Pressure and Antihypertensive Treatment

| Study Day | OMP-21M18 Infusion # | Pre-Infusion BP (mm Hg) | 15 minutes after start of infusion BP (mm Hg) | End of Infusion BP (mm Hg) | 15 minutes post infusion BP (mm Hg) | Other BP (mm Hg) | Oral anti-hypertensive medication added or modified | Reason oral anti-hypertensive added/ modified/ discontinued |
|---|---|---|---|---|---|---|---|---|
| -155 | | | | | | | Benazepril (Lotensin) 30 mg po qd | Hypertension |
| -1 | | | | | | 135/73 | | |
| 0 | 1 | 135/72 | 145/77 | 147/75 | 149/71 | | | |
| 7 | 2 | 140/74 | 140/76 | 150/75 | 159/75 | | | |
| 14 | 3 | 153/78 | 149/73 | 153/70 | 164/76 | | | |
| 21 | 4 | 164/73 | 178/85 | 190/90 | 199/92 | | | |
| 24 | | | | | | 183/89* | Lotensin 40 mg po qd + amlodipine besylate (Norvasc) 5 mg qd | Modifications made to decrease BP |
| 25 | | | | | | 156/70* | | |
| 25 | | | | | | 178/90* | | |
| 26 | | | | | | 173/75* | | |
| 26 | | | | | | 168/83* | | |
| 27 | | | | | | 170/75* | | |
| 27 | | | | | | 180/80* | | |
| 28 | 5 | 160/77 | 162/78 | 173/80 | 173/79 | 150/76* | | |
| 28 | | | | | | 160/77* | | |
| 29 | | | | | | 175/78* | | |
| 29 | | | | | | 156/78* | | |
| 30 | | | | | | 159/84* | | |
| 30 | | | | | | 160/72* | | |
| 31 | | | | | | 178/86* | | |
| 31 | | | | | | 180/95* | | |
| 31 | | | | | | 177/88* | | |
| 32 | | | | | | 146/70* | Increase Norvasc to 10 mg po qd | Increase in Norvasc dose to further reduce BP |
| 32 | | | | | | 170/85* | | |
| 33 | | | | | | 159/76* | | |
| 34 | | | | | | 151/72* | | |
| 35 | 6 | 152/99 | 150/81 | 150/80 | 151/80 | 170/71* | | |
| 35 | | | | | | 160/79* | | |
| 36 | | | | | | 148/86* | | |
| 37 | | | | | | 152/83* | | |
| 38 | | | | | | 166/78* | | |
| 38 | | | | | | 157/78* | | |
| 39 | | | | | | 155/75* | | |

Figure 1B

Subject 1: Blood Pressure and Antihypertensive Treatment (continued)

| Study Day | OMP-21M18 Infusion # | Pre-Infusion BP (mm Hg) | 15 minutes after start of infusion BP (mm Hg) | End of Infusion BP (mm Hg) | 15 minutes post infusion BP (mm Hg) | Other BP (mm Hg) | Oral anti-hypertensive medication added or modified | Reason oral anti-hypertensive added/ modified/ discontinued |
|---|---|---|---|---|---|---|---|---|
| 40 | | | | | | 158/81* | | |
| 41 | | | | | | 160/85* | Hydrochorothiazide 25 mg po qd | Hydrochorothiazine added to further reduce BP |
| 42 | 7 | 151/79 | 148/75 | 154/79 | 147/78 | 166/79* | | |
| 43 | | | | | | 158/76* | | |
| 44 | | | | | | 140/73* | | |
| 45 | | | | | | 131/68* | | |
| 46 | | | | | | 152/76* | | |
| 47 | | | | | | 148/77* | | |
| 48 | | | | | | 135/67* | | |
| 49 | 8 | 132/73 | 136/70 | 146/82 | 156/80 | 143/73* | | |
| 51 | | | | | | 156/74* | | |
| 52 | | | | | | 157/77* | | |
| 53 | | | | | | 156/80* | | |
| 54 | | | | | | 124/66* | | |
| 55 | | | | | | 133/65* | | |
| 56 | 9 | 129/70 | 118/69 | 115/68 | 136/72 | 126/64* | | |
| 64 | Study termination visit | | | | | 141/73 | | |

* = home blood pressure measurements

Figure 2A
Subject 2: Blood Pressure and Antihypertensive Treatment

| Study Day | OMP-21M18 Infusion # | Pre-Infusion BP (mm Hg) | 15 minutes after start of infusion BP (mm Hg) | End of Infusion BP (mm Hg) | 15 minutes post infusion BP (mm Hg) | Other BP (mm Hg) | Oral anti-hypertensive medication added or modified | Reason oral anti-hypertensive added/ modified/ discontinued |
|---|---|---|---|---|---|---|---|---|
| Screen | | | | | | 142/87 | Lisinopril 10 mg po qd since July 05 | Hypertension |
| 0 | 1 | 141/85 | 136/71 | 127/70 | 132/81 | 140/95 | | |
| 1 | | | | | | 157/87 | | |
| 3 | | | | | | 154/93 | | |
| 7 | 2 | 153/87 | 140/87 | 130/87 | 153/100 | 177/93 | | |
| 13 | | | | | | | Irbesartan/hydro-chlorothiazide 300/ 12.5 po qd | Increase in BP to 177/93 |
| 14 | Dose held | 173/110 | | | | 152/104 168/106 172/106 174/196 188/120* | | |
| 15 | | | | | | 171/108* 179/116* 181/111* | | |
| 16 | | | | | | 145/101* 170/110* | | |
| 17 | | | | | | | DC Irbesartan/ hydrochlorothiazide and lisinopril Start Labetalol 100 mg po bid, Pirnzide 10/12.5 po qd | To achieve better control of BP |
| 19 | | | | | | 156/94* 137/92* 175/116* | | |
| 20 | | | | | | 159/103* ?/100* 151/98* | | |
| 21 | | | | | | 164/112 165/102 | Labetalol 300 mg AM, 200 mg PM | To further reduce BP |
| 22 | 3 | 130/81 | 138/78 | 125/80 | 155/92 | 140/90 144/85 160/112 | Labetalol 400 mg AM, 200 mg PM | To further reduce BP |
| | | | | | | | Labetelol 400 mg bid | To further reduce BP |
| 28 | 4 | 151/85 | 151/83 | 136/78 | 147/81 | 151/86 | | |
| 35 | 5 | 135/60 | 136/80 | 133/79 | 133/79 | 119/77 | | |
| 42 | 6 | 146/80 | 140/69 | 144/80 | 139/75 | 147/87 | | |
| 49 | 7 | 139/88 | 130/77 | 140/85 | 132/80 | 151/94 168/98 | | |
| 50 | | | | | | 145/85 | | |
| 52 | | | | | | 159/92 | | |

Figure 2B
Subject 2: Blood Pressure and Antihypertensive Treatment (continued)

| Study Day | OMP-21M18 Infusion # | Pre-Infusion BP (mm Hg) | 15 minutes after start of infusion BP (mm Hg) | End of Infusion BP (mm Hg) | 15 minutes post infusion BP (mm Hg) | Other BP (mm Hg) | Oral anti-hypertensive medication added or modified | Reason oral anti-hypertensive added/ modified/ discontinued |
|---|---|---|---|---|---|---|---|---|
| 55 | 8 | 148/82 | 161/96 | 151/85 | 152/92 | 163/91 | Modify Prinzide® to 20/25 | Changed due to persistent hypertension |
| 70 | 9 | 143/87 | 170/97 | 157/102 | 158/97 | 142/86 | | |
| 84 | Dose held | 163/93 | | | | 167/102 | Lasix 20 mg po qd | Added due to persistent hypertension with edema |
| 85 | | | | | | 164/106* 177/106* | | |
| 86 | | | | | | 162/102* 138/97* | | |
| 87 | | | | | | 142/93* | Norvasc® 10 mg po qd | Continued systolic and diastolic hypertension |
| 88 | | | | | | 131/85* | | |
| 89 | | | | | | 134/88* | | |
| 90 | | | | | | 142/91* 143/97* | | |
| 91 | | | | | | 127/82* 161/96* | | |
| 92 | | | | | | 125/78* 161/96* 125/78* 135/101* | | |
| 93 | | | | | | 142/96* 168/108* | | |
| 94 | | | | | | 133/91* 127/81* | | |
| 95 | | | | | | 124/89* 135/96* | | |
| 96 | | | | | | 131/90* 131/76* | | |
| 97 | | | | | | 122/84* | | |
| 98 | 10 | 129/76 | 130/64 | 116/60 | 118/62 | 125/67 | | |
| 112 | 11 | 117/61 | 109/67 | 121/68 | 109/63 | 118/69 | | |
| 126 | 12 | 121/76 | 121/72 | 128/72 | 114/68 | 112/57 | | |
| 140 | 13 | 129/86 | 118/65 | 122/67 | 142/68 | 121/76 | | |
| 153 | 14 | 116/71 | 118/85 | 112/69 | 117/71 | 116/75 116/71 118/85 112/69 117/71 | | |

Figure 2C

Subject 2: Blood Pressure and Antihypertensive Treatment (continued)

| Study Day | OMP-21M18 Infusion # | Pre-Infusion BP (mm Hg) | 15 minutes after start of infusion BP (mm Hg) | End of Infusion BP (mm Hg) | 15 minutes post infusion BP (mm Hg) | Other BP (mm Hg) | Oral anti-hypertensive medication added or modified | Reason oral anti-hypertensive added/ modified/ discontinued |
|---|---|---|---|---|---|---|---|---|
| 168 | 15 | 114/80 | 126/74 | 127/80 | 129/86 | 122/71 114/80 126/74 127/80 129/86 | | |
| 182 | 16 | 136/84 | 144/83 | 133/68 | 140/85 | 132/76 136/84 144/83 133/68 140/85 | | |
| 196 | | | | | | 134/80 134/89 134/75 126/80 127/82 | | |
| 210 | | | | | | 145/81 140/80 142/84 154/90 148/89 | | |
| 211 | | | | | | 150/88 | | |
| 219 | | | | | | 156/95 | | |
| 224 | | | | | | 134/82 | | |
| 232 | | | | | | 153/96 | | |

* = home blood pressure measurements

Figure 3
Subject 3: Blood Pressure and Antihypertensive Treatment

| Study Day | OMP-21M18 Infusion # | Pre-Infusion BP (mm Hg) | 15 minutes after start of infusion BP (mm Hg) | End of Infusion BP (mm Hg) | 15 minutes post infusion BP (mm Hg) | Other BP (mm Hg) | Oral anti-hypertensive medication added or modified | Reason oral anti-hypertensive added/ modified/ discontinued |
|---|---|---|---|---|---|---|---|---|
| -26 | | | | | | 96/54 | | |
| 0 | 1 | 132/69 | 134/62 | 134/70 | 127/63 | 144/66 135/67 | | |
| 1 | | | | | | 141/67 | | |
| 3 | | | | | | 148/74 | | |
| 7 | 2 | 143/68 | 135/63 | 133/68 | 134/69 | 150/73 134/64 | | |
| 14 | 3 | 166/80 | 163/77 | 166/74 | 162/74 | 160/79 | | |
| 21 | 4 | 160/76 | 151/76 | 156/87 | 148/78 | 159/90 | Dyazide 1 po qd | Added for persistent hypertension |
| 28 | 5 | 128/70 | 148/80 | 141/66 | 143/67 | 136/71 | | |
| 35 | 6 | 134/66 | 136/74 | 131/73 | 131/69 | 140/67 | | |
| 42 | 7 | 138/74 | 121/63 | 121/63 | 120/66 | 141/80 | | |
| 49 | 8 | 135/71 | 144/67 | 129/63 | 142/80 | 158/72 138/69 | | |
| 50 | | | | | | 137/61 | | |
| 52 | | | | | | 147/78 | | |
| 56 | 9 | 144/79 | 141/67 | 140/68 | 140/68 | 145/79 162/76 | | |
| 70 | 10 | 154/82 | 151/79 | 146/84 | 153/90 | 136/68 | | |
| 84 | 11 | 152/77 | 143/77 | 150/78 | 151/75 | 157/81 158/81 | | |
| 98 | 12 | 161/85 | 167/78 | 171/81 | 165/81 | 162/91 | | |
| 112 | 13 | 150/79 | 153/76 | 136/68 | 137/70 | 152/77 | DC Dyazide Norvasc 5 mg po qd | Changed for persistent increase in BP |
| 126 | | | | | | 168/79 162/72 164/85 152/87 163/85 | | |
| 141 | | | | | | 174/89 158/78 | DC Norvasc Start lisinopril 20 mg po qd | Changed due to ankle edema with Norvasc |
| 144 | | | | | | | Increase lisinopril to 20 mg po bid | Increased due to persistent hypertension |
| 146 | | | | | | 143/85 | | |

\* = home blood pressure measurements

Figure 4
Subject 5: Blood Pressure and Antihypertensive Treatment

| Study Day | OMP-21M18 Infusion # | Pre-Infusion BP (mm Hg) | 15 minutes after start of infusion BP (mm Hg) | End of Infusion BP (mm Hg) | 15 minutes post infusion BP (mm Hg) | Other BP (mm Hg) | Oral anti-hypertensive medication added or modified | Reason oral anti-hypertensive added/ modified/ discontinued |
|---|---|---|---|---|---|---|---|---|
| -28 | | | | | | 130/90 | | |
| -1 | | | | | | | | |
| 0 | 1 | 130/90 | 130/80 | 130/90 | 135/90 | | | |
| 7 | | | | | | 130/90 | | |
| 9 | | | | | | 160/90 | Start Diroton, 10 mg po qd | Hypertension, Headache |
| 14 | 2 | 140/90 | 139/90 | 135/90 | 140/90 | | Reduce lisinopril to 5 mg po qd | Normal BP and no complaints |
| 21 | | | | | | 130/90 | | |
| 26 | | | | | | 170/90* | Captopril 25 mg po X 1 only | BP of 170/90 – subject's decision |
| 28 | 3 | 105/75 | 110/75 | 115/75 | 115/80 | | Increase lisinopril to 10 mg po qd | BP of 170/90 |
| 29–34 | | | | | | 140-150/90* | | |
| 35 | | | | | | 140/90 | | |
| 36–41 | | | | | | 130-140/90* | | |
| 42 | 4 | 130/90 | 130/90 | 135/90 | 140/90 | | | |
| 43–48 | | | | | | 130-140/90* | | |
| 49 | | | | | | 130/80 | | |
| 50 | | | | | | 170/90 before lisinopril and 140-150/90 after lisinopril* | | |
| 56 | 5 | 140/90 | 145/90 | 140/90 | 140/90 | | Increase lisinopril to 10 mg po qd | BP of 140-145/90 |
| 62 | | | | | | 190/120 | DC lisinopril. Start Lozap (lozartan) 25 mg po qd + Bidop (bisoprolol) 2.5 mg po qd + Cordicor (amlodipine) 5 mg po qd | Lisinopril ineffective. New medications prescribed by cardiologist. |
| 63 | | | | | | 160/95* | | |
| 65 | | | | | | 170/106* | Increase Lozap to 50 mg po qd + increase Bidop to 5 mg po qd | BP of 160/90. Cardiologists increased doses |
| 66 | | | | | | 170-180/90 | | |
| 70 | | | | | | 150/90 | | |
| 84 | | | | | | 170/90 | | |

\* = home blood pressure measurements

Figure 5

Subject 7: Blood Pressure and Antihypertensive Treatment

| Study Day | OMP-21M18 Infusion # | Pre-Infusion BP (mm Hg) | 15 minutes after start of infusion BP (mm Hg) | End of Infusion BP (mm Hg) | 15 minutes post infusion BP (mm Hg) | Other BP (mm Hg) | Oral anti-hypertensive medication added or modified | Reason oral anti-hypertensive added/ modified/ discontinued |
|---|---|---|---|---|---|---|---|---|
| | | | | | | | Enalapril 5 mg po bid | Hypertension |
| -1 | | | | | | 135/90 | | |
| -4 | | | | | | 125/80 | | |
| 0 | 1 | 130/80 | 130/80 | 125/80 | 120/80 | | | |
| 7 | | | | | | 140/90 | | |
| 9 | | | | | | | Increase enalapril dose to 10 mg po bid | BP of 170/90 – subject's own decision |
| 9-11 | | | | | | 170/90* | | |
| 14 | 2 | 150/90 | 145/90 | 140/90 | 140/90 | | | |
| 21 | | | | | | 145/90 | | |
| 24 | | | | | | 170/90* | | |
| 28 | 3 | 145/90 | 150/90 | 140/85 | 150/90 | | | |
| 29-34 | | | | | | 150/90* | | |
| 35 | | | | | | 150/90 | | |
| 36-41 | | | | | | 140/90* | | |
| 42 | 4 | 140/90 | 145/80 | 145/85 | 145/80 | | | |
| 43-48 | | | | | | 140/90* | | |
| 49 | | | | | | 140/90 | | |
| 50-55 | | | | | | 190/100* | | |
| 56 | 5 | 155/90 | 150/90 | 150/90 | 150/90 | | Add amlodipine 5 mg po qd | |
| 57-69 | | | | | | 150-160/90 | | |
| 70 | 6 | 145/90 | 145/90 | 150/90 | 145/90 | | | |

* = home blood pressure measurements

Figure 6

Subject 8: Blood Pressure and Antihypertensive Treatment

| Study Day | OMP-21M18 Infusion # | Pre-Infusion BP (mm Hg) | 15 minutes after start of infusion BP (mm Hg) | End of Infusion BP (mm Hg) | 15 minutes post infusion BP (mm Hg) | Other BP (mm Hg) | Oral anti-hypertensive medication added or modified | Reason oral anti-hypertensive added/modified/discontinued |
|---|---|---|---|---|---|---|---|---|
| | | | | | | | Captopril 25 mg po as needed | Hypertension |
| -28 | | | | | | 140/90 | | |
| 0 | 1 | 130/80 | 125/80 | 120/80 | 135/80 | | | |
| 7 | | | | | | 120/80 | | |
| 9 | | | | | | 150/90* | | |
| 14 | 2 | 120/80 | 120/75 | 120/70 | 120/80 | | | |
| 17 | | | | | | 160/90* | | |
| 18 | | | | | | 130/80 | | Modify captopril to 12.5 mg po qd | BP of 160/90 – headache, subject's own decision |
| 22 | | | | | | 130/80 | | |
| 23-28 | | | | | | 150/90* | Modify captopril to 25 mg po qd | BP of 150/90 – subject's own decision |
| 29 | 3 | 130/90 | 130/90 | 135/90 | 135/90 | | | |
| 30-35 | | | | | | 150/90* | | |
| 36 | | | | | | 140/90 | | |
| 37-41 | | | | | | 150/90* | | |
| 43 | 4 | 130/90 | 130/80 | 135/90 | 140/90 | | | |
| 45-47 | | | | | | 150/90* | | |
| 50 | | | | | | 145/90 | | |
| 51-56 | | | | | | 140-150/90* | | |
| 57 | 5 | 135/90 | 140/80 | 150/90 | 140/90 | | | |
| 58-70 | | | | | | 140-150/90* | | |
| 71 | 6 | 130/90 | 135/90 | 135/90 | 135/90 | | | |
| 72-84 | | | | | | 140-150/90* | | |
| 85 | 7 | 135/90 | 135/95 | 140/95 | 140/90 | | | |

* = home blood pressure measurements

Figure 7

Subject 9: Blood Pressure and Antihypertensive Treatment

| Study Day | OMP-21M18 Infusion # | Pre-Infusion BP (mm Hg) | 15 minutes after start of infusion BP (mm Hg) | End of Infusion BP (mm Hg) | 15 minutes post infusion BP (mm Hg) | Other BP (mm Hg) | Oral anti-hypertensive medication added or modified | Reason oral anti-hypertensive added/ modified/ discontinued |
|---|---|---|---|---|---|---|---|---|
| -1 | | | | | | 115/75 | | |
| 0 | 1 | 115/75 | 115/75 | 115/75 | 115/75 | | | |
| 1 | | | | | | 140/90 | | |
| 3 | | | | | | 140-145/ 90-95 | Nifedipine 20 mg po qd | Hypertension, Headache, (BP of 140-45/90-95) |
| 7 | | | | | | 130/80 | | |
| 14 | 2 | 145/85 | 140/85 | 140/80 | 140/80 | | | |
| 21 | | | | | | 135/80 | | |
| 28 | 3 | 125/85 | 125/85 | 125/85 | 125/85 | | | |
| 34 | | | | | | 130/80 | | |
| 41 | 4 | 125/85 | 125/85 | 125/85 | 125/85 | | | |
| 48 | | | | | | 125/85 | | |
| 54 | 5 | 130/75 | 130/75 | 130/75 | 130/75 | | | |
| 67 | 6 | 120/70 | 120/70 | 120/70 | 120/70 | | | |
| 74 | | | | | | 115/75* | Nifedipine discontinued | Normalization of blood pressure, subject's own decision |
| 81 | 7 | | | | | 115/75 | | |

\* = home blood pressure measurements

SEQUENCE LISTING

```
<160> NUMBER OF SEQ ID NOS: 11

<210> SEQ ID NO 1
<211> LENGTH: 6
<212> TYPE: PRT
<213> ORGANISM: Artificial Sequence
<220> FEATURE:
<223> OTHER INFORMATION: Heavy chain CDR1

<400> SEQUENCE: 1
```

Thr Ala Tyr Tyr Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: Heavy chain CDR2, H2

<400> SEQUENCE: 2

Tyr Ile Ser Cys Tyr Asn Gly Ala Thr Asn Tyr Asn Gln Lys Phe Lys
1               5                   10                  15

Gly

<210> SEQ ID NO 3
<211> LENGTH: 17
<212> TYPE: PRT
<213> ORGANISM: Artificial Sequence
<220> FEATURE:
<223> OTHER INFORMATION: Heavy chain CDR2 H7

<400> SEQUENCE: 3

Tyr Ile Ser Ser Tyr Asn Gly Ala Thr Asn Tyr Asn Gln Lys Phe Lys
1               5                   10                  15

Gly

<210> SEQ ID NO 4
<211> LENGTH: 17
<212> TYPE: PRT
<213> ORGANISM: Artificial Sequence
<220> FEATURE:
<223> OTHER INFORMATION: Heavy chain CDR2 H9

<400> SEQUENCE: 4

Tyr Ile Ser Val Tyr Asn Gly Ala Thr Asn Tyr Asn Gln Lys Phe Lys
1               5                   10                  15

Gly

<210> SEQ ID NO 5
<211> LENGTH: 11
<212> TYPE: PRT
<213> ORGANISM: Artificial Sequence
<220> FEATURE:
<223> OTHER INFORMATION: Heavy chain CDR3

<400> SEQUENCE: 5

Arg Asp Tyr Asp Tyr Asp Val Gly Met Asp Tyr
1               5                   10

<210> SEQ ID NO 6
<211> LENGTH: 119
<212> TYPE: PRT
<213> ORGANISM: Artificial Sequence
<220> FEATURE:
<223> OTHER INFORMATION: Heavy chain variable region, H7

<400> SEQUENCE: 6

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
            20                  25                  30

Tyr Ile His Trp Val Lys Gln Ala Pro Gly Gln Gly Leu Glu Trp Ile

```
                35                  40                  45
Gly Tyr Ile Ser Ser Tyr Asn Gly Ala Thr Asn Tyr Asn Gln Lys Phe
    50                  55                  60
Lys Gly Arg Val Thr Phe Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Asp Tyr Asp Tyr Asp Val Gly Met Asp Tyr Trp Gly Gln Gly
            100                 105                 110
Thr Leu Val Thr Val Ser Ser
            115

<210> SEQ ID NO 7
<211> LENGTH: 15
<212> TYPE: PRT
<213> ORGANISM: Artificial Sequence
<220> FEATURE:
<223> OTHER INFORMATION: Light chain CDR1

<400> SEQUENCE: 7

Arg Ala Ser Glu Ser Val Asp Asn Tyr Gly Ile Ser Phe Met Lys
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: Light chain CDR2

<400> SEQUENCE: 8

Ala Ala Ser Asn Gln Gly Ser
1               5

<210> SEQ ID NO 9
<211> LENGTH: 12
<212> TYPE: PRT
<213> ORGANISM: Artificial Sequence
<220> FEATURE:
<223> OTHER INFORMATION: Light chain CDR3

<400> SEQUENCE: 9

Gln Gln Ser Lys Glu Val Pro Trp Thr Phe Gly Gly
1               5                   10

<210> SEQ ID NO 10
<211> LENGTH: 111
<212> TYPE: PRT
<213> ORGANISM: Artificial Sequence
<220> FEATURE:
<223> OTHER INFORMATION: Light chain variable region

<400> SEQUENCE: 10

Asp Ile Val Met Thr Gln Ser Pro Asp Ser Leu Ala Val Ser Leu Gly
1               5                   10                  15
Glu Arg Ala Thr Ile Ser Cys Arg Ala Ser Glu Ser Val Asp Asn Tyr
            20                  25                  30
Gly Ile Ser Phe Met Lys Trp Phe Gln Gln Lys Pro Gly Gln Pro Pro
        35                  40                  45
Lys Leu Leu Ile Tyr Ala Ala Ser Asn Gln Gly Ser Gly Val Pro Asp
    50                  55                  60
Arg Phe Ser Gly Ser Gly Ser Gly Thr Asp Phe Thr Leu Thr Ile Ser
```

```
                        65                  70                  75                  80
Ser Leu Gln Ala Glu Asp Val Ala Val Tyr Tyr Cys Gln Gln Ser Lys
                            85                  90                  95

Glu Val Pro Trp Thr Phe Gly Gly Gly Thr Lys Val Glu Ile Lys
                100                 105                 110

<210> SEQ ID NO 11
<211> LENGTH: 154
<212> TYPE: PRT
<213> ORGANISM: Artificial Sequence
<220> FEATURE:
<223> OTHER INFORMATION: Human DLL4 N-Terminal Region

<400> SEQUENCE: 11

Met Ala Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
                20                  25                  30

Gln Leu Gln Glu Phe Ile Asn Glu Arg Gly Val Leu Ala Ser Gly Arg
            35                  40                  45

Pro Cys Glu Pro Gly Cys Arg Thr Phe Phe Arg Val Cys Leu Lys His
        50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
    130                 135                 140

Ile Gln Gly Ser Leu Ala Val Gly Gln Asn
145                 150
```

THERAPEUTIC COMBINATION AND METHODS OF TREATMENT WITH A DLL4 ANTAGONIST AND AN ANTI-HYPERTENSIVE AGENT

CROSS REFERENCE TO RELATED APPLICATIONS

The present application is a Divisional of U.S. application Ser. No. 14/498,602, filed Sep. 26, 2014, now U.S. Pat. No. 9,511,139, which is a Divisional of U.S. application Ser. No. 13/501,944, 371(c) date Jun. 26, 2012, now U.S. Pat. No. 8,883,145, which is a U.S. National Phase of International Application No. PCT/US2010/053064, filed Oct. 18, 2010, which claims the benefit of U.S. Provisional Application No. 61/252,473, filed Oct. 16, 2009, each of which are incorporated herein by reference in their entirety.

REFERENCE TO A SEQUENCE LISTING SUBMITTED ELECTRONICALLY VIA EFS-WEB

The content of the electronically submitted sequence listing (Name: 2293_0610003_SeqListing.txt, Size: 5,904 bytes; and Date of Creation: Oct. 26, 2016) is herein incorporated by reference in its entirety.

DESCRIPTION OF THE INVENTION

Field of Invention

The present invention relates to the field of oncology and provides novel compositions and methods for treating cancer. The present invention provides a pharmaceutical composition comprising a DLL4 antagonist and one or more anti-hypertensive agents, and methods and kits for using the same.

Background

Cancer is one of the leading causes of death in the developed world, with over one million people diagnosed with cancer and 500,000 deaths per year in the United States alone. Overall it is estimated that more than 1 in 3 people will develop some form of cancer during their lifetime. There are more than 200 different types of cancer, four of which—breast, lung, colorectal, and prostate—account for over half of all new cases (Jemal et al., 2003, Cancer J. Clin. 53:5-26).

Increasingly, treatment of cancer has moved from the use of systemically acting cytotoxic drugs to include more targeted therapies that hone in on the mechanisms that allow unregulated cell growth and survival. Tumor angiogenesis, the process by which a tumor establishes an independent blood supply, is a critical step for tumor growth. Efforts to target tumor angiogenesis have emerged as an important strategy for the development of novel cancer therapeutics.

Tumors cannot continue to grow beyond about 2 mm in diameter without developing blood vessels to deliver oxygen and nutrients, and to remove cellular waste. Tumors release angiogenic factors that act on the receptors of endothelial cells of nearby blood vessels, causing proliferation and the development of new blood vessels directed toward the site of angiogenic factor release, i.e., the tumor. This tumor-induced vasculature has received enormous interest as a target for antineoplastic therapy because a relatively small number of blood vessels are critical for the survival and continued growth of a much larger group of cancer cells. The disruption in the function of a single tumor blood vessel can result in an avalanche of ischemic cell death and necrosis of thousands of tumor cells which depend on it for blood supply. Thus, drugs that disrupt the ability of a tumor to induce or maintain an independent blood supply are promising cancer treatments.

Drugs that target tumor angiogenesis generally fall into one of two categories: anti-angiogenic drugs and dysangiogenic drugs. Anti-angiogenic drugs block the development and maintenance of new blood vessels, and thus impede tumor growth. An example of an anti-angiogenic drug is bevacizumab (Avastin®), an anti-vascular endothelial growth factor (VEGF) antibody. Dysangiogenic drugs, in contrast, result in disregulated angiogenesis, leading to the development of dysfunctional or nonfunctional vasculature.

The Notch pathway is involved in multiple aspects of vascular development including proliferation, migration, smooth muscle differentiation, angiogenesis and arterial-venous differentiation (Iso et al., 2003, Arterioscler. Thromb. Vasc. Biol. 23:543). The Notch receptor ligand DLL4 (Delta-like ligand 4) is an important component of the Notch pathway and plays a role in angiogenesis. Heterozygous loss of DLL4 result in severe defects in arterial development and yolk sac vascularization, leading to embryonic lethality. (Duarte et al., 2004, Genes Dev., 18:2474-78; Gale et al., 2004, PNAS, 101:15949-54; Krebs et al., 2004, Genes Dev., 18:2469-73) Furthermore, tumor cells and tumor vasculature over express DLL4, suggesting that DLL4 expression is an important player in tumor angiogenesis. (Patel et al., 2005, Cancer Res., 65:8690-97; Yan et al., 2001, Blood, 98:3793-99) Thus, blocking DLL4 signaling has emerged as a promising avenue for the development of new anti-cancer therapies.

Blocking DLL4 signaling, such as by an anti-DLL4 antibody, has been shown to reduce tumor growth by multiple different mechanisms. (Ridgway et al., 2006, Nature, 444:1083-87; Noguera-Troise et al., Nature, 444:1032-37; Hoey et al., 2009, Cell Stem Cell, 5:168-77) For example, DLL4 blocking antibodies have been reported to result in endothelial cell proliferation and the development of blood vessels, however, these blood vessels lack a functional lumen. This dysangiogenic effect has been reported to block tumor growth by promoting the development of only non-functional blood vessels. (Ridgeway et al. and Noguera-Troise et al. (above); Scehnet et al., 2007, Blood, 109:4753-60) Additionally, DLL4 blocking antibodies have been shown to inhibit tumor growth by reducing the proliferation of tumor cells and reducing cancer stem cell frequency. Although the mechanism behind the reduction of tumor initiating cells (cancer stem cells, or CSCs) is unknown, it is hypothesized that DLL4 is required for the self-renewal of CSCs and maintains these cells in an undifferentiated state. (Hoey et al., above)

Unlike therapeutic approaches that attempt to block the signaling of tumor angiogenic factors, blockade of DLL4 signaling by anti-human DLL4 antibodies can result in endothelial hypertrophy and the creation of non-functional microvessels. Consequently, even in the presence of tumor angiogenic factors, blockade of DLL4 signaling, through administration of anti-human DLL4 antibodies, can result in dysangiogenesis which inhibits the ability of the tumor to induce the functional blood vessel formation needed to support growth of the tumor.

Anti-angiogenic drugs, such as the anti-VEGF antibody bevacizumab (Avastin®), sunitinib (Sutent®), and sorafenib (Nexavar®), are known to cause hypertension in about one-third of patients who take them. Although anti-Dll4 antibodies have been reported to inhibit tumor angiogenesis by promoting dysangiogenesis, a mechanism different than that of traditional anti-angiogenic treatments, the present inventors have now surprisingly found that an anti-Dll4 antibody can cause hypertension in some patients. Thus, there is a need for methods of treating cancer with a DLL4 antagonist, such as an anti-DLL4 antibody, while controlling the hypertension caused thereby.

It is a purpose of the invention to provide pharmaceutical compositions, methods, and kits for treating cancer with a DLL4 antagonist while controlling hypertension through the administration of one or more anti-hypertensive agents.

SUMMARY OF THE INVENTION

Provided are methods for treating cancer comprising administering to a subject in need thereof a DLL4 antagonist and one or more anti-hypertensive agents. Further provided are compositions and kits comprising a DLL4 antagonist and one or more anti-hypertensive agents. Also provided are methods of ameliorating hypertension in a patient receiving treatment with a DLL4 antagonist comprising administering to the patient an effective amount of one or more anti-hypertensive agents. Further provided are methods of preventing hypertension in a patient receiving treatment with a DLL4 antagonist comprising administering to the patient an effective amount of an anti-hypertensive agent. Also provided are methods of monitoring a patient receiving treatment with a DLL4 antagonist for the development of hypertension, comprising measuring the blood pressure of a patient receiving treatment with a DLL4 antagonist and administering to the patient with a blood pressure above normal range one or more anti-hypertensive agents.

In certain embodiments, the DLL4 antagonist is an antibody that specifically binds DLL4 (i.e., an anti-DLL4 antibody). In certain embodiments, the DLL4 to which the anti-DLL4 antibody binds is human DLL4. In one embodiment, the anti-DLL4 antibody is a monoclonal antibody. In a further embodiment, the anti-DLL4 antibody specifically binds to a human DLL4 epitope comprising amino acids within the human DLL4 N-terminal region comprising SEQ ID NO: 11. In other embodiments, the anti-DLL4 antibody is a humanized antibody or a human antibody. In a further embodiment, the humanized anti-DLL4 antibody is encoded by the plasmid deposited with ATCC on May 10, 2007, having ATCC deposit number PTA-8425, also known as 21M18 H7L2 and OMP-21M18. In a further embodiment, the humanized anti-DLL4 antibody is encoded by the plasmid deposited with ATCC on May 10, 2007, having ATCC deposit number PTA-8427, also known as 21M18 H9L2. In yet another embodiment, the anti-DLL4 antibody competes with the antibody OMP-21M18 for binding to DLL4.

In certain embodiments, the anti-hypertensive agent is selected from the group consisting of: diuretics, adrenergic receptor antagonists, adrenergic receptor agonists, calcium channel blockers, ACE inhibitors, angiotensin II receptor antagonists, aldosterone antagonists, vasodilators, renin inhibitors, and combinations thereof.

Administration of the DLL4 antagonist and one or more anti-hypertensive agents can be simultaneous or sequential. When administered sequentially, either the DLL4 antagonist or the anti-hypertensive agent can be administered first. In certain embodiments, administration of the DLL4 antagonist and anti-hypertensive agent is chronic; that is, the subject receiving treatment will be given multiple doses of the DLL4 antagonist and the anti-hypertensive agent over an extended period of time.

The subject in need of treatment suffers from cancer and can either suffer from hypertension, be at risk for developing hypertension, or is a subject in which the prevention or inhibition of hypertension is desirable. In certain embodiments, the subject in need of treatment is at risk for cardiovascular disease. In other embodiments, the subject in need of treatment cannot otherwise be treated with an appropriate, effective dose of a DLL4 antagonist without developing hypertension. In other embodiments, the subject does not have a prior history of hypertension and/or cardiovascular disease.

The invention also provides kits comprising a container, wherein the container contains therein a pharmaceutical composition comprising a DLL4 antagonist and a pharmaceutically acceptable carrier, and wherein the container further comprises a package insert indicating that the composition can be used in combination with one or more anti-hypertensive agents. In certain embodiments, the kit comprises an anti-DLL4 antibody and a package insert contained within a container. In other embodiments, the kit comprises an anti-DLL4 antibody, at least one anti-hypertensive agent, and a package insert contained within a container.

Additional objects and advantages of the invention will be set forth in part in the description which follows, and in part will be obvious from the description, or can be learned by practice of the invention. The objects and advantages of the invention will be realized and attained by means of the elements and combinations particularly pointed out in the appended claims. It is to be understood that both the foregoing general description and the following detailed description are exemplary and explanatory only and are not restrictive of the invention, as claimed. In the specification and the appended claims, the singular forms "a," "an," and "the" include plural reference unless the context clearly dictates otherwise.

DESCRIPTION OF THE FIGURES

FIGS. 1A-1B: The Table of FIGS. 1A-1B is a summary of the blood pressure readings and anti-hypertensive treatments of Subject 1, a 78-year-old male with adenocarcinoma of the caecum with metastases to the liver, throughout a Phase I clinical trial of OMP-21M18. Subject 1 was enrolled in the 0.5 mg/kg OMP-21M18 cohort.

FIGS. 2A-2C: The Table of FIGS. 2A-2C is a summary of the blood pressure readings and anti-hypertensive treatments of Subject 2, a 55-year-old male with low-grade leiomyosarcoma, throughout a Phase I clinical trial of OMP-21M18. Subject 2 was enrolled in the 1.0 mg/kg OMP-21M18 cohort.

FIG. 3: The Table of FIG. 3 is a summary of the blood pressure readings and anti-hypertensive treatments of Subject 3, a 64-year-old woman with a choroidal melanoma of the right eye and metastases in both the liver and the lung, throughout a Phase I clinical trial of OMP-21M18. Subject 3 was enrolled in the 2.5 mg/kg OMP-21M18 cohort.

FIG. 4: The Table of FIG. 4 is a summary of the blood pressure readings and anti-hypertensive treatments of Subject 5, a 56-year-old female with stage IV colorectal cancer, throughout a Phase I clinical trial of OMP-21M18. Subject 5 was enrolled in the 10 mg/kg OMP-21M18 cohort.

FIG. 5: The Table of FIG. 5 is a summary of the blood pressure readings and anti-hypertensive treatments of Subject 7, a 71-year-old female with stage IV adenocarcinoma of the rectosigmoid junction, throughout a Phase I clinical trial of OMP-21M18. Subject 7 was enrolled in the 10 mg/kg OMP-21M18 cohort.

FIG. 6: The Table of FIG. 6 is a summary of the blood pressure readings and anti-hypertensive treatments of Subject 8, a 58-year-old man with stage IV colorectal cancer, throughout a Phase I clinical trial of OMP-21M18. Subject 8 was enrolled in the 10 mg/kg OMP-21M18 cohort.

FIG. 7: The Table of FIG. 7 is a summary of the blood pressure readings and anti-hypertensive treatments of Subject 9, a 54-year-old man with locally advanced adenocarcinoma of the head of the pancreas, throughout a Phase I clinical trial of OMP-21M18. Subject 9 was enrolled in the 10 mg/kg OMP-21M18 cohort.

All of the tables in FIGS. 1-7 include the baseline blood pressure of each subject, before the start of treatment with OMP-21M18, and blood pressure readings for each subject for every day of the study that blood pressure readings were taken. For study days in which an infusion of OMP-21M18 was administered, blood pressure readings include a reading pre-infusion, 15 minutes after the start of infusion, at the end of infusion, and 15 minutes post-infusion.

DESCRIPTION OF THE EMBODIMENTS

Definitions

The term "antibody" is used to mean an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. In certain embodiments, antibodies of the present invention include antagonist antibodies that specifically bind to DLL4. Such antibodies can, for example, interfere with ligand binding, receptor dimerization, and/or downstream signaling of the DLL4 receptor.

As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

A "monoclonal antibody" as used herein refers to homogenous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

As used herein, the term "humanized antibody" refers to forms of non-human (e.g. murine) antibodies that are specific immunoglobulin chains, chimeric immunoglobulins, or fragments thereof that contain minimal non-human sequences. Typically, humanized antibodies are human immunoglobulins in which residues from the complementarity determining regions (CDRs) within the antigen determination region (or hypervariable region) of the variable region of an antibody chain or chains are replaced by residues from the CDR of a non-human species (e.g. mouse, rat, rabbit, hamster) that have the desired specificity, affinity, and capability. In some instances, residues from the variable chain framework region (FR) of a human immunoglobulin are replaced with the corresponding residues in an antibody from a non-human species that has the desired specificity, affinity, and capability. The humanized antibody can be further modified by the substitution of additional residues either in the variable framework region and/or within the replaced non-human residues to refine and optimize antibody specificity, affinity, and/or capability. In general, the humanized antibody will comprise substantially all of at least one, and typically two or three or four, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539.

The term "human antibody," as used herein, means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

That an antibody "selectively binds" or "specifically binds" means that the antibody reacts or associates more frequently, more rapidly, with greater duration, with greater affinity, or with some combination of the above to an epitope than with alternative substances, including unrelated proteins. "Selectively binds" or "specifically binds" means that an antibody binds to a protein at times with a $K_D$ of about 0.1 mM or lower, and at other times about 0.01 mM or lower. Because of the sequence identity between homologous proteins in different species, specific binding can include an antibody that recognizes a DLL4 protein in more than one species.

The terms "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

As used herein, the term "hypertension" refers to a condition in which a subject exhibits abnormally elevated blood pressure. Hypertension is classified as either essential hypertension (primary hypertension), in which no specific medical cause for the elevated blood pressure is found, or secondary hypertension, in which elevated blood pressure is due to a specific condition, such as kidney disease or tumors, or due to exposure to a substance that increases blood pressure. In general, hypertension in humans is considered to be present when a person's blood pressure is consistently at least 140 mmHg systolic or 90 mmHg diastolic. Prehypertension is considered to be present when a person's blood pressure is in the range of 120-139 mmHg systolic or 80-89 mmHg diastolic. While not necessarily problematic in itself, prehypertension can indicate that a person is at increased risk for developing hypertension.

As used herein, the term "anti-hypertensive agent" refers to any compound that when administered to a subject reduces blood pressure. In medicine, anti-hypertensive drugs are used to treat hypertension. There are several classes of anti-hypertensive drugs, including diuretics, adrenergic receptor antagonists, adrenergic receptor agonists, calcium channel blockers, ACE inhibitors, angiotensin II receptor antagonists, aldosterone antagonists, vasodilators, and renin inhibitors. Each of these groups of anti-hypertensive drugs acts to reduce blood pressure through a different mechanism.

As used herein, the terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of solid tumor cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, and various types of head and neck cancers.

As used herein, the terms "subject" or "patient" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

"Pharmaceutically acceptable carrier, excipient, or adjuvant" refers to a carrier, excipient, or adjuvant that can be administered to a subject together with the anti-DLL4 antibody and/or one or more anti-hypertensive agent of the invention, and which does not destroy the pharmacological activity thereof and is nontoxic when administered in doses sufficient to deliver a therapeutic amount of the compound. Pharmaceutically acceptable carriers, excipients or adjuvants are often listed in the U.S. Pharmacopeia or other generally recognized pharmacopeia for use in animals, including humans.

The terms "effective amount" or "therapeutically effective amount" refers to an amount of an antibody, polypeptide, polynucleotide, small organic molecule, or other drug effective to "treat" a disease or disorder in a subject or mammal. In the case of cancer, the therapeutically effective amount of the drug can reduce the number of cancer cells; reduce the tumor size; inhibit or stop cancer cell infiltration into peripheral organs including, for example, the spread of cancer into soft tissue and bone; inhibit and stop tumor metastasis; inhibit and stop tumor growth; relieve to some extent one or more of the symptoms associated with the cancer, reduce morbidity and mortality; improve quality of life; or a combination of such effects. To the extent the drug prevents growth and/or kills existing cancer cells, it can be referred to as cytostatic and/or cytotoxic. In the case of hypertension, a therapeutically effective amount of the anti-hypertensive agent can reduce the blood pressure of a subject or prevent a subject's blood pressure from rising. Preferably, the therapeutically effective amount of the anti-hypertensive agent will reduce a subject's blood pressure to clinically defined "normal" levels or maintain a subject's blood pressure within normal bounds.

Terms such as "treating" or "treatment" or "to treat" or "alleviating" or "to alleviate" or "ameliorating" or "to ameliorate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus those in need of treatment include those already with the disorder; those prone to have the disorder; and those in whom the disorder is to be prevented. In certain embodiments, a subject is successfully "treated" according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; a reduction in blood pressure or stable maintenance of blood pressure at or about clinically normal levels; or some combination of effects.

DLL4 Antibodies

In certain embodiments, the DLL4 antagonists are antibodies, such as antibodies that bind specifically to DLL4 (i.e., anti-DLL4 antibodies). In certain embodiments, the antibodies specifically bind human DLL4.

Anti-DLL4 antibodies can act as DLL4 antagonists by binding to DLL4 and blocking its binding to the Notch receptor. The DLL4 antibodies of the invention can be prepared by any conventional means known in the art. In certain embodiments, the Dll4 antibodies are dysangiogenic.

In certain embodiments, the anti-DLL4 antibody is a monoclonal antibody. Monoclonal antibodies can be prepared by any conventional means known in the art (Goding, Monoclonal Antibodies: Principles and Practice, Academic Press, 1986). Monoclonal antibodies can be prepared using hybridoma methods, such as those described by Kohler and Milstein (1975) Nature 256:495. Alternatively, monoclonal antibodies can also be made using recombinant DNA methods as described in U.S. Pat. No. 4,816,567. Recombinant monoclonal antibodies or fragments thereof of the desired species can also be isolated from phage display libraries expressing CDRs of the desired species as described (Mc-Cafferty et al., 1990, Nature, 348:552-554; Clackson et al., 1991, Nature, 352:624-628; and Marks et al., 1991, J. Mol. Biol., 222:581-597).

In some embodiments of the present invention, the anti-DLL4 antibody is a humanized antibody. Humanized antibodies are antibodies that contain minimal sequences from non-human (e.g murine) antibodies within the variable regions. Such antibodies are used therapeutically to reduce antigenicity and HAMA (human anti-mouse antibody) responses when administered to a human subject. Humanized antibodies can be produced using various techniques known in the art (Jones et al., 1986, Nature, 321:522-525; Riechmann et al., 1988, Nature, 332:323-327; Verhoeyen et al., 1988, Science, 239:1534-1536). An antibody can be humanized by substituting the CDRs of a human antibody with that of a non-human antibody (e.g. mouse, rat, rabbit, hamster, etc.) having the desired specificity, affinity, and/or capability. The humanized antibody can be further modified by the substitution of additional residue either in the variable human framework region and/or within the replaced non-human residues to refine and optimize antibody specificity, affinity, and/or capability.

In other embodiments, the anti-DLL4 antibody is a fully human antibody. Human antibodies can be prepared using various techniques known in the art Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373). Also, the human antibody can be selected from a phage library, where that phage library expresses human antibodies (Vaughan et al., 1996, Nat. Biotech., 14:309-314; Sheets et al., 1998, Proc. Nat'l. Acad. Sci., 95:6157-6162; Hoogenboom and Winter, 1991, J. Mol. Biol., 227:381; Marks et al., 1991, J. Mol. Biol., 222:581). Human antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In certain embodiments, the anti-DLL4 antibody specifically binds to a human DLL4 epitope in the amino-terminal region (SEQ ID NO: 11). In certain embodiments, the anti-Dll4 antibody binds to the DSL domain. In certain embodiments, the anti-Dll4 antibody binds to both the DSL domain and/or the amino-terminal region of Dll4.

In certain embodiments, the anti-DLL4 antibody is the antibody produced by the hybridoma deposited with ATCC on Sep. 28, 2007 and having ATCC deposit number PTA-8670, also known as murine 21M18. The murine 21M18 antibody is described in detail in U.S. Pat. No. 7,750,124, Filed Sep. 28, 2007, and published as U.S. Patent Application Pub. No. 2008/0187532, incorporated herein by reference in its entirety.

In certain embodiments, the anti-DLL4 antibody is the antibody encoded by the plasmid deposited with ATCC, 10801 University Boulevard, Manassas, Va., USA, on May 10, 2007, having ATCC deposit number PTA-8425, also known as 21M18 H7L2 and OMP-21M18. The OMP-21M18 antibody is described in detail in U.S. Pat. No. 7,750,124, Filed Sep. 28, 2007, and published as U.S. Patent Application Pub. No. 2008/0187532. The anti-DLL4 antibody OMP-21M18 comprises a heavy chain variable region comprising CDR amino acid sequences CDR1 (SEQ ID NO: 1); CDR2 (SEQ ID NO: 2, SEQ ID NO: 3, or SEQ ID NO: 4); and CDR3 (SEQ ID NO: 5); and a light chain variable region comprising CDR amino acid sequences CDR1 (SEQ ID NO: 7); CDR2 (SEQ ID NO: 8); and CDR3 (SEQ ID NO: 9). In one embodiment, the OMP-21M18 antibody comprises the heavy chain sequence of SEQ ID NO:6 and the light chain sequence of SEQ ID NO: 10.

In certain embodiments, the anti-DLL4 antibody is the antibody encoded by the plasmid deposited with ATCC on May 10, 2007, having ATCC deposit number PTA-8427, also known as 21M18 H9L2. The 21M18 H9L2 antibody is described in detail in U.S. Pat. No. 7,750,124, Filed Sep. 28, 2007, and published as U.S. Patent Application Pub. No. 2008/0187532.

In certain embodiments, the anti-DLL4 antibody is an antibody that competes with the antibody OMP-21M18 for specific binding to human DLL4.

Other anti-DLL4 antibodies are known in the art. Anti-DLL4 antibodies are available from commercial sources (for example, Santa Cruz Biotechnology, Inc. catalog no. sc-73900 is a rat $IgG_{2a}$ antibody that binds to the extracellular domain of human DLL4). In some embodiments, the DLL4 antagonist can be one of the anti-DLL4 antibodies described in U.S. Pat. No. 7,919,593, filed Dec. 14, 2007, and published as U.S. Patent Application Pub. No. 2008/0181899; U.S. Pat. No. 7,488,806, filed Oct. 3, 2008, and published as U.S. Patent Application Pub. No. 2009/0017035; and U.S. Pat. No. 7,534,868, filed Feb. 13, 2009, and published as U.S. Patent Application Pub. No. 2009/0142354. The foregoing patents and applications disclose fully human anti-DLL4 antibodies generated using VELOCIMMUNE™ technology (Regeneron Pharmaceuticals, Inc.). Certain of these antibodies, denoted REGN281, REGN 421, and REGN 422 are described as blocking DLL4 binding to the Notch receptor.

In other embodiments, the DLL4 antagonist can be one of the anti-DLL4 antibodies described in U.S. Pat. No. 7,803,377, filed Jun. 6, 2007, and published as U.S. Patent Application Pub. No. 2008/0175847; and U.S. patent application Ser. No. 11/759,093, filed Jun. 6, 2007, and published as U.S. Patent Application Pub. No. 2008/0014196 (now abandoned). The foregoing applications disclose human anti-DLL4 antibodies that are described as binding to the extracellular domain of DLL4. These antibodies were isolated by screening a synthetic phage antibody library (Genentech, Inc.).

Anti-Hypertensive Agents

The anti-hypertensive agents useful in the present invention fall into several classes, including: diuretics, adrenergic receptor antagonists, adrenergic receptor agonists, calcium channel blockers, Angiotensin-Converting Enzyme (ACE) inhibitors, angiotensin II receptor antagonists, aldosterone antagonists, vasodilators, and renin inhibitors.

Diuretics are a class of drugs that elevate the rate of urination and thus provides a means of forced diuresis. There are several categories of diuretics, including high ceiling loop diuretics, thiazides, potassium-sparing diuretics, calcium-sparing diuretics, osmotic diuretics, and low ceiling diuretics. All diuretics increase the excretion of water from the body, although each class does so in a distinct way. Diuretics include but are not limited to: loop diuretics such as furosemide, bumetanide, ethacrynic acid, and torsemide; thiazide diuretics such as epitizide, hydrochlorothiazide, hydroflumethiazide, chlorothiazide, bendroflumethiazide, polythiazide, trichlormethiazide, cyclopenthiazide, methyclothiazide, cyclothiazide, mebutizide, and other benzothiadiazine derivatives; thiazide-like diuretics such as indapamide, chlortalidone, metolazone, quinethazone, clopamide, mefruside, clofenamide, meticrane, xipamide, clorexolone, and fenquizone; potassium-sparing diuretics such as amiloride, triamterene, eplerenone, benzamil, potassium canrenoate, canrenone, and spironolactone; osmotic diuretics such as mannitol, glucose, and urea; vasopressin receptor antagonists such as conivaptan, relcovaptan, nelivaptan, lixivaptan, mozavaptan, satavaptan, tolvaptan, and demeclocycline; mercurial diuretics such as mersalyl acid (Mersal), meralluride, mercaptomerin, mercurophylline, merethoxylline procaine, and calomel; xanthine diuretics such as caffeine, theobromine, paraxanthine, and theophylline; carbonic anhydrase inhibitors such as acetazolamide, methazolamide, dorzolamide, sulfonamide, and topiramate; other diuretics such as diuretic purines, diuretic steroids, diuretic sulfonamide derivatives, diuretic uracils, amanozine, arbutin, chlorazanil, etozolin, hydracarbazine, isosorbide, metochalcone, muzolimine, perhexiline, ticrynafen, triamterene, and spironolactone.

Adrenergic receptor antagonists can be divided into two sub-categories: beta-adrenergic antagonists ("beta blockers") and alpha-adrenergic antagonists ("alpha blockers"). Adrenergic receptor antagonists include but are not limited to: beta-adrenergic antagonists such as atenolol, metoprolol, nadolol, oxprenolol, pindolol, propranolol, timolol, acebutolol, bisoprolol, esmolol, labetalol, carvedilol, bucindolol, nebivolol, alprenolol; amosulalol, arotinolol, befunolol, betaxolol, bevantolot, bopindolol, bucumolol, bufetolol, bufuralol, bunitrolol, bupranolol, butidrine hydrochloride, butofilolol, carazolol, carteolol, celiprolol, cetamolol, cloranololdilevalol, epanolol, indenolol, levobunolol, mepindolol, metipranolol, moprolol, nadoxolol, nipradilol, penbutolol, practolol, pronethalol, sotalol, sulfinalol, talinolol, tertatolol, tilisolol, toliprolol, and xibenolol; and alpha-adrenergic antagonists such as phenoxybenzamine, prazosin, doxazosin, terazosin, trimazosin, phentolamine, amosulalol, arotinolol, dapiprazole, fenspiride, indoramin, labetalol, naftopidil, nicergoline, tamsulosin, tolazoline, reserpine, moxonidine and yohimbine.

Adrenergic receptor agonists include but are not limited to: clonidine, methyldopa, guanfacine, methoxamine, methylnorepinephrine, oxymetazoline, phenylephrine, guanabenz, guanoxabenz, guanethidine, xylazine, and tizanidine.

Calcium channel blockers block voltage-gated calcium channels in cardiac muscle and blood vessels, leading to a reduction in muscle contraction. This leads to vasodilation and a decrease in blood pressure. Calcium channel blockers include but are not limited to: dihydropyridines such as amlodipine, felodipine, nicardipine, nifedipine, nimodipine, isradipine, nitrendipine, aranidipine, barnidipine, benidipine, cilnidipine, efonidipine, elgodipine, lacidipine, lercanidipine, manidipine, nilvadipine, and nisoldipine; and non-dihydropyridines such as diltiazem, verapamil, bepridil, clentiazem, fendiline, gallopamil, mibefradil, prenylamine, semotiadil, terodiline, cinnarizine, flunarizine, lidoflazine, lomerizine, bencyclane, etafenone, and perhexiline.

Angiotensin-Converting Enzyme (ACE) inhibitors treat hypertension by lowering arteriolar resistance and increasing venous capacity, increasing cardiac output and cardiac index, stroke work and volume, lowering renovascular resistance, and increasing excretion of sodium in the urine. ACE inhibitors include but are not limited to: sulfhydryl-containing agents such as captopril and zofenopril; dicarboxylate-containing agents such as enalapril, ramipril, quinapril, perindopril, lisinopril, and benazepril; phosphonate-containing agents such as fosinopril and ceronapril, naturally occurring ACE inhibitors such as casokinins, lactokinins; tripeptides such as Val-Pro-Pro and Ile-Pro-Pro and the nonapeptide teprotide; and other ACE inhibitors such alacepril, cilazapril, delapril imidapril moexipril, rentiapril, spirapril, temocapril, moveltipril and trandolapril.

Angiotensin II receptor antagonists block the activation of angiotensin II $AT_1$ receptors, causing vasodilation, reduced secretion of vasopressin, and reduced production and secretion of aldosterone, which results in the reduction of blood pressure. Angiotensin II receptor antagonists include but are not limited to: candesartan, eprosartan, irbesartan, losartan, olmesartan, telmisartan, and valsartan.

Aldosterone antagonists block the mineralocorticoid receptor resulting in inhibition of sodium resorption in the collecting duct of the nephron in the kidneys. This interferes with sodium/potassium exchange, reducing urinary potassium excretion and weakly increasing water excretion, leading to a diuretic effect. Aldosterone antagonists include but are not limited to: eplerenone, canrenone, and spironolactone.

Vasodilators work by a wide variety of mechanisms, but all lead to the relaxation of smooth muscle cells within blood vessel walls, and thus the widening of blood vessels. The widening of blood vessels leads to increased blood flow and reduced vascular resistance, and therefore lower blood pressure. Vasodilators include but are not limited to: cerebral vasodilators such as bencyclane, cinnarizine, citicoline, cyclandelate, ciclonicate, diisopropylamine dichloroacetate, eburnamonine, fasudil, fenoxedil, flunarizine, ibudilast, ifenprodil, lomerizine, nafronyl, nicametate, nicergoline, nimodipine, papaverine, tinofedrine, vincamine, vinpocetine, and viquidil; coronary vasodilators such as amotriphene, bendazol, benfurodil hemisuccinate, benziodarone, chloracizine, chromonar, clobenfural, clonitrate, cloricromen, dilazep, dipyridamole, droprenilamine, efloxate, erythrityl tetranitrate, etafenone, fendiline, floredil, ganglefene, hexestrol bis($\beta$-diethylaminoethyl) ether, hexobendine, itramin tosylate, khellin, lidoflazine, mannitol hexanitrate, medibazine, nitroglycerin, pentaerythritol tetranitrate, pentrinitrol, perhexiline, pimefylline, prenylamine, propatyl nitrate, trapidil, tricromyl, trimetazidine, trolnitrate phosphate, sildenafil, tadalafil, vardenafil, sodium nitroprusside, isosorbide mononitrate, isosorbide dinitrate, pentaerythritol tetranitrate, theobromine, and visnadine; and peripheral vasodilators such as aluminium nicotinate, bamethan, bencyclane, betahistine, bradykinin, brovincamine, bufeniode, buflomedil, butalamine, cetiedil, ciclonicate, cinepazide, cinnarizine, cyclandelate, diisopropylamine dichloroacetate, eledoisin, fenoxedil, flunarizine, hepronicate, ifenprodil, iloprost, inositol niacinate, isoxsuprine, kallidin, kallikrein, moxisylyte, nafronyl, nicametate, nicergoline, nicofuranose, nylidrin, pentifylline, pentoxifylline, piribedil, prostaglandin E1, suloctidil, tolazoline, and xanthinol niacinate.

Renin inhibitors act on the juxtaglomerular cells of kidney, which produce renin in response to decreased blood flow. Renin inhibitors include but are not limited to: aliskiren and remikiren.

Other anti-hypertensives, not listed above, are also contemplated for use in the invention. A skilled artisan would recognize that any compound that acts to reduce blood pressure when administered to a subject could be used as the anti-hypertensive agent of the present invention.

Pharmaceutical Composition

The pharmaceutical compositions of the present invention comprise an anti-DLL4 antibody and one or more anti-hypertensive agents. The pharmaceutical compositions of the present invention can be prepared for storage and use by combining an anti-DLL4 antibody and one or more anti-hypertensive agent with a pharmaceutically acceptable carrier (e.g. a vehicle or excipient). In other embodiments, the anti-DLL4 antibody and the one or more anti-hypertensive agents are in separate compositions, wherein those compositions are each formulated with pharmaceutically acceptable carriers appropriate for each agent.

Examples of suitable pharmaceutical carriers are described in "Remington, The Science and Practice of Pharmacy 20th Edition Mack Publishing, 2000." Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN, polyethylene glycol (PEG), or polysorbate surfactants such as Polysorbate 20.

The pharmaceutical compositions of the present invention can be formulated for systemic or local administration. Examples of routes of administration include parenteral (e.g., intravenous, intradermal, subcutaneous), oral (e.g., inhalation), transmucosal, and rectal administration.

Pharmaceutical compositions suitable for parenteral administration include sterile aqueous solutions (where water soluble) or dispersions and sterile powders for the extemporaneous preparation of sterile injectable solutions or dispersion. For intravenous administration, suitable carriers include water for injection, physiological saline, bacteriostatic water, Cremophor EL (BASF, Parsippany, N.J.), phosphate buffered saline (PBS), fixed oils, ethanol, polyethylene glycols, glycerine, propylene glycol or other synthetic solvents. In all cases, the composition must be sterile and should be fluid to the extent that easy syringeability exists. The proper fluidity can be maintained, for example, by the use of a coating such as lecithin, by the maintenance of the required particle size in the case of a dispersion, and by the use of surfactants. The pharmaceutical composition must be stable under the conditions of manufacture and storage and must be preserved against the contaminating action of microorganisms such as bacteria and fungi. Prevention of the action of microorganisms can be achieved by various antibacterial and antifungal agents, for example, benzyl alcohol, parabens, chlorobutanol, phenol, antioxidants such as ascorbic acid or sodium bisulfite, chelating agents such as ethylenediaminetetraacetic acid, thimerosal, and the like. In many cases, it will be preferable to include isotonic agents such as sugars, polyalcohols such as mannitol and sorbitol, or sodium chloride in the composition. Prolonged absorption of the injectable compositions can be brought about by including in the composition an agent which delays absorption, for example, aluminum monostearate and gelatin. The pH can be adjusted with acids or bases, such as hydrochloric acid or sodium hydroxide. The parenteral preparation is enclosed in ampoules, disposable syringes or multiple dose vials made of glass or plastic.

Sterile injectable solutions are prepared by incorporating the active compound (e.g., an anti-DLL4 antibody and an anti-hypertensive agent) in the required amount in an appropriate solvent with one or a combination of ingredients enumerated above, as required, followed by filter sterilization. Generally, dispersions are prepared by incorporating the active compounds into a sterile vehicle that contains a basic dispersion medium and the required other ingredients from those enumerated above. In the case of sterile powders for the preparation of sterile injectable solutions, methods of preparation are vacuum drying and freeze-drying that yield a powder of the active ingredient plus any additional desired ingredient from a previously sterile-filtered solution thereof.

In certain embodiments, the anti-DLL4 antibody can be prepared for use at a concentration of 10 mg/mL in a solution of 50 mM histidine, 100 mM sodium chloride, 45 mM sucrose, and 0.01% (w/v) Polysorbate 20, and the pH adjusted to 6.0.

The pharmaceutical compositions of the invention can include the anti-DLL4 antibody and/or anti-hypertensive agent complexed with liposomes (Epstein, et al., 1985, Proc. Natl. Acad. Sci. USA 82:3688; Hwang, et al., 1980, Proc. Natl. Acad. Sci. USA 77:4030; and U.S. Pat. Nos. 4,485,045 and 4,544,545). Liposomes with enhanced circulation time are disclosed in U.S. Pat. No. 5,013,556. Some liposomes can be generated by the reverse phase evaporation with a lipid composition comprising phosphatidylcholine, cholesterol, and PEG-derivatized phosphatidylethanolamine (PEG-PE). Liposomes are extruded through filters of defined pore size to yield liposomes with the desired diameter.

The anti-DLL4 antibody and/or the anti-hypertensive agent can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions as described in "Remington, The Science and Practice of Pharmacy 20th Ed. Mack Publishing (2000)."

In addition sustained-release preparations can be prepared. Suitable examples of sustained-release preparations include semipermeable matrices of solid hydrophobic polymers containing the anti-DLL4 antibody and/or the anti-hypertensive agent, which matrices are in the form of shaped articles (e.g. films, or microcapsules). Examples of sustained-release matrices include polyesters, hydrogels such as poly(2-hydroxyethyl-methacrylate) or poly(vinylalcohol), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

Oral compositions generally include an inert diluent or an edible carrier. They can be enclosed in gelatin capsules or compressed into tablets. For the purpose of oral therapeutic administration, the active compound is incorporated with excipients and used in the form of tablets, troches, or capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. The tablets, pills, etc of the novel composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials including a number of polymeric acids and mixtures of polymeric acids with such materials as shellac, cetyl alcohol and cellulose acetate.

For administration by inhalation, the compounds are delivered in the form of an aerosol spray from a pressured container or dispenser which contains a suitable propellant, e.g., a gas such as carbon dioxide, or a nebulizer.

Administration can also be transmucosal or transdermal. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Combination Therapies

In certain embodiments, the anti-DLL4 antibody and the anti-hypertensive agent can be administered in combination with one or more additional compounds or therapies for the treatment of cancer. Such additional anti-cancer compounds include: cytotoxic agents, chemotherapeutic agents, growth inhibitory agents, or therapeutic antibodies. Where separate pharmaceutical compositions are used, the anti-DLL4 antibody and one or more additional agents can be administered concurrently, or sequentially.

"Cytotoxic agents" inhibit or prevent the function of cells and/or causes destruction of cells. Cytotoxic agents include but are not limited to: radioactive isotopes (e.g. $I^{131}$, $I^{125}$, $I^{90}$ and $Re^{186}$), and toxins such as enzymatically active toxins of bacterial, fungal, plant or animal origin, or fragments thereof.

"Chemotherapeutic agents" are chemical compounds useful in the treatment of cancer. Chemotherapeutic agents include but are not limited to: alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil; folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; capecitabine; ibandronate; CPT-11; topoisomerase inhibitor RFS 2000; difluoromethylornithine; retinoic acid; esperamicins; capecitabine; and pharmaceutically acceptable salts, acids or derivatives of any of the above. Also included are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onaprostone, and toremifene (Fareston); and anti-androgens such as flutamide, nilutamide, bicalutamide, leuprolide, and goserelin; and pharmaceutically acceptable salts, acids or derivatives of any of the above.

"Growth inhibitory agents" are compounds which inhibit growth of cells, especially cancer cells, either in vitro or in vivo. Growth inhibitory agents include but are not limited to: agents that block cell cycle progression, such as vincas (vincristine and vinblastine), TAXOL™, and topo II inhibitors such as doxorubicin, epirubicin, daunorubicin, etoposide, bleomycin, DNA alkylating agents such as tamoxifen, prednisone, dacarbazine, mechlorethamine, cisplatin, methotrexate, 5-fluorouracil, and ara-C.

"Therapeutic antibodies" include antibodies that are used to specifically target cancer cells. Therapeutic antibodies include but are not limited to: rituximab (Rituxan), cetuximab (Erbitux), ibritumomab (Zevalin), gemtuzumab (Mylotarg), trastuzumab (Herceptin), alemtuzumab (Campath), bevacizumab (Avastin), panitumumab (Vectibix), and tositumomab (Bexxar).

Methods of Administration

In order to control hypertension in subjects having the condition or at risk for it, it can be desirable to co-administer the anti-DLL4 antibody and one or more anti-hypertensive agent. In one embodiment, the use of the anti-DLL4 antibody and one or more anti-hypertensive agent is directed for those subjects having hypertension or at risk for its development.

The pharmaceutical composition of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal, intraocular or intramuscular injection or infusion; or intracranial (e.g., intrathecal or intraventricular) administration. The pharmaceutical composition of the invention can be administered by any convenient route, such as infusion or bolus injection.

Administration can be acute (i.e., a single administration of the composition) or chronic (i.e., daily, weekly, monthly administration).

Administration of the anti-DLL4 antibody and the anti-hypertensive agent can include co-administration, either in a single pharmaceutical formulation or using separate formulations, or consecutive administration in either order but generally within a time period such that all active agents can exert their biological activities simultaneously. Preparation and dosing schedules for anti-hypertensive agents can be used according to manufacturers' instructions or as determined empirically by the skilled practitioner.

For the treatment of cancer with an anti-DLL4 antibody, the appropriate dosage of the anti-DLL4 antibody can be determined by the treating physician. The size of a tumor, the presence of malignant disease, and the extent of metastasis are factors to be considered when determining a dosage. The anti-DLL4 antibody can be administered one time or over a series of treatments lasting from several days to several months. Preferably, the anti-DLL4 antibody is administered chronically until a cure is effected or a diminution of the disease state is achieved (e.g. reduction in tumor size). Optimal dosing schedules can be calculated from measurements of drug accumulation in the body of the patient and will vary depending on the relative potency of the individual anti-DLL4 antibody. The administering physician can easily determine optimum dosages, dosing methodologies and repetition rates. In general, dosage is from 0.01 μg to 100 mg per kg of body weight, and can be given once or more daily, weekly, monthly or yearly. Repetition rates can be estimated for dosing based on measured residence times and concentrations of the drug in bodily fluids or tissues. The treating physician can monitor the disease state of the patient (i.e., increases or decreases in tumor size, presence or spread of metastasis, appearance of malignancies, quality of life) and adjust the dosage of the anti-DLL4 antibody accordingly.

For treatment of cancer with an anti-DLL4 antibody, such as OMP-21M18, in certain embodiments, suitable dosages for intravenous administration are between about 0.1 mg/kg and about 20 mg/kg. In certain embodiments, dosages of the anti-DLL4 antibody, such as OMP-21M18, are about 0.1 mg/kg; about 0.2 mg/kg; about 0.5 mg/kg; about 1.0 mg/kg; about 2.5 mg/kg; about 5.0 mg/kg; about 7.5 mg/kg; about 10 mg/kg; and about 15 mg/kg. Administration can be daily, twice per week, once per week, once every other week, once every three weeks, monthly, or any other suitable interval at the discretion of the treating physician. Dosages and intervals of administration can be adjusted to optimize treatment efficacy.

For the treatment of hypertension, the appropriate dosage of the anti-hypertensive agent depends on the severity and course of the hypertension, the responsiveness of the subject, whether the anti-hypertensive is administered for therapeutic or preventative purposes, the subject's previous therapy, the subject's clinical history, and so on, at the discretion of the treating physician. The anti-hypertensive agent can be administered one time or over a series of treatments lasting from several days to several months. Preferably, the anti-hypertensive agent is administered chronically until treatment with the anti-DLL4 antibody has ceased. Optimal dosing schedules can be calculated from measurements of drug accumulation in the body of the patient and will vary depending on the relative potency of the individual anti-hypertensive agent. Additionally, effective dosages for anti-hypertensive agents available commercially will be provided by the manufacturer. The administering physician can easily determine optimum dosages, dosing methodologies and repetition rates. In general, dosage is from 0.01 μg to 100 mg per kg of body weight, and can be given once or more daily, weekly, monthly or yearly. The treating physician can estimate repetition rates for dosing based on measured residence times and concentrations of the drug in bodily fluids or tissues. Furthermore, the treating physician can monitor the blood pressure of a subject and adjust the amount of an anti-hypertensive administered, the frequency of dosing, or the particular anti-hypertensive used to suit the needs of the patient. In a human clinical setting non-invasive methods for measuring blood pressure would be used. For example, a simple arm cuff or sphygmomanometer measure blood pressure directly using the oscillometric method or connected to a pulse transducer for continuous measurement. More than one anti-hypertensive medication can be used concurrently to effectively control hypertension in a subject receiving treatment with an anti-DLL4 antibody.

The present invention provides methods of preventing hypertension in a patient receiving treatment with a DLL4 antagonist or an anti-DLL4 antibody comprising administering to the patient an effective amount of one or more anti-hypertensive agents. "Preventing hypertension" means that the patient's blood pressure is kept, on average, below the range considered to be hypertension throughout the course of treatment with the DLL4 antagonist or anti-DLL4 antibody. A blood pressure consistently at or above 140 mmHg systolic or 90 mmHg diastolic is considered hypertension. A blood pressure consistently in the range of 120-139 mmHg systolic or 80-89 diastolic is considered pre-hypertension. Depending on the tolerances of the treating physician, "preventing hypertension" can mean keeping a patient's blood pressure below the range considered hypertension, or keeping a patient's blood pressure below the range considered pre-hypertension.

The present invention provides methods for monitoring a patient receiving treatment with a DLL4 antagonist or an anti-DLL4 antibody for the development of hypertension comprising measuring the blood pressure of the patient receiving treatment with the DLL4 antagonist or anti-DLL4 antibody for a blood pressure elevated above the normal range and administering to the patient with the elevated blood pressure one or more anti-hypertensive agents. The treating physician can measure the patient's blood pressure before, during, and after treatment with the DLL4 antagonist or anti-DLL4 antibody. Blood pressure measurement before treatment can be used to establish a baseline blood pressure. If the baseline blood pressure is in the pre-hypertensive or hypertensive range, the treating physician can opt to begin administration of anti-hypertensive agents immediately, either before or concurrently with the administration of the DLL4 antagonist or anti-DLL4 antibody. Blood pressure monitoring of the patient would continue after initiation of treatment with the DLL4 antagonist or anti-DLL4 antibody to ensure that the anti-hypertensive regimen is adequately controlling the patient's hypertension. If the baseline blood pressure is in the normal range, the treating physician can opt to continue monitoring blood pressure after treatment with the DLL4 antagonist or anti-DLL4 antibody begins and initiating treatment with anti-hypertensives only if the patient's blood pressure rises. Alternatively, the treating physician can decide to prophylactically administer anti-hypertensives to a patient whose baseline blood pressure is in the normal range to pre-empt the development of hypertension after treatment with the DLL4 antagonist or anti-DLL4 antibody begins.

After treatment with the DLL4 antagonist or anti-DLL4 antibody is initiated, routine monitoring of the patient's blood pressure is performed. Blood pressure readings can be taken at any appropriate interval: daily, every other day, bi-weekly, weekly, biweekly, monthly, or at any interval deemed appropriate by the physician. If the blood pressure of a patient becomes elevated into the hypertension range, the treating physician can initiate anti-hypertensive treatment. The dosages, particular anti-hypertensive medications used, and dosing schedule can be adjusted by the physician as necessary to adequately control the patient's hypertension. If the blood pressure of a patient becomes elevated into the pre-hypertension range, the treating physician can initiate anti-hypertensive treatment or continue monitoring the patient and begin anti-hypertensive treatment only if the patient's blood pressure rises into the hypertension range. If the blood pressure of a patient becomes elevated significantly compared to the baseline blood pressure reading, but is not in the pre-hypertension or hypertension range, the treating physician can prophylactically initiate anti-hypertensive treatment to prevent the patient's blood pressure from continuing to rise, or continue monitoring the patient and begin anti-hypertensive treatment only if the patient's blood pressure rises into the pre-hypertension or hypertension range. If a patient is initiated on anti-hypertensive treatment and their blood pressure does not decrease or continues to rise, the treating physician can increase the dosage of the anti-hypertensive, add one or more additional anti-hypertensive medications to the treatment regimen, change the anti-hypertensive medication, or take more than one of the preceding steps in order to reduce the patient's blood pressure to an acceptable level.

Treatment Population

The pharmaceutical compositions and methods of the present invention can be used to treat subjects suffering from cancer. In certain embodiments, the methods of the invention allow the treatment of subjects suffering from cancer with an anti-DLL4 antibody at a dosage that could not otherwise be used without placing certain subjects at risk for developing complications due to hypertension.

In certain embodiments, the subjects are those suffering from hypertension or pre-hypertension prior to the start of therapy with an anti-DLL4 antibody, subjects over the age of 65 years old, subjects with or at risk for developing cardiovascular disease, or subjects who develop hypertension or pre-hypertension after the start of treatment with an anti-DLL4 antibody.

Subjects at risk for developing cardiovascular disease include those over 65 years of age, of the male sex, or who have hereditary factors linked to cardiovascular disease. The risk of cardiovascular disease increases with increasing age. Over 83 percent of people who die of coronary heart disease are 65 or older. Men overall have a higher risk of cardiovascular disease than women, and experience heart attacks earlier in life. Children of parents who had cardiovascular disease are more likely than children of parents who did not have cardiovascular disease to develop cardiovascular disease themselves, suggesting a hereditary link. Additionally, people of certain races are more likely to develop cardiovascular disease than other races. For example, African Americans, Mexican Americans, native Hawaiians, and American Indians have a greater risk of developing cardiovascular disease than Caucasians.

Additionally, lifestyle factors can contribute to a subject's likelihood of developing cardiovascular disease. Smoking, physical inactivity, excessive drinking of alcohol, high levels of stress, and obesity all increase a subject's likelihood of developing cardiovascular disease. Preexisting conditions can also increase a subject's likelihood of developing cardiovascular disease. Diabetes mellitus, high blood cholesterol, high blood pressure, and clogged arteries are all risk factors for cardiovascular disease.

Subjects at risk for developing hypertension include those subjects over 45 years of age, male subjects, or those with hereditary traits linked to hypertension. The risk of hypertension increases with age. Males over 45 years of age and women over 55 years of age are at an increased risk of developing hypertension. Additionally, men overall have a higher risk of hypertension than women.

Subjects whose blood pressure is in the range considered to be "pre-hypertension" are more likely than subjects whose blood pressure is in the normal range to develop hypertension.

The prevention or inhibition of hypertension is desirable in any subject receiving treatment with a DLL4 antagonist or anti-DLL4 antibody. Prevention or treatment of hypertension is particularly desirable in subjects who, prior to the start of treatment with a DLL4 inhibitor or anti-DLL4 antibody suffer from hypertension or pre-hypertension, are at risk for developing cardiovascular disease, are at risk for developing hypertension, or have a condition which would be exacerbated by hypertension, such as heart failure, aneurysms, kidney disease, or narrowed arteries.

In certain embodiments, the subjects to be treated with a Dll4 antagonist do not have a prior history of hypertension. In certain alternative embodiments, the subjects do not have a prior history of cardiovascular disease. Methods of monitoring such subjects for the development of hypertension, optionally followed by the subsequent administration of anti-hypertensives if hypertension does develop, are provided.

Methods of screening patients for treatment with a Dll4 antagonist, such as an anti-D114 antibody, are also provided. In certain embodiments, the methods comprise selecting patients based on a lack of prior history of hypertension and/or cardiovascular disease. Thus, in certain methods, the subjects having no prior history of hypertension (and/or cardiovascular disease) are treated with the Dll4 antagonist. In certain alternative embodiments, subjects having a prior history of hypertension and/or cardiovascular disease are selected for treatment with both a Dll4 antagonist and an anti-hypertensive.

The invention is not limited to the treatment of tumors or cancer, and includes other, non-malignant diseases that are characterized by the presence of vascular proliferation. Vascular Proliferation disorders include those of the eye such as Macular Degeneration and Diabetic Retinopathy.

Kits

The invention also provides kits comprising an anti-DLL4 antibody and anti-hypertensive agent and that can be used to perform the methods described herein. In certain embodiments, the kit comprises an anti-DLL4 antibody and a package insert contained within a packaging material. In other embodiments, the kit comprises an anti-DLL4 antibody, at least one anti-hypertensive agent, and a package insert contained within a packaging material. The anti-DLL4 antibody and the one or more anti-hypertensive agents can be admixed together in a single pharmaceutical composition for concomitant administration, or can be in separate containers for sequential or concomitant administration. In other embodiments, the kit can also comprise one or more additional anti-cancer therapeutic agents, such as a chemotherapeutic or a therapeutic antibody. In certain embodiments, the package insert will indicate that the anti-DLL4 antibody can be used for treating cancer or reducing tumor growth, that the anti-hypertensive agent can be used in combination with the anti-DLL4 antibody to reduce hypertension caused by the administration of the anti-DLL4 antibody, or contain instructions on the dosage, administration schedule, and monitoring of subjects undergoing treatment with the anti-DLL4 antibody and anti-hypertensive agent. One skilled in the art will readily recognize that the disclosed pharmaceutical compositions of the present invention can be readily incorporated into one of the established kit formats which are well known in the art.

Embodiments of the present disclosure can be further defined by reference to the following examples. It will be apparent to those skilled in the art that many modifications, both to materials and methods, can be practiced without departing from the scope of the present disclosure. As used herein and in the appended claims, the singular forms "a," "or," and "the" include plural referents unless the context clearly dictates otherwise. Thus, for example, reference to "an anti-hypertensive agent" includes a plurality of such agents or equivalents thereof known to those skilled in the art. Furthermore, all numbers expressing quantities of ingredients, dosage amounts, blood pressure readings, and so forth, used in the specification, are modified by the term "about," unless otherwise indicated. Accordingly, the numerical parameters set forth in the specification and claims are approximations that can vary depending upon the desired properties of the present invention.

EXAMPLES

Example 1: Phase 1 Dose Escalation Study of OMP-21M18 in Subjects with Solid Tumors Thirty-three subjects with advanced solid tumors initiated treatment with OMP-21M18 in a Phase I clinical trial. The trial was designed to determine the maximum tolerated dose (MTD), safety, pharmacokinetics, immunogenicity, and preliminary efficacy of OMP-21M18 in subjects with advanced solid tumors. All subjects had histologically confirmed malignancies that were metastatic or unresectable and had received extensive treatment for their cancer. At the time of enrollment, there was no remaining standard curative therapy and no therapy with a demonstrated survival benefit.

OMP-21M18 was prepared for use at a concentration of 10 mg/mL in a solution of 50 mM histidine, 100 mM sodium chloride, 45 mM sucrose, and 0.01% (w/v) Polysorbate 20, with the pH adjusted to 6.0. Once prepared, OMP-21M18 was stored as 20 mL aliquots in 25-cc vials.

OMP-21M18 was administered at dosages of 0.5 mg/kg weekly to three subjects, 1.0 mg/kg weekly to three subjects, 2.5 mg/kg every two weeks to six subjects, 2.5 mg/kg weekly to six subjects, 5.0 mg/kg every two weeks to six subjects, 5.0 mg/kg weekly to three subjects, and 10.0 mg/kg every two weeks to six subjects. According to the study protocol, the administration period was nine weeks, unless a subject was removed from the study due to a dose limiting toxicity. Baseline blood pressure readings were taken just prior to administration of the first dosage. Toxicities were assessed using the National Institute of Health's Common Toxicity Criteria for Adverse Events (CTCAE) version 3.0. During the study, subjects were assessed for dose limiting toxicities from the time of the first dose through 7 days after administration of the fourth dose (Days 0-28). Subjects who experienced a dose limiting toxicity had their treatment with OMP-21M18 permanently discontinued. After nine weeks of treatment, if a subject continued to receive treatment and had no evidence of disease progression or if their tumor was smaller, the subject was allowed to continue to receive IV infusions of OMP-21M18 every other week until disease progression.

Twenty-two of the subjects treated in the trial had a prior diagnosis of hypertension. Of these subjects, 8 were taking a single medication and 1 subject each were taking two or three medications.

During the course of therapy, hypertension was reported for twelve of the thirty-three subjects, or 36% of patients treated with OMP-21M18. In eleven of these subjects, the hypertension was labeled "grade three" because an oral anti-hypertensive medication was administered and adjusted to successfully control the subject's blood pressure. In these eleven cases, the hypertension was asymptomatic and subjects were able to continue treatment with OMP-21M18.

There appears to be a dose relationship to hypertension. Hypertension has been observed across the full range of doses, with the greatest incidence at the highest dose administered. At the 10.0 mg/kg dose level, 6 of 6 subjects experienced Grade 3 hypertension (severe) or Grade 4 hypertension (life threatening).

TABLE 1

Incidence of Hypertension in Dosage Cohorts

| Dosage (mg/kg) | Schedule | Number of Patients | Grade 3 Hypertension | Grade 4 Hypertension | Total Incidence of Hypertension |
|---|---|---|---|---|---|
| 0.5 | weekly | 3 | 1 | 0 | 1/3 |
| 1.0 | weekly | 3 | 1 | 0 | 1/3 |
| 2.5 | every 2 weeks | 6 | 1 | 0 | 1/6 |
| 2.5 | weekly | 6 | 2 | 0 | 2/6 |
| 5.0 | every 2 weeks | 6 | 1 | 0 | 1/3 |
| 5.0 | weekly | 3 | 0 | 0 | 0/3 |
| 10.0 | every 2 weeks | 6[1] | 6 | 1 | 6/6 |

[1] one patient experienced both Grade 3 and Grade 4 hypertension

Example 2: Hypertension and Treatment in Subject No. 1

Subject 1, enrolled in the 0.5 mg/kg cohort, is a 78-year-old male with adenocarcinoma of the caecum with metastases to the liver. The Table of FIGS. 1A-B is a summary of Subject 1's blood pressure readings and anti-hypertensive treatments throughout the Phase I study of OMP-21M18. The subject's past medical history includes a diagnosis of hypertension, myocardial infarction (15 years prior), congestive heart failure, and paroxysmal atrial fibrillation. At study entry, the subject had been taking benazepril hydrochloride (Lotensin®) 30 mg po qd for hypertension for the past five months. On Day 1, the subject's baseline blood pressure was 135/73 mm Hg. On Day 0, the subject received his first weekly dose of OMP-21M18 at 0.5 mg/kg. Due to an increase in blood pressure to 183/89 on Day 24, his Lotensin® dose was increased to 40 mg po qd and amlodipine besylate (Norvasc®) 5 mg/qd was started. The Norvasc® dose was increased to 10 mg po qd on Day 32 due a blood pressure reading of 177/88 mm Hg. On Day 41, hydrochlorothiazide was added due to a blood pressure reading of 160/85 mm Hg. The highest blood pressure reported for subject 1 was on Day 21, 15 minutes post infusion, at 199/92. The subject continued on Lotensin®, Norvasc® and hydrochlorothiazide with adequate blood pressure control and no symptoms related to hypertension.

Example 3: Hypertension and Treatment in Subject No. 2

Subject 2, enrolled in the 1.0 mg/kg cohort, is a 55-year-old male with low-grade leiomyosarcoma. The Table of FIGS. 2A-2C is a summary of Subject 2's blood pressure readings and anti-hypertensive treatments throughout the Phase I study of OMP-21M18. The subject's prior medical history included a diagnosis of hypertension. At study entry, the subject had been taking lisinopril 10 mg po qd for over three years for hypertension. Baseline blood pressure was 141/85 mm Hg. On Day 0, the subject received his first weekly dose of OMP-21M18 at 1 mg/kg. On Day 7, the subject's blood pressure increased to a high of 177/93 mm Hg, and thus on Day 13 irbesartsan/hydrochlorothiazide 300/12.5 mg po qd was added to the lisinopril. On Day 14, the scheduled dose of study drug was not administered due to a hypertensive blood pressure reading of 173/110 mm Hg. The regimen of lisinopril 10 mg po qd plus irbesartsan/hydrochlorothiazide 300/12.5 mg po qd did not adequately control the subject's blood pressure, and thus on Day 17, the irbesartan/hydrochlorothiazide and lisinopril were discontinued and labetalol 100 mg po bid and Prinzide® 10/12.5 po qd were initiated. On Day 21, the labetalol was increased to 300 mg q am and 200 mg q pm due to a blood pressure reading of 164/112 mm Hg. Two days later, the labatolol dose was increased to 400 mg po bid. This regimen controlled the subject's blood pressure until Day 55, when a blood pressure reading of 163/91 mm Hg was observed that resulted in increasing the Prinzide® dose to 20/25 po qd. On Day 84, the subject's blood pressure was 167/102 mm Hg and lasix 20 mg po qd was added to the regimen. Due to the high blood pressure reading on Day 84, the subjects dose of OMP-21M18 was not administered. On Day 87, to regain blood pressure control, Norvasc® 10 mg po qd was started. The subject's regimen of labetalol 400 po bid, lasix 20 mg po qd, Norvasc® 10 mg po qd, and Prinzide® 20/25 mg po bid, subsequently controlled his blood pressure, allowing him to receive 7 additional doses of OMP-21M18 without hypertension.

Example 4: Hypertension and Treatment in Subject No. 3

Subject 3, enrolled in the 2.5 mg/kg cohort, is a 64-year-old woman with a choroidal melanoma of the right eye and metastases in both the liver and the lung. The Table of FIG. 3 is a summary of Subject 3's blood pressure readings and anti-hypertensive treatments throughout the Phase I study of OMP-21M18. This subject had no prior history of hypertension. The subject's baseline blood pressure was 96/54 mm Hg. On Day 0, the subject received her first weekly dose of OMP-21M18 at 2.5 mg/kg. On Day 21, the subject had a blood pressure reading of 159/90 mmHg and was started on Dyazide® (hydrochlorothiazide and triamterene) 1 po qd. The subject's blood pressure was adequately controlled until Day 112, when her blood pressure was noted to be elevated to 152/77 mm Hg. To regain blood pressure control, Dyazide® was discontinued and the subject was begun on Norvasc® (amlodipine besylate) 5 mg po qd. On Day 141, Norvasc® treatment was discontinued due to ankle edema and lisinopril 20 mg po qd was begun. On Day 144, the subject's lisinopril dose was increased to 20 mg po bid. On Day 146 the subject's blood pressure reading was 143/85 mm Hg. The subject has not had symptoms related to the blood pressure increase. The subject remained on treatment and received 13 infusions of OMP-21M18.

Example 5: Hypertension and Treatment in Subject No. 4

Subject 4, enrolled in the 2.5 mg/kg cohort, had a history of hypertension and was taking dyazide and lisinopril at study entry. The subject's blood pressure at baseline was 118/73. On Day 14, the subject had a blood pressure of 153/79. The increase in blood pressure was not related to the study drug according to the Investigator. The subject did not have symptoms related to the hypertension.

Example 6: Hypertension and Treatment in Subject No. 5

Subject 5, enrolled in the 10 mg/kg cohort, is a 56-year-old female with stage IV colorectal cancer. The Table of FIG. 4 is a summary of Subject 5's blood pressure readings and anti-hypertensive treatments throughout the Phase I study of OMP-21M18. The subject's past medical history includes diagnoses of coronary heart disease, atherosclerosis, and exertional angina (class 1). Subject 5's baseline blood pressure was 130/90 mm Hg on Day −28. On Day 0, the subject received her first dose of once every other week OMP-21M18 at 10 mg/kg. On Day 9, the subject's blood pressure was high, at 160/90 mm Hg, and she was started on lisinopril 10 mg po qd. On Day 14, the subject's blood pressure readings in the clinic were lower, at 135-140/90 mm Hg, and therefore her dose of lisinopril was reduced to 5 mg po qd. On Day 26, the subject's blood pressure at home was 170/90 mm Hg and was treated with a single dose of captopril 25 mg po. On Day 28, the subject's dosage of lisinopril was increased back to 10 mg po qd. On Day 56, the dose of lisinopril was increased to 10 mg po bid due to blood pressure readings of 140-145/90 mm Hg. On Day 62, the subject had a blood pressure of 190/120 mm Hg and was seen by a cardiologist who discontinued the lisinopril and started her on lozartan 25 mg po qd, bisoprolol 2.5 mg po qd and amlodipine 5 mg po qd. Three days later, on Day 65, the subject's blood pressure was still 170/106 mm Hg. The cardiologist increased the dose of lozartan to 50 mg po qd and increased the dose of bisoprolol to 5 mg po qd.

Example 7: Hypertension and Treatment in Subject No. 6

Subject 6, enrolled in the 10 mg/kg cohort, did not have a prior history of hypertension. The subject's baseline blood pressure was 125/90. On Day 9, the subject was started on enalapril 10 mg bid. The subsequent blood pressure was 140/90. On Day 28 the subject had a single blood pressure reading of 150/90. A subsequent blood pressure reading was 150/90. The subject did not have symptoms related to hypertension and continued to receive treatment.

Example 8: Hypertension and Treatment in Subject No. 7

Subject 7, enrolled in the 10 mg/kg cohort, is a 71-year-old female with stage IV adenocarcinoma of the rectosigmoid junction. The Table of FIG. 5 is a summary of Subject 7's blood pressure readings and anti-hypertensive treatments throughout the Phase I study of OMP-21M18. The subject's past medical history includes diagnoses of coronary heart disease, arterial hypertension, and atherosclerosis. The subject has been taking enalapril 5 mg po bid for hypertension for the past 10 years. On Day −1, the subject's baseline blood pressure was 135/90 mm Hg. On Day 0, she received her first dose of once every other week OMP-21M18 at 10 mg/kg. On Day 9, the subject's enalapril dose was increased to 10 mg bid when the subject's blood pressure reading was 170/90 mm Hg. On Day 56, amlodipine 5 mg po qd was started when the subject's blood pressure reading was 155/90 mm Hg. The subject's blood pressure readings on Day 70 were 145-150/90 mm Hg. The subject did not have symptoms related to hypertension and continued to receive treatment.

Example 9: Hypertension and Treatment in Subject No. 8

Subject 8, enrolled in the 10 mg/kg cohort, is a 58-year-old man with stage IV colorectal cancer. The Table of FIG. 6 is a summary of Subject 8's blood pressure readings and anti-hypertensive treatments throughout the Phase I study of OMP-21M18. His past medical history includes a diagnosis hypertension. At the time of study entry, the subject had been taking captopril 25 mg po qd as needed for the past 6 years to control his blood pressure. The subject's baseline blood pressure on Day −28 was 140/90 mm Hg. On Day 0, he received his first dose of once every other week OMP-21M18 10 mg/kg. On Day 18, the subject's captopril dose was changed to 12.5 po qd due to a home blood pressure reading of 160/90 mm Hg on Day 17. The subject's next blood pressure in the clinic on Day 22 was 130/80 mm Hg. On Days 23-28, the subjects blood pressure at home measured 150/90 mm Hg and thus the subject's captopril dose was increased to 25 mg po qd. Subsequently, the subject received 5 additional doses of OMP-21M18 without any further adjustments of his blood pressure medications. The subject did not had symptoms related to the reported hypertension and remained on treatment.

Example 10: Hypertension and Treatment in Subject No. 9

Subject 9, enrolled in the 10 mg/kg cohort, is a 54-year-old man with locally advanced adenocarcinoma of the head of the pancreas. The Table of FIG. 7 is a summary of Subject 9's blood pressure readings and anti-hypertensive treatments throughout the Phase I study of OMP-21M18. The subject received prior treatment with gemcitabine. The subject did not have a history of hypertension. The subject's blood pressure on Day −1 was 115/75 mm Hg. On Day 0, he received his first dose of once every other week OMP-21M18 10 mg/kg. On Day 3, the subject reported an increased blood pressure of 140-145/90-95 mm Hg and was started on nifedipine 20 mg po qd. The subject's next blood pressure reading on Day 7 was 130/80 mm Hg. On Day 74, the nifedipine was discontinued by the subject due to normalization of his blood pressure (115/75 mm Hg). The subject has not had symptoms related to hypertension and remains on treatment at Day 81.

```
SEQ ID NO: 1 (Heavy chain CDR1)
TAYYIH

SEQ ID NO: 2 (Heavy chain CDR2, H2)
YISCYNGATNYNQKFKG

SEQ ID NO: 3 (Heavy chain CDR2 H7)
YISSYNGATNYNQKFKG

SEQ ID NO: 4 (Heavy chain CDR2 H9)
YISVYNGATNYNQKFKG

SEQ ID NO: 5 (Heavy chain CDR3)
RDYDYDVGMDY

SEQ ID NO: 7 (Heavy chain variable region, H7)
QVQLVQSGAEVKKPGASVKISCKASGYSFTAYYIHWVKQAPGQGLEWIGY
ISSYNGATNYNQKFKGRVTFTTDTSTSTAYMELRSLRSDDTAVYYCARDY
DYDVGMDYWGQGTLVTVSS SEQ ID NO: 7 (Light chain CDR1)
RASESVDNYGISFMK SEQ ID NO: 8 (Light chain CDR2)
AASNQGS SEQ ID NO: 9 (Light chain CDR3)
QQSKEVPWTFGG SEQ ID NO: 10 (Light chain variable region)
DIVMTQSPDSLAVSLGERATISCRASESVDNYGISFMKWFQQKPGQPPKL
LIYAASNQGSGVPDRFSGSGSGTDFTLTISSLQAEDVAVYYCQQSKEVPW
TFGGGTKVEIK SEQ ID NO: 11 (Human DLL4 N-Terminal Region)
MAAASRSASGWALLLLVALWQQRAAGSGVFQLQLQEFINERGVLASGRPC

EPGCRTFFRVCLKHFQAVVSPGPCTFGTVSTPVLGTNSFAVRDDSSGGGR

NPLQLPFNFTWPGTFSLIIEAWHAPGDDLRPEALPPDALISKIAIQGSLA

VGQN
```

---

What we claim is:

1. A method of ameliorating hypertension in a subject receiving treatment with a delta-like ligand 4 (DLL4) antagonist, the method comprising:
   administering to the subject a therapeutically effective amount of one or more anti-hypertensive agents to control hypertension caused by the antagonist,
   wherein the DLL4 antagonist comprises a monoclonal antibody that specifically binds human DLL4.

2. The method of claim 1, wherein the monoclonal antibody comprises an intact monoclonal antibody.

3. The method of claim 1, wherein the monoclonal antibody is encoded by the plasmid having ATCC deposit no. PTA-8425.

4. The method of claim 1, wherein the monoclonal antibody competes for specific binding to human DLL4 with an antibody encoded by the plasmid deposited with ATCC, having deposit no. PTA-8425.

5. The method of claim 1, wherein the monoclonal antibody comprises: (i) a heavy chain variable region comprising CDR amino acid sequences CDR1 (SEQ ID NO:1); CDR2 (SEQ ID NO:2, SEQ ID NO:3, or SEQ ID NO:4); and CDR3 (SEQ ID NO:5), and (ii) a light chain variable region comprising CDR amino acid sequences CDR1 (SEQ ID NO:7); CDR2 (SEQ ID NO:8); and CDR3 (SEQ ID NO:9).

6. The method of claim 5, wherein the heavy chain variable region comprises CDR amino acid sequences CDR1 (SEQ ID NO:1), CDR2 (SEQ ID NO:3), and CDR3 (SEQ ID NO:5), and the light chain variable region comprises CDR amino acid sequences CDR1 (SEQ ID NO:7); CDR2 (SEQ ID NO:8); and CDR3 (SEQ ID NO:9).

7. The method of claim 1, wherein the monoclonal antibody comprises a heavy chain variable region comprising the amino acid sequence of SEQ ID NO:6.

8. The method of claim 7, wherein the monoclonal antibody comprises a light chain variable region comprising the amino acid sequence of SEQ ID NO:10.

9. The method of claim 1, wherein the monoclonal antibody comprises a light chain variable region comprising the amino acid sequence of SEQ ID NO:10.

10. The method of claim 1, wherein the monoclonal antibody is a humanized, chimeric, or human antibody.

11. The method of claim 1, wherein the monoclonal antibody comprises an antibody fragment.

12. The method of claim 11, wherein the monoclonal antibody is a multispecific antibody.

13. The method of claim 1, wherein the monoclonal antibody is a fusion protein that comprises an immunoglobulin molecule that specifically binds human DLL4 through at least one antigen recognition site within the variable region of the immunoglobulin molecule.

14. The method of claim 1, wherein the anti-hypertensive agent is selected from the group consisting of a diuretic, an adrenergic receptor antagonist, an adrenergic receptor agonist, a calcium channel blocker, an ACE inhibitor, an angiotensin II receptor antagonist, an aldosterone antagonist, a vasodilator, a renin inhibitor, and combinations thereof.

15. The method of claim 14, wherein the anti-hypertensive agent is a diuretic selected from the group, consisting of: furosemide, bumetanide, ethacrynic acid, torsemide, epitizide, hydrochlorothiazide, hydroflumethiazide, chlorothiazide bendroflumethiazide, polythiazide, trichlormethiazide cyclopenthiazide, methyclothiazide, cyclothiazide, mebutizide, indapamide, chlortalidone, metolazone, quinethazone, clopamide, mefruside, clofenamide, meticrane, xipamide, clorexolone, fenquizone, amiloride, triamterene, eplerenone, benzamil, potassium canrenoate, canrenone, spironolactone mannitol, glucose, urea, conivaptan, relcovaptan, nelivaptan, lixivaptan, mozavaptan, satavaptan, tolvaptan, demeclocycline, mersalyl acid, meralluride, mercaptomerin, mercurophyllme, merethoxyllme procaine, calomel, caffeine, theobromine, paraxanthine, theophylline, acetazolamide, methazolamide, dorzolamide, sulfonamide, topiramate, amanozine, arbutin, chlorazanil etozolin, hydracarbazine, isosorbide, metochalcone, muzohmme, perhexiline, and ticrynafen.

16. The method of claim 14, wherein the anti-hypertensive agent is an adrenergic receptor antagonist selected from the group consisting of: atenolol, metoprolol, nadolol oxprenolol, pindolol, propranolol, timolol, acebutolol, bisoprolol, esmolol, labetalol, carvedilol, bucindolol, nebivolol, amosulalol, arotinolol, befunolol, betaxolol, bevantolot, bopindolol, bucumolol, bufetolol, bufuralol, bumtrolol, bupranolol, butidrine hydrochloride, butofilolol, carazolol, carteolol, celiprolol, cetamolol, cloranololdilevalol, epanolol, indenolol, levobunolol, mepindolol, metipranolol, moprolol, nadoxolol, nipradilol, penbutolol, practolol, pronethalol, sotalol, sulfmalol, talinolol, tertatolol, tilisolol, toliprolol, xibenolol, phenoxybenzamine, prazosin, doxazosin, terazosin, trimazosin, phentolamine, amosulalol, arotinolol, dapiprazole, fenspinde, indoramin, labetalol, naftopidil, nicergolme, tamsulosin, tolazolme, moxonidine, reserpine, and yohimbine.

17. The method of claim 14, wherein the anti-hypertensive agent is an adrenergic receptor agonist selected from the group consisting of: clonidine, methyldopa, guanfacine, methoxamine, methylnorepinephrine, oxymetazoline, phenylephrine, guanabenz, guanoxabenz, guanethidine, xylazine, and tizanidme.

18. The method of claim 14, wherein the anti-hypertensive agent is a calcium channel blocker selected from the group consisting of: amlodipine, felodipine, nicardipine, nifedipine, nimodipine, isradipine, nitrendipine, aranidipine, barnidipine, benidipine, cilnidipine, efonidipine, elgodipine, lacidipine, lercanidipine, manidipine, nilvadipine, nisoldipine, diltiazem, verapamil, bepridil, clentiazem, fendiline, gallopamil, mibefradil, prenylamine, semotiadil, terodiline, cinnarizine, flunarizine, lidoflazine, lomerizine, bencyclane, etafenone, and perhexiline.

19. The method of claim 14, wherein the anti-hypertensive agent is an ACE inhibitor.

20. The method of claim 19, wherein the ACE inhibitor is selected from the group consisting of: captopril, zofenopril, enalapril, ramipril, quinapril, perindopril, lismopril, benazepril, fosinopril, ceronapril, casokinins, lactokinins, teprotide, alacepril, cilazapril, delapril, imidapnl, moexipnl, rentiapril, spirapril, temocapril, moveltipnl and trandolapril.

21. The method of claim 14, wherein the anti-hypertensive agent is an angiotensin II receptor antagonist selected from the group consisting of: candesartan, eprosartan, irbesartan, losartan, olmesartan, telmisartan, and valsartan.

22. The method of claim 14, wherein the anti-hypertensive agent is an aldosterone antagonist selected from the group consisting of: eplerenone, canrenone, and spironolactone.

23. The method of claim 14, wherein the anti-hypertensive agent is a vasodilator selected from the group consisting of: bencyclane, cinnarizine, citicoline, cyclandelate, ciclonicate, diisopropylamine dichloroacetate, eburnamonine, fasudil, fenoxedil, flunarizine, ibudilast, ifenprodil, lomerizine, nafronyl, nicametate, nicergoline, nimodipine, papaverine, tinofedrine, vincamine, vinpocetine, viquidil, amotriphene, bendazol, benfurodil hemisuccinate, benziodarone, chloracizme, chromonar, clobenfural, clonitrate, cloricromen, dilazep, dipyridamole, droprenilamine, efloxate, erythrityl tetranitrate, etafenone, fendiline, floredil, ganglefene, hexestrol bis(P-diethylaminoethyl) ether, hexobendine, itramin tosylate, khellin, lidoflazine, mannitol hexanitrate, medibazine, nitroglycerin, pentaerythritol tetranitrate, pentrinitrol, perhexiline, pimefylline, prenylamine, propatyl nitrate, trapidil, tricromyl, trimetazidine, trolnitrate phosphate, sildenafil, tadalafil, vardenafil, sodium nitroprusside, isosorbide mononitrate, isosorbide dinitrate, pentaerythritol, tetranitrate, theobromine, visnadine, aluminum nicotinate, bamethan, bencyclane, betahistine, brandykinin, brovincamine, bufeniode, buflomedil, butalamine, cetiedil, ciclonicate, cinepazide, cinnarizine, cyclandelate, diisopropylamine dichloroacetate, eledoisin, fenoxedil, flunarizine, hepronicate, ifenprodil, iloprost, inositol niacinate, isoxsuprine, kallidin, kallikrein, moxisylyte, nafronyl, nicametate, nicergoline, nicofuranose, nylidrin, pentifyllme, pentoxifylline, piribedil, prostaglandin E1, suloctidil, tolazoline, and xanthinol niacinate.

24. The method of claim 14, wherein the anti-hypertensive agent is a renin inhibitor selected from the group consisting of: aliskiren and remikiren.

25. The method of claim 1, wherein the monoclonal antibody is an immunoglobulin molecule that specifically binds human DLL4 through at least one antigen recognition site within the variable region of the immunoglobulin molecule.

26. A method of detecting and ameliorating hypertension in a subject receiving treatment with a delta-like ligand 4 (DLL4) antagonist, the method comprising:
    (a) measuring the blood pressure of the subject after receiving treatment with the DLL4 antagonist; and
    (b) administering to the subject a therapeutically effective amount of one or more anti-hypertensive agents to control hypertension caused by the antagonist,
    wherein the DLL4 antagonist comprises a monoclonal antibody that specifically binds human DLL4.

27. The method of claim 26, wherein the monoclonal antibody comprises an intact monoclonal antibody.

28. The method of claim 26, wherein the monoclonal antibody is encoded by the plasmid having ATCC deposit no. PTA-8425.

29. The method of claim 26, wherein the monoclonal antibody competes for specific binding to human DLL4 with an antibody encoded by the plasmid deposited with ATCC, having deposit no. PTA-8425.

30. The method of claim 26, wherein the monoclonal antibody comprises: (i) a heavy chain variable region comprising CDR amino acid sequences CDR1 (SEQ ID NO:1); CDR2 (SEQ ID NO:2, SEQ ID NO:3, or SEQ ID NO:4); and CDR3 (SEQ ID NO:5), and (ii) a light chain variable region comprising CDR amino acid sequences CDR1 (SEQ ID NO:7); CDR2 (SEQ ID NO:8); and CDR3 (SEQ ID NO:9).

31. The method of claim 30, wherein the heavy chain variable region comprises CDR amino acid sequences CDR1 (SEQ ID NO:1), CDR2 (SEQ ID NO:3), and CDR3 (SEQ ID NO:5), and the light chain variable region comprises CDR amino acid sequences CDR1 (SEQ ID NO:7); CDR2 (SEQ ID NO:8); and CDR3 (SEQ ID NO:9).

32. The method of claim 26, wherein the monoclonal antibody comprises a heavy chain variable region comprising the amino acid sequence of SEQ ID NO:6.

33. The method of claim 32, wherein the monoclonal antibody comprises a light chain variable region comprising the amino acid sequence of SEQ ID NO:10.

34. The method of claim 26, wherein the monoclonal antibody comprises a light chain variable region comprising the amino acid sequence of SEQ ID NO:10.

35. The method of claim 26, wherein the monoclonal antibody is a humanized, chimeric, or human antibody.

36. The method of claim 26, wherein the monoclonal antibody comprises an antibody fragment.

37. The method of claim 36, wherein the monoclonal antibody is a multispecific antibody.

38. The method of claim 26, wherein the monoclonal antibody is a fusion protein that comprises an immunoglobulin molecule that specifically binds human DLL4 through at least one antigen recognition site within the variable region of the immunoglobulin molecule.

39. The method of claim 26, wherein the anti-hypertensive agent is selected from the group consisting of a diuretic, an adrenergic receptor antagonist, an adrenergic receptor agonist, a calcium channel blocker, an ACE inhibitor, an angiotensin II receptor antagonist, an aldosterone antagonist, a vasodilator, a renin inhibitor, and combinations thereof.

40. The method of claim 39, wherein the anti-hypertensive agent is a diuretic selected from the group, consisting of: furosemide, bumetanide, ethacrynic acid, torsemide, epitizide, hydrochlorothiazide, hydroflumethiazide, chlorothiazide bendroflumethiazide, polythiazide, trichlormethiazide cyclopenthiazide, methyclothiazide, cyclothiazide, mebutizide, indapamide, chlortalidone, metolazone, quinethazone, clopamide, mefruside, clofenamide, meticrane, xipamide, clorexolone, fenquizone, amiloride, triamterene, eplerenone, benzamil, potassium canrenoate, canrenone, spironolactone mannitol, glucose, urea, conivaptan, relcovaptan, nelivaptan, lixivaptan, mozavaptan, satavaptan, tolvaptan, demeclocycline, mersalyl acid, meralluride, mercaptomerin, mercurophyllme, merethoxyllme procaine, calomel, caffeine, theobromine, paraxanthine, theophylline, acetazolamide, methazolamide, dorzolamide, sulfonamide, topiramate, amanozine, arbutin, chlorazanil etozolin, hydracarbazine, isosorbide, metochalcone, muzohmme, perhexiline, and ticrynafen.

41. The method of claim 39, wherein the anti-hypertensive agent is an adrenergic receptor antagonist selected from the group consisting of: atenolol, metoprolol, nadolol oxprenolol, pindolol, propranolol, timolol, acebutolol, bisoprolol, esmolol, labetalol, carvedilol, bucindolol, nebivolol, amosulalol, arotinolol, befunolol, betaxolol, bevantolot, bopindolol, bucumolol, bufetolol, bufuralol, bumtrolol, bupranolol, butidrine hydrochloride, butofilolol, carazolol, carteolol, celiprolol, cetamolol, cloranololdilevalol, epanolol, indenolol, levobunolol, mepindolol, metipranolol, moprolol, nadoxolol, nipradilol, penbutolol, practolol, pronethalol, sotalol, sulfmalol, talinolol, tertatolol, tilisolol, toliprolol, xibenolol, phenoxybenzamine, prazosin, doxazosin, terazosin, trimazosin, phentolamine, amosulalol, arotinolol, dapiprazole, fenspinde, indoramin, labetalol, naftopidil, nicergolme, tamsulosin, tolazolme, moxonidine, reserpine, and yohimbine.

42. The method of claim 39, wherein the anti-hypertensive agent is an adrenergic receptor agonist selected from the group consisting of: clonidine, methyldopa, guanfacine, methoxamine, methylnorepinephrine, oxymetazoline, phenylephrine, guanabenz, guanoxabenz, guanethidine, xylazine, and tizanidme.

43. The method of claim 39, wherein the anti-hypertensive agent is a calcium channel blocker selected from the group consisting of: amlodipine, felodipine, nicardipine, nifedipine, nimodipine, isradipine, nitrendipine, aranidipine, barnidipine, benidipine, cilnidipine, efonidipine, elgodipine, lacidipine, lercanidipine, manidipine, nilvadipine, nisoldipine, diltiazem, verapamil, bepridil, clentiazem, fendiline, gallopamil, mibefradil, prenylamine, semotiadil, terodiline, cinnarizine, flunarizine, lidoflazine, lomerizine, bencyclane, etafenone, and perhexiline.

44. The method of claim 39, wherein the anti-hypertensive agent is an ACE inhibitor.

45. The method of claim 44, wherein the ACE inhibitor is selected from the group consisting of: captopril, zofenopril, enalapril, ramipril, quinapril, perindopril, lismopril, benazepril, fosinopril, ceronapril, casokinins, lactokinins, teprotide, alacepril, cilazapril, delapril, imidapnl, moexipnl, rentiapril, spirapril, temocapril, moveltipnl and trandolapril.

46. The method of claim 39, wherein the anti-hypertensive agent is an angiotensin II receptor antagonist selected from the group consisting of: candesartan, eprosartan, irbesartan, losartan, olmesartan, telmisartan, and valsartan.

47. The method of claim 39, wherein the anti-hypertensive agent is an aldosterone antagonist selected from the group consisting of: eplerenone, canrenone, and spironolactone.

48. The method of claim 39, wherein the anti-hypertensive agent is a vasodilator selected from the group consisting of: bencyclane, cinnarizine, citicoline, cyclandelate, ciclonicate, diisopropylamine dichloroacetate, eburnamonine, fasudil, fenoxedil, flunarizine, ibudilast, ifenprodil, lomerizine, nafronyl, nicametate, nicergoline, nimodipine, papaverine, tinofedrine, vincamine, vinpocetine, viquidil, amotriphene, bendazol, benfurodil hemisuccinate, benziodarone, chloracizme, chromonar, clobenfural, clonitrate, cloricromen, dilazep, dipyridamole, droprenilamine, efloxate, erythrityl tetranitrate, etafenone, fendiline, floredil, ganglefene, hexestrol bis(P-diethylaminoethyl) ether, hexobendine, itramin tosylate, khellin, lidoflazine, mannitol hexanitrate, medibazine, nitroglycerin, pentaerythritol tetranitrate, pentrinitrol, perhexiline, pimefylline, prenylamine, propatyl nitrate, trapidil, tricromyl, trimetazidine, trolnitrate phosphate, sildenafil, tadalafil, vardenafil, sodium nitroprusside, isosorbide mononitrate, isosorbide dinitrate, pentaerythritol, tetranitrate, theobromine, visnadine, aluminum nicotinate, bamethan, bencyclane, betahistine, brandykinin, brovincamine, bufeniode, buflomedil, butalamine, cetiedil, ciclonicate, cinepazide, cinnarizine, cyclandelate, diisopropylamine dichloroacetate, eledoisin, fenoxedil, flunarizine, hepronicate, ifenprodil, iloprost, inositol niacinate, isoxsuprine, kallidin, kallikrein, moxisylyte, nafronyl, nicametate, nicergoline, nicofuranose, nylidrin, pentifyllme, pentoxifylline, piribedil, prostaglandin E1, suloctidil, tolazoline, and xanthinol niacinate.

49. The method of claim 39, wherein the anti-hypertensive agent is a renin inhibitor selected from the group consisting of: aliskiren and remikiren.

50. The method of claim 26, wherein the subject is a human.

51. The method of claim 26, wherein the monoclonal antibody is an immunoglobulin molecule that specifically binds human DLL4 through at least one antigen recognition site within the variable region of the immunoglobulin molecule.

* * * * *